US009359440B2

(12) United States Patent
Cheong et al.

(10) Patent No.: US 9,359,440 B2
(45) Date of Patent: Jun. 7, 2016

(54) BISPECIFIC CHIMERIC PROTEINS COMPRISING DARPINS

(71) Applicant: Samsung Electronics Co., Ltd., Suwon-si, Gyeonggi-do (KR)

(72) Inventors: Kwang Ho Cheong, Seoul (KR); Young Jun Koh, Yongin-si (KR); Min-Kyung Kim, Seoul (KR); Powei Lin, Hwaseong-si (KR); Seung Hyun Lee, Suwon-si (KR); Jung Wook Lee, Yongin-si (KR); Mi Young Cho, Seoul (KR); Jae Woong Hwang, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/444,632

(22) Filed: Jul. 28, 2014

(65) Prior Publication Data

US 2015/0030596 A1    Jan. 29, 2015

(30) Foreign Application Priority Data

Jul. 26, 2013    (KR) ........................ 10-2013-0089120

(51) Int. Cl.
*C07K 16/28*    (2006.01)
*C07K 16/32*    (2006.01)
*C07K 14/705*    (2006.01)

(52) U.S. Cl.
CPC ........... *C07K 16/2863* (2013.01); *C07K 14/705* (2013.01); *C07K 16/32* (2013.01); *C07K 2317/24* (2013.01); *C07K 2317/31* (2013.01); *C07K 2317/53* (2013.01); *C07K 2317/565* (2013.01); *C07K 2317/567* (2013.01); *C07K 2317/622* (2013.01); *C07K 2317/73* (2013.01); *C07K 2317/76* (2013.01); *C07K 2317/77* (2013.01); *C07K 2317/92* (2013.01); *C07K 2318/20* (2013.01); *C07K 2319/30* (2013.01); *C07K 2319/33* (2013.01)

(58) Field of Classification Search
CPC .. C07K 14/47; C07K 14/705; C07K 16/2863; C07K 16/32; C07K 19/00
See application file for complete search history.

(56) References Cited

U.S. PATENT DOCUMENTS

| 7,417,130 | B2 | 8/2008 | Stumpp et al. |
| 8,110,653 | B2 | 2/2012 | Stumpp et al. |
| 2009/0148905 | A1 | 6/2009 | Ashman et al. |
| 2010/0076178 | A1 | 3/2010 | Ghayur et al. |
| 2010/0254988 | A1 | 10/2010 | Bossenmaier et al. |
| 2010/0254989 | A1 | 10/2010 | Bossenmaier et al. |
| 2011/0008345 | A1 | 1/2011 | Ashman et al. |
| 2012/0207754 | A1* | 8/2012 | Giacalone et al. ......... 424/134.1 |
| 2013/0089542 | A1 | 4/2013 | Lee et al. |
| 2013/0089557 | A1 | 4/2013 | Cheong et al. |
| 2013/0156772 | A1 | 6/2013 | Bossenmaier et al. |
| 2013/0273054 | A1 | 10/2013 | Bossenmaier et al. |
| 2014/0154251 | A1 | 6/2014 | Lee et al. |

FOREIGN PATENT DOCUMENTS

| KR | 2013-0037153 A | 4/2013 |
| WO | WO 2009/068649 A2 | 6/2009 |
| WO | WO 2009/134776 A2 | 11/2009 |
| WO | WO 2010/115551 A1 | 10/2010 |
| WO | WO 2013/051878 A2 | 4/2013 |
| WO | WO 2014/060365 A1 | 4/2014 |

OTHER PUBLICATIONS

Paul, WE. Fundamental Immunology. 3rd ed. Raven Press, NY, Chap. 9, pp. 292-295, 1993.*
Rudikoff S. et al. Proc. Natl. Acad. Sci. USA. 79:1979-1983, 1982.*
Colman, PM. Research in Immunology. Elsevier, NY, 145(1):33-36, 1994.*
Eggel A, et al. Allergy. 66(7):961-968, Jul. 2011. Available online at -doi: 10.1111/j.1398-9995.2011.02546.x.*
European Patent Office, Extended European Search Report in Application No. 14178672.3 dated Dec. 16, 2014 (12 pgs).
Boersma et al., Bispecific Designed Ankyrin Repeat Proteins (DARPins) Targeting Epidermal Growth Factor Receptor Inhibit A431 Cell Proliferation and Receptor Recycling, *Journal of Biological Chemistry*, 286 (48): 41273-41285 (2011).
Engelman et al., MET Amplification Leads to Gefitinib Resistance in Lung Cancer by Activating ERBB3 Signaling, *Science*, 316: 1039-1043 (2007).
Lai et al., Crosstalk in Met receptor oncogenesis, *Trends in Cell Biology*, 19(10): 542-551 (2009).
Reznik et al., Transcription-Dependent Epidermal Growth Factor Receptor Activation by Hepatocyte Growth Factor, *Mol. Cancer Res.*, 6(10): 139-150 (2008).
Sequist et al., First-Line Gefitinib in Patients With Advanced Non-Small-Cell Lung Cancer Harboring Somatic EGFR Mutations, *Jour. Clinical Oncology*, 26(15): 2442-2449 (2008).
Sequist et al., Genotypic and Histological Evolution of Lung Cancers Acquiring Resistance to EGFR Inhibitors, *Science Translational Medicine*, 3 (75):1-12 (2011).
Steiner et al, Efficient Selection of DARPins with Sub-nanomolar Affinities using SRP Phage Display, *J. Mol. Biol.*, 382: 1211-1227 (2008).
Steiner et al., "Efficient Selection of DARPins with Sub-nanomolar Affinities using SRP Phage Display," *J. Mol. Biol.*, 382: 1211-1227 (2008) (including Supplementary Material, pp. 1-17).
Theurillat et al., Designed ankyrin repeat proteins: a novel tool for testing epidermal growth factor receptor 2 expression in breast cancer, *Modern Pathology*, 23:1289-1297 (2010).
European Patent Office, Office Action in Application No. 14178672.3 dated Jan. 12, 2016.

* cited by examiner

*Primary Examiner* — Robert Landsman
(74) *Attorney, Agent, or Firm* — Leydig, Voit & Mayer, Ltd.

(57) ABSTRACT

A bispecific chimeric protein including a designed ankyrin repeat protein (DARPin), and an IgG antibody, an scFv-Fc antibody fragment, or a combination thereof, linked to the DARPin; a method for treating or preventing cancer using the same; and related methods and compositions.

18 Claims, 27 Drawing Sheets
(2 of 27 Drawing Sheet(s) Filed in Color)

FIG. 21A

N-Cap (positions 1–30)

| SEQ ID NO. | Clone | NxC | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|---|
| 151 | Clone | NxC | D | L | G | K | K | L | L | E | A | A | R | A | G | Q | D | D | E | V | R | I | L | M | A | N | G | A | D | V | N | A |
| 120 | E_01 | N3C | . | . | . | . | . | . | . | . | . | . | . | . | . | . | . | . | . | . | . | . | . | . | . | . | . | . | . | . | . | . |
| 121 | E_67 | N3C | . | . | . | . | . | . | . | . | . | . | . | . | . | . | . | . | . | . | . | . | . | . | . | . | . | . | . | . | . | . |
| 122 | E_68 | N3C | . | . | . | . | . | . | . | . | . | . | . | . | . | . | . | . | . | . | . | . | . | . | . | . | . | . | . | . | . | . |
| 123 | E_69 | N4C | . | . | . | . | . | . | . | . | . | . | . | . | . | . | . | . | . | . | . | . | . | . | . | . | . | . | . | . | . | . |
| 124 | 9_16 | N3C | . | . | . | . | . | . | . | . | . | . | . | . | . | . | . | . | . | . | . | . | . | . | . | . | . | . | . | . | . | . |
| 125 | 9_26 | N3C | . | . | . | . | . | . | . | . | . | . | . | . | . | . | . | . | . | . | . | . | . | . | . | . | . | . | . | . | . | . |
| 126 | 9_29 | N3C | . | . | . | . | . | . | . | . | . | . | . | . | . | . | . | . | . | . | . | . | . | . | . | . | . | . | . | . | . | . |
| 127 | H_14 | N3C | . | . | . | . | . | . | . | . | . | . | . | . | . | . | . | . | C | . | . | . | . | . | . | . | . | . | . | . | . | . |
| 128 | B4_01 | N4C | . | . | . | . | . | . | . | . | . | . | . | . | . | . | . | . | . | H | . | . | . | . | . | . | . | . | . | . | . | . |
| 129 | B4_02 | N3C | . | . | . | . | . | . | . | . | . | . | . | . | . | . | . | . | . | . | . | . | . | . | . | . | . | . | . | . | . | . |
| 130 | B4_07 | N3C | . | . | . | . | . | . | . | . | . | . | . | . | . | . | . | . | . | . | . | . | . | . | . | . | . | . | . | . | . | . |
| 131 | B4_33 | N3C | . | . | . | . | . | . | . | . | . | . | . | . | . | . | . | . | . | . | . | . | . | . | . | . | . | . | . | . | . | . |
| 132 | B4_45 | N3C | . | . | . | . | . | . | . | . | . | . | . | . | . | . | . | . | . | . | . | . | . | . | . | . | . | . | . | . | . | . |
| 133 | B4_50 | N4C | . | . | . | . | . | . | . | . | . | . | . | . | . | . | . | . | . | . | . | . | . | . | . | . | . | . | . | . | . | . |
| 134 | B4_58 | N5C | . | . | . | . | . | . | . | . | . | T | . | . | . | . | . | . | . | . | . | . | . | . | . | . | . | . | . | . | . | . |
| 135 | L_01 | N3C | . | . | . | . | . | . | . | . | . | . | . | . | . | . | . | . | . | . | . | . | . | . | . | . | . | . | . | . | . | . |
| 136 | L_02 | N2C | . | . | . | . | . | . | . | . | . | . | . | . | . | . | . | . | . | . | . | . | . | . | . | . | . | . | . | . | . | . |
| 137 | L_07 | N2C | . | . | . | . | . | . | . | . | . | . | . | . | . | . | . | . | . | . | . | . | . | . | . | . | . | . | . | . | . | . |
| 138 | L_11 | N3C | . | . | . | . | . | . | . | . | . | . | . | . | . | . | . | . | . | . | . | . | . | . | . | . | . | . | . | . | . | . |
| 139 | L_13 | N2C | . | . | . | . | . | . | . | . | . | . | . | . | . | . | . | . | . | . | . | . | . | . | . | . | . | . | . | . | . | . |
| 140 | L_19 | N3C | . | . | . | . | . | . | . | . | . | . | . | . | . | . | . | . | . | . | . | . | . | . | . | . | . | . | . | . | . | . |
| 141 | T_01 | N3C | . | . | . | . | . | . | . | . | . | . | . | . | D | . | . | . | . | . | . | . | . | . | . | . | . | . | . | . | . | . |
| 142 | T_02 | N3C | . | . | . | . | . | . | . | . | . | V | . | . | . | . | . | . | . | . | . | . | . | . | . | . | . | . | . | . | . | . |
| 143 | T_07 | N3C | . | . | . | . | . | . | . | . | . | . | . | . | . | . | . | . | . | . | . | . | . | . | . | . | . | . | . | . | . | . |
| 144 | T_08 | N3C | . | . | . | . | . | . | . | . | . | . | . | . | . | . | . | . | . | . | . | . | . | . | . | . | . | . | . | . | . | . |
| 145 | T_09 | N3C | . | . | . | . | . | . | . | . | . | . | . | . | . | . | S | . | . | . | . | . | . | . | . | . | . | . | . | . | . | . |
| 146 | T_16 | N3C | . | . | . | . | . | P | . | . | . | . | . | . | . | . | . | . | . | . | . | . | . | . | . | . | . | . | . | . | . | . |
| 147 | T_25 | N3C | . | . | . | . | . | . | . | . | . | . | . | . | . | . | . | . | . | . | . | . | . | . | . | . | . | . | . | . | . | . |
| 148 | T_27 | N3C | . | . | . | . | . | P | . | . | . | . | . | . | . | . | . | . | . | . | . | . | . | . | . | . | . | . | . | . | . | . |
| 149 | T_37 | N3C | . | . | . | . | . | . | . | . | . | . | . | . | . | . | . | . | . | . | . | . | . | . | . | . | . | . | . | . | . | . |
| 150 | T_40 | N3C | . | . | . | . | . | . | . | . | . | . | . | . | . | . | S | . | . | . | . | . | . | . | . | . | . | . | . | . | . | . |

FIG. 21B

| SEQ ID NO. | Clone | NxC | x | D | x | x | G | x | T | P | L | H | L | A | A | x | x | G | H | L | E | I | V | E | V | L | L | K | z | G | A | D | V | N | A |
|---|---|---|---|---|---|---|---|---|---|---|---|---|---|---|---|---|---|---|---|---|---|---|---|---|---|---|---|---|---|---|---|---|---|---|---|
| 151 | | | | | | | | | T | P | L | H | L | A | A | | | G | H | L | E | I | V | E | V | L | L | K | | G | A | D | V | N | A |
| 120 | E_01 | N3C | D | | T | W | | W | | | | | | | | Y | Q | | | | | | | | | | | | N | | | | | | |
| 121 | E_67 | N3C | T | | N | D | | N | | | | | | S | | W | I | | | | | | | | | | | | H | | | | | | |
| 122 | E_68 | N3C | F | | Y | W | | M | | | | | | | | D | N | | | | | | | | | | | | H | | | | | | |
| 123 | E_69 | N4C | D | | N | A | | R | | | | | | | | N | F | | | | | | | | | | | | N | | | | | | |
| 124 | 9_16 | N3C | H | | F | H | | L | | | | | | | | G | M | | | | | | | | | | | | N | | | | | | |
| 125 | 9_26 | N3C | K | | F | Y | | I | | | | | | | | A | Y | | | | | | | | | | | | H | | | | | | |
| 126 | 9_29 | N3C | H | | F | Y | | I | | | | | | | | N | F | | | | | | | | | | | | H | | | | | | |
| 127 | H_14 | N3C | T | | I | H | | H | | | | | | | | A | M | | | | | | | | | | | | N | | | | | | |
| 128 | B4_01 | N4C | V | | W | M | | D | | | | | | | | F | Y | | | | | | | | | | | | N | | | | | | |
| 129 | B4_02 | N3C | K | | N | A | | K | | A | | | | | | V | W | | | | | | | | | | | | N | | | | | | |
| 130 | B4_07 | N3C | R | | V | F | | W | | | | | | | | V | D | | | | | | | | | | | | Y | | | | | | |
| 131 | B4_33 | N3C | E | | A | T | | F | | | | | | | | V | W | | | | | | | | | | | | N | | | | | | |
| 132 | B4_45 | N3C | R | | D | G | | T | | | | | | | | N | H | | | | | | | | | | | | Y | | | | | | |
| 133 | B4_50 | N4C | H | | R | Y | | V | | | | | | | | Y | F | | | | | | | | | | | | N | | | | | | |
| 134 | B4_58 | N5C | F | | S | N | | I | | | | | | | | F | F | | | | | | | | | | | | N | | | | | | |
| 135 | L_01 | N3C | N | | I | S | | Y | | | | | | | | Y | V | | | Q | | | | | | | | | | N | | | | | | |
| 136 | L_02 | N2C | R | | M | S | | Y | | | | | | | | H | M | | | | | | | | | | | | N | | | | | | |
| 137 | L_07 | N2C | S | | K | S | | Y | | | | | | | | H | I | | | | | | | | | | | | H | | | | | | |
| 138 | L_11 | N3C | I | | T | I | | L | | | | | | | | H | D | | | | | | | | | | | | N | | | | | | |
| 139 | L_13 | N2C | F | | M | S | | Y | | | | | | | | Y | D | | | | | | | | | | | | N | | | | | | |
| 140 | L_19 | N3C | D | | N | K | | D | | | | | | | | S | F | | | | | | | | | | | | N | | | | | | |
| 141 | T_01 | N3C | N | | I | W | | I | | | | | | | | I | F | | | | | | | | | F | | | | N | | | | | | |
| 142 | T_02 | N3C | A | | H | Q | S | F | | | | | Y | | | I | F | | | | | | | | | | | | | N | | | | | | |
| 143 | T_07 | N3C | Y | | W | K | | L | | | | | | | | I | F | | | | | | | | S | A | M | | | N | | | | | | |
| 144 | T_08 | N3C | W | | F | L | | L | I | | R | | | | | A | F | | | | | | | | | | | | | N | | | | | | |
| 145 | T_09 | N3C | N | | F | Q | | I | | | | | | | | I | F | | | | | | | | | | | | | N | | | | | | |
| 146 | T_16 | N3C | Y | | I | V | | I | | | | | | | | I | F | | | | | | | | | | | | | N | | | | | | |
| 147 | T_25 | N3C | D | | R | R | | I | P | | | | | | | I | F | | | | | | | | | | | | | H | | | | | | |
| 148 | T_27 | N3C | Y | | R | H | | L | | | | | V | | | I | F | | | | | | | | | | | | | H | | | | | | |
| 149 | T_37 | N3C | H | | K | R | | I | | | | | | | | I | T | | | | M | | | | | | | | | H | | | | | | |
| 150 | T_40 | N3C | N | | R | V | | F | | | | | | | | M | F | | | | L | | | | | | | | | N | | | | | | |

FIG. 21C

| SEQ ID NO. | Clone | NxC | 2. repeat 1 | | | | 5 | | | | | 10 | | | | | 15 | | | | | 20 | | | | | 25 | | | | | 30 | |
|---|---|---|---|---|---|---|---|---|---|---|---|---|---|---|---|---|---|---|---|---|---|---|---|---|---|---|---|---|---|---|---|---|---|
| 151 | Clone | NxC | x | D | x | x | G | x | T | P | L | H | L | A | A | x | x | G | H | L | E | I | V | E | V | L | L | K | z | G | A | D | V | N | A |
| 120 | E_01 | N3C | Y | , | Y | I | . | W | . | . | . | . | . | . | . | D | . | . | . | . | . | . | . | . | . | . | . | . | N | . | . | . | . | . | . |
| 121 | E_67 | N3C | D | . | L | L | . | M | . | . | . | . | . | . | . | D | T | . | . | . | . | . | . | . | . | . | . | . | Y | . | . | . | . | . | . |
| 122 | E_68 | N3C | S | , | N | F | . | F | . | . | . | . | . | . | . | F | Y | . | . | . | . | . | . | . | . | . | . | . | H | . | . | . | . | . | . |
| 123 | E_69 | N4C | K | G | H | H | C | N | . | . | . | . | . | . | . | W | A | . | . | . | . | . | . | . | . | . | . | . | Y | . | . | . | . | . | . |
| 124 | 9_16 | N3C | V | , | T | D | . | I | . | L | . | . | . | . | . | Y | Y | . | . | . | . | . | . | . | . | . | . | . | H | . | . | . | . | . | . |
| 125 | 9_26 | N3C | H | . | W | N | . | W | . | . | . | . | . | . | . | K | Y | . | . | . | . | . | . | . | . | . | . | . | H | . | . | . | . | . | . |
| 126 | 9_29 | N3C | F | , | Y | . | D | N | . | . | . | . | . | . | . | D | A | . | . | . | . | . | . | . | . | . | . | . | Y | . | . | . | . | . | . |
| 127 | H_14 | N3C | N | . | W | R | . | F | . | . | . | . | . | . | . | L | N | . | . | . | . | . | . | . | . | . | . | . | N | . | . | . | . | . | . |
| 128 | B4_01 | N4C | K | . | T | W | . | D | . | . | . | . | . | . | . | L | L | . | R | . | . | . | . | . | . | . | . | . | H | . | . | . | . | . | . |
| 129 | B4_02 | N3C | Y | , | A | S | . | Y | . | L | . | . | . | . | . | R | M | . | . | . | . | . | . | . | . | . | . | . | Y | . | . | . | . | . | . |
| 130 | B4_07 | N3C | R | , | V | A | . | R | . | . | . | . | . | . | . | S | F | . | . | . | . | . | . | . | . | . | . | . | Y | . | . | . | . | . | . |
| 131 | B4_33 | N3C | N | . | Q | Y | . | Y | . | . | . | . | . | . | . | R | M | . | . | . | . | . | . | . | . | . | . | . | H | . | . | . | . | . | . |
| 132 | B4_45 | N3C | N | . | R | Y | . | Y | . | T | . | . | . | . | . | R | H | . | . | . | . | . | . | . | . | . | . | . | H | . | . | . | . | . | . |
| 133 | B4_50 | N4C | D | . | H | D | . | Y | . | . | . | . | . | . | . | D | K | . | . | . | . | . | . | . | . | . | . | . | H | . | . | . | . | . | . |
| 134 | B4_58 | N5C | H | . | S | Y | . | S | . | . | . | . | . | . | . | N | R | . | . | . | . | . | . | . | . | . | . | . | Y | . | . | . | . | . | . |
| 135 | L_01 | N3C | D | . | T | W | . | D | . | . | . | . | . | . | . | L | F | . | . | . | . | . | . | . | . | . | . | . | Y | . | . | . | . | . | . |
| 136 | L_02 | N2C | K | . | N | W | . | D | . | . | . | . | . | . | . | I | F | . | . | . | . | . | . | . | . | . | . | . | N | . | . | . | . | . | . |
| 137 | L_07 | N2C | H | , | S | W | . | D | . | . | . | . | . | . | . | T | F | . | . | . | . | . | . | . | . | . | . | . | H | . | . | . | . | . | . |
| 138 | L_11 | N3C | A | . | N | W | . | I | . | . | . | . | . | . | . | R | R | . | . | . | . | . | . | . | . | . | . | . | H | . | . | . | . | . | . |
| 139 | L_13 | N2C | N | . | L | W | . | D | . | . | . | . | . | . | . | T | R | . | . | . | . | . | . | . | . | . | . | . | Y | . | . | . | . | . | . |
| 140 | L_19 | N3C | D | . | Y | F | . | D | . | . | . | . | . | . | . | W | S | . | . | . | . | . | . | . | . | . | . | . | Y | . | . | . | . | . | . |
| 141 | T_01 | N3C | S | . | F | S | . | F | . | . | . | . | . | . | . | Y | K | . | . | . | . | . | . | . | . | . | . | . | H | . | . | . | . | . | . |
| 142 | T_02 | N3C | S | . | W | H | . | N | . | . | . | . | . | . | . | W | I | . | . | . | . | . | . | . | . | . | . | . | Y | . | . | . | . | . | . |
| 143 | T_07 | N3C | I | . | F | S | . | R | . | . | . | . | . | . | . | L | I | . | . | . | . | . | . | . | . | . | . | . | Y | . | . | . | . | . | . |
| 144 | T_08 | N3C | K | . | T | Y | . | I | . | . | . | . | . | . | . | M | N | . | . | . | . | . | . | . | . | . | . | . | N | . | . | . | . | . | . |
| 145 | T_09 | N3C | Y | . | Q | M | . | M | . | . | . | . | . | . | . | W | T | . | . | . | . | . | . | . | . | . | . | . | H | . | . | . | . | . | . |
| 146 | T_16 | N3C | Y | . | M | Q | V | N | . | . | . | . | . | . | . | W | L | . | . | . | . | . | . | . | . | . | . | . | N | . | . | . | . | . | . |
| 147 | T_25 | N3C | H | . | M | Q | . | R | . | . | . | . | . | . | . | Y | T | . | . | . | . | . | . | . | . | . | . | . | Y | . | . | . | . | . | . |
| 148 | T_27 | N3C | I | , | I | I | . | Y | . | . | . | . | . | . | . | W | S | . | . | . | . | . | . | . | . | . | . | . | N | . | . | . | . | . | . |
| 149 | T_37 | N3C | V | . | I | Q | . | R | . | . | . | . | . | . | . | W | I | . | . | . | . | . | . | . | . | . | . | . | Y | . | . | . | . | . | . |
| 150 | T_40 | N3C | I | . | F | Q | . | K | . | . | . | . | . | . | . | Q | L | . | . | . | . | . | . | . | . | . | . | . | Y | . | . | . | . | . | . |

FIG. 21D

| SEQ ID NO. | Clone | NxC | | | | | | 3. repeat | | | | | | | | | | | | | | | | | | | | |
|---|---|---|---|---|---|---|---|---|---|---|---|---|---|---|---|---|---|---|---|---|---|---|---|---|---|---|---|---|
| 151 | Clone | NxC | x | D | x | x | G | x | T P L H L A A | x | x | G H L E I V E V L L K | z | G A D V N A |
| 120 | E_01 | N3C | S | . | Y I | . | D | . | . . . . . . . | H | N | . . . . . . . . . . . | H | . . . . . . |
| 121 | E_67 | N3C | R | . | T R | . | K | . | . . . . . . . | R | D | . . . . . . . . . . . | H | D . . . . |
| 122 | E_68 | N3C | F | . | M W | . | N | . | . . . . . . . | Q | N | . . . . . . . . . . . | N | . . . . . . |
| 123 | E_69 | N4C | D | . | D E | . | Y | . | . . . . . . . | D | I | . D . . . . . . . . . | Y | . . . . . . |
| 124 | 9_16 | N3C | H | . | Y A | . | S | . | . . . . . . . | N | T | . . . . . . . . . . . | N | . . . . . . |
| 125 | 9_26 | N3C | I | . | N A | . | K | . | . . . . . . . | A | H | . . . . . . . . . . . | Y | . . . . . . |
| 126 | 9_39 | N3C | S | . | R D | . | H | . | . . . . . . . | R | E | . . . . . . . . . . . | N | . . . . . . |
| 127 | H_14 | N3C | T | . | T A | . | N | . | . . . . . . . | W | F | . . . . . . . . . . . | N | . . . . . . |
| 128 | B4_01 | N4C | I | . | M R | . | T | . | . . . . . . . | P | A | . . . . . . . . . . . | Y | . . . . . . |
| 129 | B4_02 | N3C | R | . | R F | . | S | . | . . . . . . . | W | H | . . . . . . . . . . . | H | . . . . . . |
| 130 | B4_07 | N3C | V | . | Y T | . | T | . | . . . . . . . | W | H | . . . . . . . . . . . | H | . . . . . . |
| 131 | B4_33 | N3C | I | . | V L | . | T | . | . . . . . . . | W | H | . . . . . . . . . . . | N | . . . . . . |
| 132 | B4_45 | N3C | F | . | N T | . | Q | . | . . . . . . . | W | H | . . . . . . . . . . . | Y | . . . . . . |
| 133 | B4_50 | N4C | D | . | S M | . | N | . | . . . . . . . | R | H | . . . . . . . . . . . | H | . . . . . . |
| 134 | B4_58 | N3C | F | . | S T | . | Q | . | . . . . . . . | S | Q | . . . . . . . . . . . | Y | . . . . . . |
| 135 | L_01 | N3C | H | . | R F | . | F | . | . . . . . . . | S | S | . . . . . . . . . . . | H | . . . . . . |
| 136 | L_02 | N2C | | | | | | | | | | | | |
| 137 | L_07 | N2C | | | | | | | | | | | | |
| 138 | L_11 | N3C | D | . | V Q | . | N | . | . . . . . T . | H | H | . . . . . . . . . . . | H | . . . . . . |
| 139 | L_13 | N2C | | | | | | | | | | | | |
| 140 | L_19 | N3C | Q | . | Q R | . | F | . | . . . . . . . | I | A | . . . . . . . . . . . | Y | . . . . . . |
| 141 | T_01 | N3C | N | . | A T | . | T | . | . . . . . . . | K | K | . . . . . . . . . . . | N | . . . . . . |
| 142 | T_02 | N3C | T | . | H S | . | S | . | . . . . . . . | T | L | . . . . . . . . . . . | Y | . . . . . . |
| 143 | T_07 | N3C | H | . | S A | . | S | . | . . . . . . . | T | K | . . . . . . . . . . . | Y | . . . . . . |
| 144 | T_08 | N3C | L | . | N T | . | S | . | . . . . . . . | N | Y | . . . . . . . . . . . | H | . . . . . . |
| 145 | T_09 | N3C | D | . | T H | . | A | . | . . . . . . . | H | T | . . . . . . . . . . . | Y | . . . . . . |
| 146 | T_16 | N3C | E | . | S Y | . | N | . | . . . . . . . | D | K | . . . . . . . . . . . | N | . . . . . . |
| 147 | T_25 | N3C | I | . | F T | . | H | . | . . . . . . . | F | R | . . . . . . . . . . . | H | . . . . . . |
| 148 | T_27 | N3C | S | . | V T | . | S | . | . . . . . . . | D | K | . . . . . . . . . . . | Y | . . . . . . |
| 149 | T_37 | N2C | M | . | D F | . | E | . | . . . . . . . | R | T | . . . . . . . . . . . | H | . . . . . . |
| 150 | T_40 | N3C | L | . | A R | . | I | . | . . . . . . . | I | H | . P . . . . . . . . . | Y | . . . . . . |

FIG. 21E

| SEQ ID NO. | Clone | NxC | 4. repeat |   |   |   |   |   |   |   |   |   |   |   |   |   |   |   |   |   |   |   |   |   |   |   |   |   |   |   |
|---|---|---|---|---|---|---|---|---|---|---|---|---|---|---|---|---|---|---|---|---|---|---|---|---|---|---|---|---|---|---|
|   |   |   | x | D | x | x | G | x | T | P | L | H | L | A | A | x | x | G | H | L | E | I | V | E | V | L | L | K | z | G A D V N A |
| 151 |  |  |   |   |   |   |   |   |   |   |   |   |   |   |   |   |   |   |   |   |   |   |   |   |   |   |   |   |   |   |
| 120 | E_01 | N3C |   |   |   |   |   |   |   |   |   |   |   |   |   |   |   |   |   |   |   |   |   |   |   |   |   |   |   |   |   |
| 121 | E_67 | N3C |   |   |   |   |   |   |   |   |   |   |   |   |   |   |   |   |   |   |   |   |   |   |   |   |   |   |   |   |   |
| 122 | E_68 | N3C |   |   |   |   |   |   |   |   |   |   |   |   |   |   |   |   |   |   |   |   |   |   |   |   |   |   |   |   |   |
| 123 | E_69 | N4C | W |   | M | Y |   | R |   |   |   |   |   |   |   |   | S | A |   |   |   |   |   |   |   |   |   |   | Y |   |   |
| 124 | 9_16 | N3C |   |   |   |   |   |   |   |   |   |   |   |   |   |   |   |   |   |   |   |   |   |   |   |   |   |   |   |   |   |
| 125 | 9_26 | N3C |   |   |   |   |   |   |   |   |   |   |   |   |   |   |   |   |   |   |   |   |   |   |   |   |   |   |   |   |   |
| 126 | 9_29 | N3C |   |   |   |   |   |   |   |   |   |   |   |   |   |   |   |   |   |   |   |   |   |   |   |   |   |   |   |   |   |
| 127 | H_14 | N3C |   |   |   |   |   |   |   |   |   |   |   |   |   |   |   |   |   |   |   |   |   |   |   |   |   |   |   |   |   |
| 128 | B4_01 | N4C | D |   | V | H |   | N |   |   |   |   |   |   |   |   | M | S |   |   |   |   |   |   |   |   |   |   | Y |   |   |
| 129 | B4_02 | N3C |   |   |   |   |   |   |   |   |   |   |   |   |   |   |   |   |   |   |   |   |   |   |   |   |   |   |   |   |   |
| 130 | B4_07 | N3C |   |   |   |   |   |   |   |   |   |   |   |   |   |   |   |   |   |   |   |   |   |   |   |   |   |   |   |   |   |
| 131 | B4_33 | N3C |   |   |   |   |   |   |   |   |   |   |   |   |   |   |   |   |   |   |   |   |   |   |   |   |   |   |   |   |   |
| 132 | B4_45 | N3C |   |   |   |   |   |   |   |   |   |   |   |   |   |   |   |   |   |   |   |   |   |   |   |   |   |   |   |   |   |
| 133 | B4_50 | N4C | N |   | F | M |   | S |   |   |   |   |   |   |   |   | W | S |   |   |   |   |   |   |   |   |   |   | H |   |   |
| 134 | B4_58 | N5C | S |   | R | M |   | F |   |   |   |   |   |   |   |   | Y | T |   |   |   |   |   |   |   |   |   |   | N |   |   |
| 135 | L_01 | N3C |   |   |   |   |   |   |   |   |   |   |   |   |   |   |   |   |   |   |   |   |   |   |   |   |   |   |   |   |   |
| 136 | L_02 | N2C |   |   |   |   |   |   |   |   |   |   |   |   |   |   |   |   |   |   |   |   |   |   |   |   |   |   |   |   |   |
| 137 | L_07 | N2C |   |   |   |   |   |   |   |   |   |   |   |   |   |   |   |   |   |   |   |   |   |   |   |   |   |   |   |   |   |
| 138 | L_11 | N3C |   |   |   |   |   |   |   |   |   |   |   |   |   |   |   |   |   |   |   |   |   |   |   |   |   |   |   |   |   |
| 139 | L_13 | N2C |   |   |   |   |   |   |   |   |   |   |   |   |   |   |   |   |   |   |   |   |   |   |   |   |   |   |   |   |   |
| 140 | L_19 | N3C |   |   |   |   |   |   |   |   |   |   |   |   |   |   |   |   |   |   |   |   |   |   |   |   |   |   |   |   |   |
| 141 | T_01 | N3C |   |   |   |   |   |   |   |   |   |   |   |   |   |   |   |   |   |   |   |   |   |   |   |   |   |   |   |   |   |
| 142 | T_02 | N3C |   |   |   |   |   |   |   |   |   |   |   |   |   |   |   |   |   |   |   |   |   |   |   |   |   |   |   |   |   |
| 143 | T_07 | N3C |   |   |   |   |   |   |   |   |   |   |   |   |   |   |   |   |   |   |   |   |   |   |   |   |   |   |   |   |   |
| 144 | T_08 | N3C |   |   |   |   |   |   |   |   |   |   |   |   |   |   |   |   |   |   |   |   |   |   |   |   |   |   |   |   |   |
| 145 | T_09 | N3C |   |   |   |   |   |   |   |   |   |   |   |   |   |   |   |   |   |   |   |   |   |   |   |   |   |   |   |   |   |
| 146 | T_16 | N3C |   |   |   |   |   |   |   |   |   |   |   |   |   |   |   |   |   |   |   |   |   |   |   |   |   |   |   |   |   |
| 147 | T_25 | N3C |   |   |   |   |   |   |   |   |   |   |   |   |   |   |   |   |   |   |   |   |   |   |   |   |   |   |   |   |   |
| 148 | T_27 | N3C |   |   |   |   |   |   |   |   |   |   |   |   |   |   |   |   |   |   |   |   |   |   |   |   |   |   |   |   |   |
| 149 | T_37 | N3C |   |   |   |   |   |   |   |   |   |   |   |   |   |   |   |   |   |   |   |   |   |   |   |   |   |   |   |   |   |
| 150 | T_40 | N3C |   |   |   |   |   |   |   |   |   |   |   |   |   |   |   |   |   |   |   |   |   |   |   |   |   |   |   |   |   |

FIG. 21F

| SEQ ID NO. | | | | | | | | | 5. repeat | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|
| 151 | Clone | NxC | x | D | x | x | G | x | T | P | L | H | L | A | A | x | x | G | H | L | E | I | V | E | V | L | L | K | z | G | A | D | V | N | A |
| 120 | E_01 | N3C | | | | | | | | | | | | | | | | | | | | | | | | | | | | | | | | |
| 121 | E_67 | N3C | | | | | | | | | | | | | | | | | | | | | | | | | | | | | | | | |
| 122 | E_68 | N3C | | | | | | | | | | | | | | | | | | | | | | | | | | | | | | | | |
| 123 | E_69 | N4C | | | | | | | | | | | | | | | | | | | | | | | | | | | | | | | | |
| 124 | 9_16 | N3C | | | | | | | | | | | | | | | | | | | | | | | | | | | | | | | | |
| 125 | 9_26 | N3C | | | | | | | | | | | | | | | | | | | | | | | | | | | | | | | | |
| 126 | 9_29 | N3C | | | | | | | | | | | | | | | | | | | | | | | | | | | | | | | | |
| 127 | H_14 | N3C | | | | | | | | | | | | | | | | | | | | | | | | | | | | | | | | |
| 128 | B4_01 | N4C | | | | | | | | | | | | | | | | | | | | | | | | | | | | | | | | |
| 129 | B4_02 | N3C | | | | | | | | | | | | | | | | | | | | | | | | | | | | | | | | |
| 130 | B4_07 | N3C | | | | | | | | | | | | | | | | | | | | | | | | | | | | | | | | |
| 131 | B4_33 | N3C | | | | | | | | | | | | | | | | | | | | | | | | | | | | | | | | |
| 132 | B4_45 | N3C | | | | | | | | | | | | | | | | | | | | | | | | | | | | | | | | |
| 133 | B4_50 | N4C | | | | | | | | | | | | | | | | | | | | | | | | | | | | | | | | |
| 134 | B4_58 | N5C | K | . | F | V | . | W | . | . | . | . | . | . | . | . | . | Y | R | . | . | . | . | . | . | . | . | . | H | . | . | . | . | . |
| 135 | L_01 | N3C | | | | | | | | | | | | | | | | | | | | | | | | | | | | | | | | |
| 136 | L_02 | N2C | | | | | | | | | | | | | | | | | | | | | | | | | | | | | | | | |
| 137 | L_07 | N2C | | | | | | | | | | | | | | | | | | | | | | | | | | | | | | | | |
| 138 | L_11 | N3C | | | | | | | | | | | | | | | | | | | | | | | | | | | | | | | | |
| 139 | L_13 | N2C | | | | | | | | | | | | | | | | | | | | | | | | | | | | | | | | |
| 140 | L_19 | N3C | | | | | | | | | | | | | | | | | | | | | | | | | | | | | | | | |
| 141 | T_01 | N3C | | | | | | | | | | | | | | | | | | | | | | | | | | | | | | | | |
| 142 | T_02 | N3C | | | | | | | | | | | | | | | | | | | | | | | | | | | | | | | | |
| 143 | T_07 | N3C | | | | | | | | | | | | | | | | | | | | | | | | | | | | | | | | |
| 144 | T_08 | N3C | | | | | | | | | | | | | | | | | | | | | | | | | | | | | | | | |
| 145 | T_09 | N3C | | | | | | | | | | | | | | | | | | | | | | | | | | | | | | | | |
| 146 | T_16 | N3C | | | | | | | | | | | | | | | | | | | | | | | | | | | | | | | | |
| 147 | T_25 | N3C | | | | | | | | | | | | | | | | | | | | | | | | | | | | | | | | |
| 148 | T_27 | N3C | | | | | | | | | | | | | | | | | | | | | | | | | | | | | | | | |
| 149 | T_37 | N3C | | | | | | | | | | | | | | | | | | | | | | | | | | | | | | | | |
| 150 | T_40 | N3C | | | | | | | | | | | | | | | | | | | | | | | | | | | | | | | | |

FIG. 21G

| SEQ ID NO. | Clone | NxC | C-Cap<br>Q D K F G K T A F D I S I D N G N E D L A E I L Q |
|---|---|---|---|
| 151 | Clone | NxC | Q D K F G K T A F D I S I D N G N E D L A E I L Q |
| 120 | E_01 | N3C | . . . . . . . . . . . . . . . . . . . . . . . . . |
| 121 | E_67 | N3C | . . . . . . . . . . . . . . . . . . . . . . . . . |
| 122 | E_68 | N3C | . . . . . . . . . . . . . . . . . . . . . . . . . |
| 123 | E_69 | N4C | . . . . . . . . . . . . . . . . . . . . . . . . . |
| 124 | 9_16 | N3C | . . . . . . . . . . . . . . . . . . . . . . . . . |
| 125 | 9_26 | N3C | . . . . . . . . . . . . . . . . . . . . . . . . . |
| 126 | 9_29 | N3C | . . . . . . . . . . . . . . . . . . . . . . . . . |
| 127 | H_14 | N3C | . . . . . . . . . . . . . . . . . . . . . . . . . |
| 128 | B4_01 | N4C | . . . . . . . . . . . . . . . . . . . . . . . . . |
| 129 | B4_02 | N3C | . . . . . . . . . . . . . . . . . . . . . . . . . |
| 130 | B4_07 | N3C | . . . . . . . . . . . . . . . . . . . . . . . . . |
| 131 | B4_33 | N3C | . . . . . . . . . . . . . . . . . . . . . . . . . |
| 132 | B4_45 | N3C | . . . . . . . . . . . . . . . . . . . . . . . . . |
| 133 | B4_50 | N4C | . . . . . . . . . . . . . . . . . . . . . . . . . |
| 134 | B4_58 | N5C | . . . . . . . . . . . . . . . . . . . . . . . . . |
| 135 | L_01 | N3C | . . . . . . . . . . . . . . . . . . . . . . . . . |
| 136 | L_02 | N2C | . . . . . . . . . . . . . . . . . . . . . . . . . |
| 137 | L_07 | N2C | . . . . . . . . . . . . . . . . . . . . . . . . . |
| 138 | L_11 | N3C | . . . . . . . . . . . . . . . . . . . . . . . . . |
| 139 | L_13 | N2C | . . . . . . . . . . . . . . . . . . . . . . . . . |
| 140 | L_19 | N3C | . . . . . . . . . . . . . . . . . . . . . . . . . |
| 141 | T_01 | N3C | . . . . . . . . . . . . . . . . . . . . . . . . . |
| 142 | T_02 | N3C | . . . . . . . . . . . . . . . . . . . . . . . . . |
| 143 | T_07 | N3C | . . . . . . . . . . . . . . . . . . . . . . . . . |
| 144 | T_08 | N3C | . . . . . . . . . . . . . . . . . . . . . . . . . |
| 145 | T_09 | N3C | . . . . . . . . . . . . . . . . . . . . . . . . . |
| 146 | T_16 | N3C | . . . . . . . . . . . . . . . . . . . . . . . . . |
| 147 | T_25 | N3C | . . . . . . . . . . . . . . . . . . . . . . . . . |
| 148 | T_27 | N3C | . . . . . . . . . . . . . . . . . . . . . . . . . |
| 149 | T_37 | N3C | . . . . . . . . . . . . . . . . . . . . . . . . . |
| 150 | T_40 | N3C | . . . . . . . . . . . . . . . . . . . . . . . . . |

BISPECIFIC CHIMERIC PROTEINS COMPRISING DARPINS

CROSS-REFERENCE TO RELATED APPLICATIONS

This application claims the benefit of Korean Patent Application No. 10-2013-0089120 filed on Jul. 26, 2013 in the Korean Intellectual Property Office, the entire disclosure of which is hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: One 193,987 Byte ASCII (Text) file named "716952_ST25_revised2.0 ," created Oct. 16, 2015.

BACKGROUND

1. Field

The present disclosure relates to a bispecific chimeric protein including a designed ankyrin repeat protein (DARPin) and related methods and compositions.

2. Description of the Related Art

In living cells, various proteins interact with each other and participate in various disease-causing mechanisms. If at least two of such disease-causing proteins are simultaneously inhibited, there is a greater probability of treating and preventing disease compared to instances where a single protein is inhibited. For these reasons, various antibodies capable of inhibiting at least two proteins have been developed.

Although many bispecific antibodies have been developed, most of the bispecific antibodies cannot be commercialized as antibody medicaments, since their therapeutic effects are not clinically verified or various side effects fully observed. In addition, the developed bispecific antibodies have defects in stability and productivity, which is an obstacle in commercialization. The early developed bispecific antibodies having IgG form were difficult to isolate and purify, due to light chains and heavy chains being randomly combined during producing processes, leading to problems in large scale production. In addition, in the case of non-IgG bispecific antibodies, the stability as a medicine in respect of protein folding, pharmacokinetics, and the like has not been verified.

Therefore, there is a need for developing a bispecific chimeric protein having increased stability in living body and improved properties as a medicine.

SUMMARY

Provided is a bispecific chimeric protein (i.e., bispecific antibody conjugate) including an antibody (e.g., IgG antibody) and/or an antibody fragment (e.g., ScFv-Fc antibody fragment) and a designed ankyrin repeat protein (DARPin) linked thereto, and a pharmaceutical composition comprising the antibody and a pharmaceutically acceptable carrier. The bispecific chimeric protein can be useful as a bispecific antibody.

Also provided is a method of preparing the bispecific chimeric protein by linking a DARPin to an antibody (e.g., IgG antibody) and/or an antibody fragment (e.g., ScFv-Fc antibody fragment), or by expressing a nucleic acid encoding the bispecific chimeric protein in a cell.

Further provided is a method of treating or preventing cancer in a subject comprising administering the bispecific chimeric protein to a subject in need of the treatment or prevention of cancer.

Related compositions and methods also are provided, as will be apparent from the following detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 21A is a chart displaying nucleotide sequences of various DARPins.

FIG. 21B is a chart displaying nucleotide sequences of various DARPins.

FIG. 21C is a chart displaying nucleotide sequences of various DARPins.

FIG. 21D is a chart displaying nucleotide sequences of various DARPins.

FIG. 21E is a chart displaying nucleotide sequences of various DARPins.

FIG. 21F is a chart displaying nucleotide sequences of various DARPins.

FIG. 21G is a chart displaying nucleotide sequences of various DARPins.

DETAILED DESCRIPTION

Figure 1:
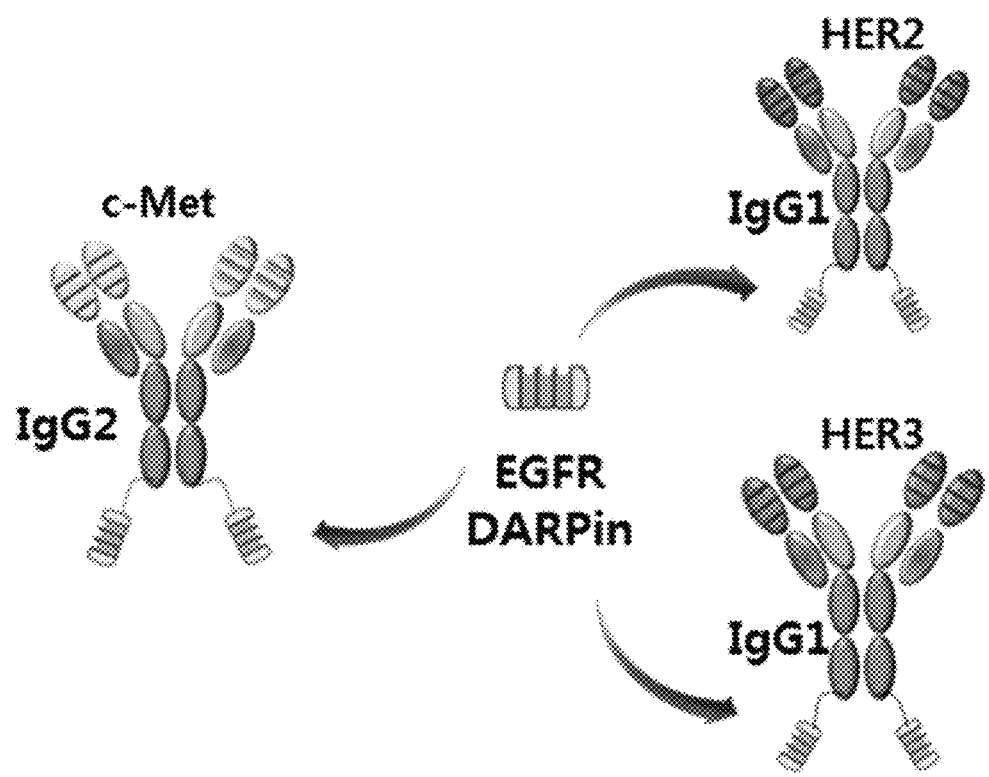
FIG. 1 is a schematic depicting processes of preparing various bispecific chimeric proteins using an anti-EGFR DARPin according to an embodiment.

Bispecific antibodies have been developed in various kinds and forms and are expected to possess excellent therapeutic effects compared to pre-existing monoclonal antibodies, due to their ability to bind to at least two antigens. Herein, a bispecific chimeric protein is provided by binding a DARPin to an IgG antibody or fragment thereof.

DARPin (designed ankyrin repeat protein; see Chapter 5. "Designed Ankyrin Repeat Proteins (DARPins): From Research to Therapy", Methods in Enzymology, vol 503: 101~134 (2012); and "Efficient Selection of DARPins with Sub-nanomolar Affinities using SRP Phage Display", J. *Mol. Biol.* (2008) 382, 1211-1227, the entire disclosures of which are hereby incorporated by reference) refers to an antibody mimetic protein having high specificity and high binding affinity to a target protein, which is prepared via genetic engineering. DARPin is originated from natural ankyrin protein, and has a structure comprising at least 2 ankyrin repeat motifs, for example, comprising at least 3, 4 or 5 ankyrin repeat motifs. The DARPin can have any suitable molecular weight depending on the number of repeat motifs. For example, the DARPins including 3, 4 or 5 ankyrin repeat motifs may have a molecular weight of about 10 kDa, about 14 kDa, or about 18 kDa, respectively.

DARPin includes a core part that provides structure and a target binding portion that resides outside of the core and binds to a target. The structural core includes a conserved amino acid sequence and the target binding portion includes an amino acid sequence that differs depending on the target.

Examples of DARPins are summarized in the following table and the nucleotide sequences thereof are illustrated in FIGS. 21A to 21G:

| Target protein | DARPins |
|---|---|
| Human IgG1-Fc | I_01/02/07/11/13/19 |
| TNF-alpha | T_01/02/07/08/09/16/25/27/37/40 |
| ErbB1 (EGFR) | E_01/67/68/69 |
| ErbB2 (1-509) | 9_16/26/29 |
| ErbB2 (1-631) | H_14 |
| ErbB4 | B4_01/02/07/33/45/50/58 |
| CitS | cp34_15/16 |

A DARPin has target specificity similar to an antibody. Thus, a new form of a bispecific chimeric protein is provided by attaching DARPin to an antibody or antibody fragment, such as an IgG (e.g., IgG1, IgG2, IgG3 or IgG4) antibody, or an scFv-Fc antibody fragment, or the like.

One embodiment provides a bispecific chimeric protein including (a) DARPin and (b) an antibody (e.g., IgG antibody), an antibody fragment (e.g., scFv-Fc antibody fragment), or a combination thereof. Another embodiment provides a method of preparing a bispecific chimeric protein by binding (a) DARPin to (b) an antibody (e.g., IgG antibody), an antibody fragment (e.g., scFv-Fc antibody fragment), or a combination thereof, or expressing a nucleic acid encoding the bispecific chimeric protein in a cell. The binding step may be carried out ex vivo.

In the bispecific chimeric protein, the targets (antigens) of DARPin and the antibody or antibody fragment may be the same (in this case the recognition sites are different) or different from each other. Accordingly, the bispecific chimeric protein can be used to target different antigens or different recognition sites (i.e., epitopes) of the same antigen.

The antibody may be any subtype of immunoglobulin (e.g., IgA, IgD, IgE, IgG (IgG1, IgG2, IgG3, IgG4), IgM, etc.).

The IgG antibody may be of an IgG1, IgG2, IgG3 or IgG4 subtype of a mammal, for example, IgG1 or IgG2 subtype. The IgG antibody includes two heavy chains and two light chains, and the heavy chain and the light chain are linked to each other via disulfide bonds, forming two heavy chain-light chain structures. The heavy chain-light chain structures are linked to each other at Fc region of the heavy chain via disulfide bond. The antibody having an IgG form may be a monospecific antibody targeting a single antigen (single targeting antibody) which includes an antigen-binding region for the same antigen at both of the two heavy chain-light chain structures; or a an antibody capable of targeting two antigens (dual targeting antibody) which includes antigen-binding regions for different antigens respectively at each of the two heavy chain-light chain structures.

The antibody having a scFv-Fc form may be a monospecific antibody in a monomeric form for targeting a single antigen, which includes one scFv-Fc fragment including an antigen-binding region for one antigen; a monospecific antibody in a dimeric form for targeting a single antigen, which includes two scFv-Fc fragments including antigen-binding regions for the same antigen, where the two scFv-Fc fragments are linked to each other at Fc region; or an antibody in a dimeric form that is capable of targeting two antigens, which includes two scFv-Fc fragments including antigen-binding regions for different antigens from each other, where the two scFv-Fc fragments are linked to each other at Fc region. The Fc region may be derived from subtype IgG1, IgG2, IgG3 or IgG4 of a mammal, for example, IgG1 or IgG2, specifically, human IgG1 or human IgG2.

When the antibody having an IgG form or a scFv-Fc form is capable of targeting two antigens, one of the two antigens to be targeted thereby may be the same with the target of DARPin.

The term "antigen-binding region" (e.g., paratope) may refer to a polypeptide including a fragment that specifically binds to an antigen, and for example, refer to a heavy chain CDR (complementarity determining region), a light chain CDR, a heavy chain variable region, a light chain variable region, or a combination thereof (for e.g., scFv, (scFv)2, Fab, Fab', or F(ab')2).

In addition, the DARPin may be linked to the C-terminus, N-terminus, both termini, or any other linkable site of the antibody having an IgG form or a scFv-Fc form. For example, in order to preserve antigen binding ability of the antibody having an IgG form or a scFv-Fc form, the DARPin may linked to C-terminus of Fc region of the antibody having an IgG form or a scFv-Fc form, but not be limited thereto.

If the bispecific chimeric protein includes a DARPin and a combination of an antibody having an IgG form and an antibody having a scFv-Fc form, the DARPin, the antibody having an IgG form and the antibody having a scFv-Fc form may be linked in any order. Although in some cases, the efficacy or expression rate of the bispecific chimeric protein may depend on the linking order, in general cases, the linking order has no effect on the desired efficacy of the bispecific chimeric protein. For example, the bispecific chimeric protein may include an antibody having an IgG form, a DARPin linked to C-terminus of the antibody having an IgG form, and an antibody having a scFv-Fc form linked to C-terminus of the DARPin, but not be limited thereto.

The bispecific chimeric protein may include at least one DARPin, for example, about 1 to about 10, about 1 to about 5, or about 1 to about 3 DARPins, which include the same amino acid sequence, or at least two kinds of DARPins, for example, about 2 to about 10, about 2 to about 5, or about 2 to about 3 kinds of DARPins, which include different amino acid sequences and target the same or different antigens. When at least two DARPins or at least two kinds of DARPins are included, the at least two DARPins or the at least two kinds of DARPins may be linked to each other (e.g., to provide a repeated form of DARPin) and then linked to the antibody (having an IgG form or a scFv-Fc form). The DARPins may be linked to at least one of C-terminus, N-terminus, and other linkable site of each chain of the antibody having an IgG form or a scFv-Fc form.

The bispecific chimeric protein may further include at least one kind of antigen-binding fragment, for example, 1 to 5 or 1 to 3 kinds of antigen-binding fragments targeting the same or different antigen from that of the DARPin and the IgG antibody or scFv-Fc antibody fragment. The additional antigen-binding fragment may be a heavy chain CDR, a light chain CDR, a heavy chain variable region, a light chain variable region, or a combination thereof (e.g., scFv, (scFv)2, Fab, Fab', or F(ab')2, and linked to any linkable site of the bispecific chimeric protein, for example, C-terminus of the heavy chain (e.g., Fc region) or C-terminus of the light chain of the antibody having an IgG form and/or a scFv-Fc form, or C-terminus of the DARPin.

A DARPin and an antibody in an IgG form and/or in a scFv-Fc form; a heavy chain variable region and a light chain variable region in the scFv-Fc; a scFv-Fc and a scFv-Fc (in case of forming a dimer); and an antigen binding fragment, a DARPin, and an antibody in an IgG form and/or in a scFv-Fc form may be linked to each other with or without a linker. The linker may be a peptide liker, and if two or more linkers are used, the linkers may be the same with or different from each other. The peptide linker may include 1 to 100 or 2 to 50 (e.g., 5 to 25, 1 to 10, or 2 to 5) amino acids, and the kinds of the amino acids included in the peptide linker may not have any limitation. For example, the peptide linker may include Gly, Asn and/or Ser residues, or may include neutral amino acids such as Thr and/or Ala. Amino acid sequences suitable for a peptide linker may be well known in the relevant art. The length of the peptide linker may be properly determined so that there is no negative effect on the function of the bispecific chimeric protein. For example, the peptide linker may include at least one amino acid selected from the group consisting of Gly, Asn, Ser, Thr, and Ala, wherein the total number of the amino acids in the linker may be 1 to 100, 2 to 50, or 5 to 25. One embodiment, the peptide linker may be represented as (GGGGS)n, wherein "n" an integer from 1 to 10) (e.g., an integer from 2 to 5).

Since the DARPin has high affinity to an antigen (target), and higher stability and smaller molecular weight than many types of antibody fragments (e.g., scFv, Fab, etc.), the DARPin has advantageous properties (such as pharmacokinetic (PK) properties in the living body) and stability in the living body. In addition, the DARPin can be readily fused with other proteins. Therefore, the DARPin can be useful in preparing a bispecific chimeric protein having excellent properties and stability in the body.

"EGFR (epidermal growth factor receptor)" is a member of the receptor tyrosine kinases (RTKs) of HER family. Overexpression, gene amplification, mutation, or rearrangement of EGFR are frequently observed in several human malignant tumors and are related to poor prognosis of cancer treatment and bad clinical outcomes. For such reasons, the EGFR becomes an important target in anticancer therapy.

In an embodiment, the DARPin may be an anti-EGFR DARPin (or EGFR-binding DARPin), which targets EGFR, i.e., specifically binding to EGFR. In this case, the bispecific chimeric protein includes (a) an anti-EGFR DARPin and (b) an antibody (e.g., IgG antibody), an antibody fragment (e.g., scFv-Fc antibody fragment), or a combination thereof. In another embodiment, a method of preparing a bispecific chimeric protein including binding (a) an anti-EGFR DARPin to (b) an antibody (e.g., IgG antibody), an antibody fragment (e.g., scFv-Fc antibody fragment), or a combination thereof is provided. The bispecific chimeric protein comprising an anti-EGFR DARPin and an antibody and/or antibody fragment may be used as a bispecific antibody targeting two or more antigens including EGFR or two or more recognition sites.

The anti-EGFR DARPin may be any DARPin having DARPin's own unique structure and specifically binding to EGFR. For example, the anti-EGFR DARPin may be at least on selected from the group consisting of the following 4 anti-EGFR DARPins:

```
anti-EGFR DARPin-01 (SEQ ID NO: 109):
dlgkklleaaragqddevrilmangadvnaddtwgwtplhlaayqghlei
vevllkngadvnaydyigwtplhlaadghleivevllkngadvnasdyig
dtplhlaahnghleivevllkhgadvnaqdkfgktafdisidngnedlae
ilq anti-EGFR DARPin-67 (SEQ ID NO: 110):
dlgkklleaaragqddevrilmangadvnatdndgntplhlsawighlei
vevllkhgadvnaddllgmtplhlaadtghleivevllkygadvnardtr
gktplhlaardghleivevllkhdadvnaqdkfgktafdisidngnedla
eilq anti-EGFR DARPin-68 (SEQ ID NO: 111):
dlgkklleaaragqddevrilmangadvnafdywgmtplhlaadnghlei
vevllkhgadvnasdnfgftplhlaafyghleivevllkhgadvnafdmw
gntplhlaaqnghleivevllkngadvnaqdkfgktafdisidngnedla
eilq anti-EGFR DARPin-69 (SEQ ID NO: 112):
dlgkklleaaragqddevrilmangadvnaddnagrtplhlaanfghlei
vevllkngadvnakghhcntplhlaawaghleivevllkygadvnaddde
gytplhlaadigdleivevllkygadvnawdmygrtplhlaasaghleiv
evllkygadvnaqdkfgktafdisidngnedlaeilq
```

In the bispecific chimeric protein, an antibody having an IgG form and/or an antibody having a scFv-Fc form may target EGFR or may target a different antigen from the anti-EGFR DARPin. When the antibody having an IgG form and/or the antibody having a scFv-Fc form targets the same antigen as the anti-EGFR DARPin, the epitopes recognized and bound by the antibody and the anti-EGFR DARPin may be the same or different from each other.

As described above, EGFR is a main target in cancer therapy. If at least one of other tumor related proteins (HER1, ErbB-1), such as cell signal transduction related proteins including signal transduction molecules (e.g., growth factors), cell membrane proteins (e.g., receptors such as receptor tyrosine kinase proteins, etc.), and the like, is targeted, an increased anticancer effect can be obtained. When the antibody having an IgG form and/or the antibody having a scFv-Fc form targets (recognizes) an antigen different from the antigen targeted by the anti-EGFR DARPin, the antigen recognized by the antibody or antibody fragment may be independently selected from the group consisting tumor related proteins, for example, growth factors and receptor tyrosine kinase proteins other than EGFR. The growth factor may include, for example, EGF (Epidermal growth factor), PDGF (Platelet-derived growth factor), FGF (fibroblast growth factor), VEGF (vascular endothelial growth factor), and the like. The receptor tyrosine kinase proteins may include receptors of the growth factors, and particularly include ErbB family such as HER2, HER3, etc., insulin receptors, PDGF receptors (Platelet-derived growth factor receptors; PDGFRs), FGF receptors (fibroblast growth factor receptors; FGFRs), VEGF receptors (vascular endothelial growth factor receptors; PDGFRs), HGF receptors (hepatocyte growth factor receptors; HGFR) such as c-Met, etc., Trk receptors (tropomyosin-receptor-kinase receptors), Eph receptors (Ephrin receptors), AXL receptors, LTK receptors (Leukocyte receptor tyrosine kinase), TIE receptors, ROR receptors (receptor tyrosine kinase-like orphan receptors), DDR receptors (Discoidin domain receptors), RET receptors, KLG receptors, RYK receptors (related to receptor tyrosine kinase receptors), MuSK receptors (Muscle-Specific Kinase receptors), and the like. In one particular embodiment, the antibody having an IgG form and/or the antibody having a scFv-Fc form may independently recognize at least one selected from the group consisting of c-Met, HER2, HER3, VEGF and the like, as an antigen (see, e.g., FIG. 1).

The antibody having an IgG form may have an IgG1 or IgG2 subtype form. The structure of the antibody having an IgG form is described above. The antibody having an IgG form may be a monospecific antibody targeting a single antigen (single targeting antibody) which includes an antigen-binding region for the same antigen at both of the two heavy chain-light chain structures; or a an antibody capable of targeting two antigens (dual targeting antibody) which includes antigen-binding regions for different antigens respectively at each of the two heavy chain-light chain structures. The antibody having a scFv-Fc form may be a monospecific antibody in a monomeric form for targeting a single antigen, which includes one scFv-Fc fragment including an antigen-binding region for one antigen; a monospecific antibody in a dimeric form for targeting a single antigen, which includes two scFv-Fc fragments including antigen-binding regions for the same antigen, where the two scFv-Fc fragments are linked to each other at Fc region; or a an antibody in a dimeric form capable of targeting two antigens, which includes two scFv-Fc fragments including antigen-binding regions for different antigens from each other, where the two scFv-Fc fragments are linked to each other at Fc region. When the antibody having an IgG form or a scFv-Fc form is capable of targeting two antigens, one of the two antigens to be targeted may be EGFR, and in this case, the antibody may recognize and/or bind to the same region of EGFR with or different region of EGFR from the anti-EGFR DARPin.

In the antibody having an IgG form or a scFv-Fc form, the term "antigen-binding region" is described as above, and may be a polypeptide including a fragment that specifically binding to an antigen, for example, a heavy chain CDR (complementarity determining region), a light chain CDR, a heavy chain variable region, a light chain variable region, or a combination thereof (for e.g., scFv, (scFv)2, Fab, Fab', or F(ab')2), wherein the antigen is at least one selected from the group consisting of tumor related proteins, for example, growth factors and receptor tyrosine kinase proteins.

The anti-EGFR DARPin may be linked to C-terminus, N-terminus, or any linkable site of the antibody (e.g., an IgG antibody) or an antibody fragment (e.g. scFv-Fc antibody fragment). For example, in order to preserve the antigen-binding ability of the antibody or antibody fragment, the anti-EGFR DARPin may be linked to C-terminus of the antibody (e.g., an IgG antibody) or an antibody fragment (e.g. scFv-Fc antibody fragment), but not be limited thereto.

If the bispecific chimeric protein includes an anti-EGFR DARPin and a combination of an antibody having an IgG form and an antibody having a scFv-Fc form, the anti-EGFR DARPin, the antibody having an IgG form, and the antibody having a scFv-Fc form may be linked in any order. Although in some cases, the efficacy or expression rate of the bispecific chimeric protein may depend on the linking order, in general cases, the linking order has no negative effect on the desired efficacy of the bispecific chimeric protein. For example, the bispecific chimeric protein may include an antibody having an IgG form, an anti-EGFR DARPin linked to C-terminus of the antibody having an IgG form, and an antibody having a scFv-Fc form linked to C-terminus of the anti-EGFR DARPin, but not be limited thereto.

The bispecific chimeric protein may include at least one anti-EGFR DARPin, for example, about 1 to about 10, about 1 to 5, or 1 to 3 anti-EGFR DARPins, which include the same amino acid sequence, or at least two kinds of DARPins, for example, about 2 to about 10, about 2 to about 5, or about 2 to about 3 kinds of anti-EGFR DARPins, which include different amino acid sequences. When the anti-EGFR DARPins include different amino acid sequences, the epitope of EGFR recognized and/or bound by the anti-EGFR DARPins by may be the same with or different from each other. In addition to the anti-EGFR DARPin, one or more DARPins, for example, about 1 to about 10 kinds, about 1 to about 5 kinds, or about 1 to about 3 kinds of DARPins, which target other protein than EGFR, may be further included in the bispecific chimeric protein. When at least two DARPins or at least two kinds of DARPins are included, the at least two DARPins or the at least two kinds of DARPins may be linked to each other (e.g., to provide a repeated form of DARPin) and then linked to the antibody (having an IgG form or a scFv-Fc form) by at least one of C-terminus, N-terminus, and other linkable site of each chain of the antibody having an IgG form or a scFv-Fc form. For example, the anti-EGFR DARPin may be a repeated form, wherein one or more anti-EGFR DARPins selected from the group consisting of anti-EGFR DARPins including the amino acid sequence of SEQ ID NOs: 109, 110, 111, and 112 are repeated 1 to 10 times, about 1 to about 5 times, or about 1 to about 3 times, and in this case, the repeated form of anti-EGFR DARPins may be linked to C-terminus, N-terminus, and other linkable site, for example, C-terminus of a heavy chain (e.g., Fc region) or C-terminus of a light chain, of the antibody having an IgG form and/or a scFv-Fc form. For example, the anti-EGFR DARPin may include at least one anti-EGFR DARPin selected from the group consisting of anti-EGFR DARPins of SEQ ID NO: 109, SEQ ID NO: 110, SEQ ID NO: 111, and SEQ ID NO: 112 or a repeated form where the at least one anti-EGFR DARPin is repeated 2 to 10 times, 2 to 5 time, or 2 to 3 times.

Figure 2:
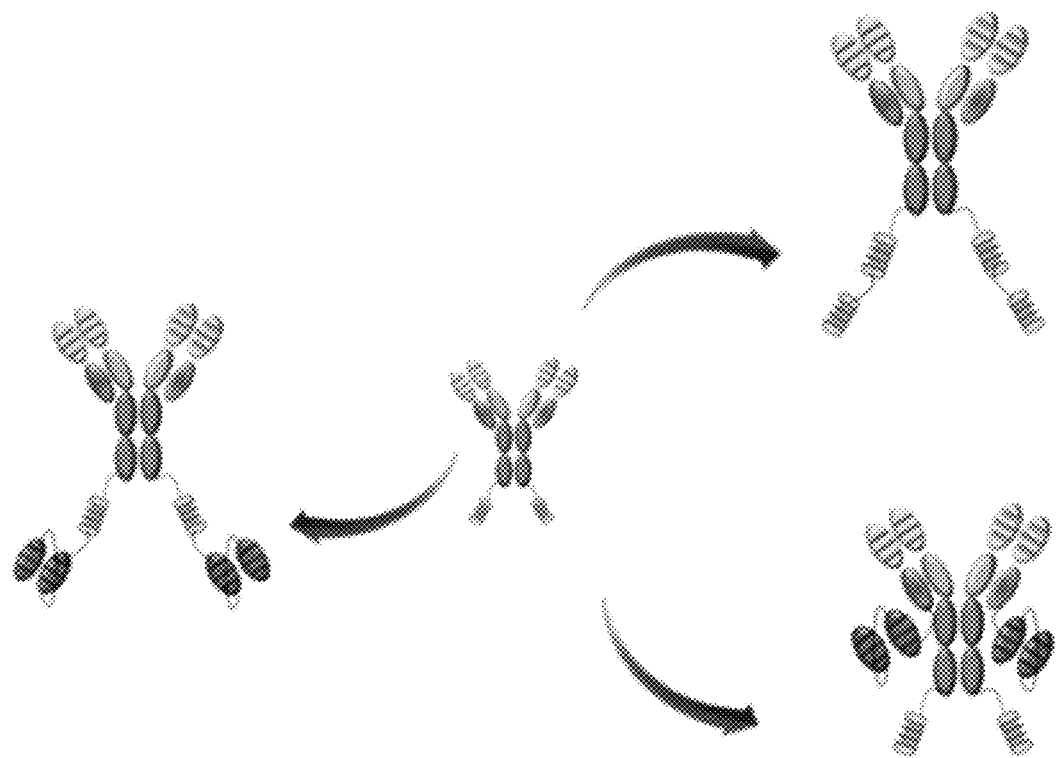
FIG. 2 is a schematic depicting processes of preparing various bispecific chimeric proteins using an anti-EGFR DARPin according to an embodiment.

The bispecific chimeric protein may further include at least one kind, for example, 1 to 5 or 1 to 3 kinds of antigen-binding fragments targeting the same or different antigen from that of the anti-EGFR DARPin, the antibody in an IgG form and the antibody in a scFv-Fc form. The additional antigen-binding fragment may be a heavy chain CDR, a light chain CDR, a heavy chain variable region, a light chain variable region, or a combination thereof (e.g., scFv, (scFv)2, Fab, Fab', or F(ab')2, of an antibody targeting at least one selected from growth factors and receptor tyrosine kinase proteins, and linked to any linkable site of the bispecific chimeric protein, for example, C-terminus of the heavy chain (e.g., Fc region) or C-terminus of the light chain of the antibody having an IgG form and/or a scFv-Fc form, or C-terminus of the anti-EGFR DARPin (see e.g., FIG. 2). For example, the antigen-binding fragment may be at least one selected from the group consisting of an antigen-binding fragment to c-Met (antigen-binding region of an anti-c-Met antibody), an antigen-binding fragment to HER2, an antigen-binding fragment to HER3, an antigen-binding fragment to EGFR, an antigen-binding fragment to VEGF, and the like.

An anti-EGFR DARPin and an antibody in an IgG form and/or in a scFv-Fc form; a heavy chain variable region and a light chain variable region in the scFv-Fc; a scFv-Fc and a scFv-Fc (in case of forming a dimer); and an antigen binding fragment, an anti-EGFR DARPin, and an antibody in an IgG form and/or in a scFv-Fc form may be linked to each other with or without a linker. The linker is described as above.

Since the anti-EGFR DARPin has high affinity to an antigen (EGFR), and higher stability and smaller molecular weight than those of general antibody fragment (e.g., scFv, Fab, etc.), the anti-EGFR DARPin is advantageous in respect of properties (such as pharmacokinetic (PK) properties in the living body) and stability in the living body. In addition, the anti-EGFR DARPin can be readily fused with other protein. Therefore, the DARPin can be useful in preparing a bispecific chimeric protein having excellent properties and stability in the body.

In an embodiment, the antibody in an IgG form and/or the antibody fragment in a scFv-Fc form may be an ant-c-Met antibody that targets c-Met. In embodiment, the bispecific chimeric protein comprising an anti-EGFR DARPin and an anti-c-Met antibody or its fragment may be used as a bispecific antibody targeting EGFR and c-Met.

c-Met is a representative receptor tyrosine kinase protein, which interacts with EGFR and participates in various tumor-related mechanisms. These proteins induce proliferation and penetration of cancer cells, angiogenesis, etc. In addition, these proteins interact with each other and participate in each other's signal transduction pathways, thereby inducing resistance to each treatment. In addition, the resistance acquired by administration of an EGFR-targeting treatment (Erbitux®, Tarceva®, Iressa™, etc.) is related to over-expression and mutation of c-Met. Therefore, simultaneous inhibition of EGFR and c-Met may achieve increased possibility of overcoming many problems of pre-existing anti-cancer treatments, such as side effects, resistances, and the like, as well as increased therapeutic effect compared to the case of inhibition of single target. Thus, it is expected that therapeutic effects on cancer can be obtained by simultaneously inhibiting EGFR and c-Met.

In addition, the antibody targeting c-Met only exhibits cancer cell proliferation inhibiting effect on limited kinds of cancer. In case that c-Met is overexpressed, over-expression of EGFR is often observed. Therefore, it is advantageous to simultaneously inhibit c-Met and EGFR for overcoming the resistance to c-Met targeting treatments.

Therefore, an embodiment provides a bispecific chimeric protein includes (a) an anti-EGFR DARPin, and (b) an antibody having an IgG form, an antibody having a scFv-Fc form, or a combination thereof. Another embodiment provides a method of preparing a bispecific chimeric protein including binding (a) an anti-EGFR DARPin to (b) an antibody having an IgG form, an antibody having a scFv-Fc form, or a combination thereof. When the anti-EGFR DARPin is one including at least two kinds of anti-EGFR DARPins, the method may further include a step of linking (for example, linking in tandem) the at least two kinds, for example, about 2 to about 10 kinds, about 2 to about 5 kinds, or about 2 to about 3 kinds of anti-EGFR DARPins with one another, before or after the step of binding an anti-EGFR DARPin to an antibody having an IgG form, an antibody having a scFv-Fc form, or a combination thereof.

The anti-c-Met antibody may be capable of inducing intracellular internalization and degradation of c-Met. Based on such capability of c-Met, the bispecific chimeric protein including an anti-EGFR, DARPin, and an anti-c-Met antibody may induce EGFR degradation as well as c-Met degradation, thereby leading to increased anticancer activity without agonism. When the bispecific chimeric protein is applied, EGFR clustering is observed. The EGFR clustering leads to clustering of related protein tyrosine kinases (PTKs) to form signal transduction complex, which is intracellularly internalized and degraded along with c-Met, whereby the increased therapeutic effects of the bispecific chimeric protein can be obtained. The increased therapeutic effects of the bispecific chimeric protein can be more increased when a ligand of c-Met, HGF (Hepatocyte growth factor), is present, and such effects can be more clearly observed in c-Met overexpressed cells (e.g., cancer cells). In addition, the bispecific chimeric protein can overcome resistance to a c-Met targeting treatment, such as an anti-c-Met antibody, and/or an EGFR-targeting treatment, such as an anti-EGFR antibody, thereby exhibiting therapeutic effects even on cancer cells having resistance to such treatment. The bispecific chimeric protein including an anti-EGFR DARPin and an anti-c-Met antibody can exhibit more increased effects due to distinguished therapeutic mechanism from that of pre-existing antibodies, as described above.

The anti-c-Met antibody may be any antibody or antigen-binding fragment that acts on c-Met to induce intracellular internalization and degradation of c-Met. The anti-c-Met antibody may be any one recognizing a specific region of c-Met, e.g., a specific region in the SEMA domain, as an epitope.

The "c-Met protein" refers to a receptor tyrosine kinase binding to hepatocyte growth factor. The c-Met proteins may be derived from any species, for example, those derived from primates such as human c-Met (e.g., NP_000236) and monkey c-Met (e.g., Macaca mulatta, NP_001162100), or those derived from rodents such as mouse c-Met (e.g., NP_032617.2) and rat c-Met (e.g., NP_113705.1). The proteins include, for example, a polypeptide encoded by the nucleotide sequence deposited under GenBank Accession Number NM_000245, or a protein encoded by the polypeptide sequence deposited under GenBank Accession Number NM_000236, or extracellular domains thereof. The receptor tyrosine kinase c-Met is involved in several mechanisms including cancer incidence, cancer metastasis, cancer cell migration, cancer cell penetration, angiogenesis, etc.

c-Met, a receptor for hepatocyte growth factor (HGF), may be divided into three portions: extracellular, transmembrane, and intracellular. The extracellular portion is composed of an α-subunit and a β-subunit which are linked to each other through a disulfide bond, and contains a SEMA domain responsible for binding HGF, a PSI domain (plexin-semaphorins-integrin homology domain) and an IPT domain (immunoglobulin-like fold shared by plexins and transcriptional factors domain). The SEMA domain of c-Met protein may have the amino acid sequence of SEQ ID NO: 79, and is an extracellular domain that functions to bind HGF. A specific region of the SEMA domain, that is, a region having the amino acid sequence of SEQ ID NO: 71, which corresponds to a range from amino acid residues 106 to 124 of the amino acid sequence of the SEMA domain (SEQ ID NO: 79) of c-Met protein, is a loop region between the second and the third propellers within the epitopes of the SEMA domain. The region acts as an epitope for the specific anti-c-Met antibody of the present invention.

The term "epitope" as used herein, refers to an antigenic determinant, a part of an antigen recognized by an antibody. In one embodiment, the epitope may be a region including 5 or more contiguous (consecutive or non-consecutive) amino acid residues within the SEMA domain (SEQ ID NO: 79) of c-Met protein, for instance, 5 to 19 contiguous amino acid residues within the amino acid sequence of SEQ ID NO: 71. The epitope may be a polypeptide having 5 to 19 contiguous amino acids selected from among partial combinations of the amino acid sequence of SEQ ID NO: 71, wherein the polypeptide essentially includes the amino sequence of SEQ ID NO: 73 (EEPSQ) serving as an essential element for the epitope. For example, the epitope may be a polypeptide comprising, consisting essentially of, or consisting of the amino acid sequence of SEQ ID NO: 71, SEQ ID NO: 72, or SEQ ID NO: 73.

The epitope having the amino acid sequence of SEQ ID NO: 72 corresponds to the outermost part of the loop between the second and third propellers within the SEMA domain of a c-Met protein. The epitope having the amino acid sequence of SEQ ID NO: 73 is a site to which the antibody or antigen-binding fragment according to one embodiment most specifically binds.

Thus, the anti-c-Met antibody may specifically bind to an epitope which has 5 to 19 contiguous amino acids selected from among partial combinations of the amino acid sequence of SEQ ID NO: 71, including SEQ ID NO: 73 as an essential element. For example, the anti-c-Met antibody may specifically bind to an epitope including the amino acid sequence of SEQ ID NO: 71, SEQ ID NO: 72, or SEQ ID NO: 73.

In one embodiment, the anti-c-Met antibody or an antigen-binding fragment thereof may include:

at least one heavy chain complementarity determining region (CDR) selected from the group consisting of (a) a CDR-H1 having the amino acid sequence of SEQ ID NO: 4; (b) a CDR-H2 having the amino acid sequence of SEQ ID NO: 5, SEQ ID NO: 2, or an amino acid sequence having 8-19 consecutive amino acids within SEQ ID NO: 2, wherein the 8-19 consecutive amino acids includes amino acid residues from the $3^{rd}$ to $10^{th}$ positions of SEQ ID NO: 2; and (c) a CDR-H3 having the amino acid sequence of SEQ ID NO: 6, SEQ ID NO: 85, or an amino acid sequence having 6-13 consecutive amino acids within SEQ ID NO: 85 wherein the 6-13 consecutive amino acids includes amino acid residues from the $1^{st}$ to $6^{th}$ positions of SEQ ID NO: 85, or a heavy chain variable region including the at least one heavy chain complementarity determining region;

at least one light chain complementarity determining region (CDR) selected from the group consisting of (a) a CDR-L1 having the amino acid sequence of SEQ ID NO: 7, (b) a CDR-L2 having the amino acid sequence of SEQ ID NO: 8, and (c) a CDR-L3 having the amino acid sequence of SEQ ID NO: 9, SEQ ID NO: 86, or an amino acid sequence having 9-17 consecutive amino acids within SEQ ID NO: 89 wherein the 9-17 consecutive amino acids includes amino acid residues from the $1^{st}$ to $9^{th}$ positions of SEQ ID NO: 89, or a light chain variable region including the at least one light chain complementarity determining region;

a combination of the at least one heavy chain complementarity determining region and at least one light chain complementarity determining region; or a combination of the heavy chain variable region and the light chain variable region.

Herein, the amino acid sequences of SEQ ID NOS: 4 to 9 are respectively represented by following Formulas I to VI, below:

Formula I
(SEQ ID NO: 4)
$Xaa_1$-$Xaa_2$-Tyr-Tyr-Met-Ser,
wherein $Xaa_1$ is absent or Pro or Ser, and $Xaa_2$ is Glu or Asp, Formula II
(SEQ ID NO: 5)
Arg-Asn-$Xaa_3$-$Xaa_4$-Asn-Gly-$Xaa_5$-Thr,
wherein $Xaa_3$ is Asn or Lys, $Xaa_4$ is Ala or Val, and $Xaa_5$ is Asn or Thr, Formula III
(SEQ ID NO: 6)
Asp-Asn-Trp-Leu-$Xaa_6$-Tyr,
wherein $Xaa_6$ is Ser or Thr, Formula IV
(SEQ ID NO: 7)
Lys-Ser-Ser-$Xaa_7$-Ser-Leu-Leu-Ala-$Xaa_8$-Gly-Asn-$Xaa_9$-$Xaa_{10}$-Asn-Tyr-Leu-Ala
wherein $Xaa_7$ is His, Arg, Gln, or Lys, $Xaa_8$ is Ser or Trp, $Xaa_9$ is His or Gln, and $Xaa_{10}$ is Lys or Asn, Formula V
(SEQ ID NO: 8)
Trp-$Xaa_{11}$-Ser-$Xaa_{12}$-Arg-Val-$Xaa_{13}$
wherein $Xaa_{11}$ is Ala or Gly, $Xaa_{12}$ is Thr or Lys, and $Xaa_{13}$ is Ser or Pro,
and Formula VI
(SEQ ID NO: 9)
$Xaa_{14}$-Gln-Ser-Tyr-Ser-$Xaa_{15}$-Pro-$Xaa_{16}$-Thr
wherein $Xaa_{14}$ is Gly, Ala, or Gln, $Xaa_{15}$ is Arg, His, Ser, Ala, Gly, or Lys, and $Xaa_{16}$ is Leu, Tyr, Phe, or Met.

In one embodiment, the CDR-H1 may include an amino acid sequence selected from the group consisting of SEQ ID NOS: 1, 22, 23, and 24. The CDR-H2 may include an amino acid sequence selected from the group consisting of SEQ ID NOS: 2, 25, and 26. The CDR-H3 may include an amino acid sequence selected from the group consisting of SEQ ID NOS: 3, 27, 28, and 85.

The CDR-L1 may include an amino acid sequence selected from the group consisting of SEQ ID NOS: 10, 29, 30, 31, 32, 33, and 106. The CDR-L2 may include an amino acid sequence selected from the group consisting of SEQ ID NOS: 11, 34, 35, and 36. The CDR-L3 may include an amino acid sequence selected from the group consisting of SEQ ID NOS: 12, 13, 14, 15, 16, 37, 86, and 89.

In another embodiment, the antibody or antigen-binding fragment may include a heavy chain variable region comprising a polypeptide (CDR-H1) including an amino acid sequence selected from the group consisting of SEQ ID NOS: 1, 22, 23, and 24, a polypeptide (CDR-H2) including an amino acid sequence selected from the group consisting of SEQ ID NOS: 2, 25, and 26, and a polypeptide (CDR-H3) including an amino acid sequence selected from the group consisting of SEQ ID NOS: 3, 27, 28, and 85; and a light chain variable region comprising a polypeptide (CDR-L1) including an amino acid sequence selected from the group consisting of SEQ ID NOS: 10, 29, 30, 31, 32, 33 and 106, a polypeptide (CDR-L2) including an amino acid sequence selected from the group consisting of SEQ ID NOS: 11, 34, 35, and 36, and a polypeptide (CDR-L3) including an amino acid sequence selected from the group consisting of SEQ ID NOS 12, 13, 14, 15, 16, 37, 86, and 89.

In one embodiment of the anti-c-Met antibody or antigen-binding fragment, the variable region of the heavy chain includes the amino acid sequence of SEQ ID NO: 17, 74, 87, 90, 91, 92, 93, or 94 and the variable region of the light chain includes the amino acid sequence of SEQ ID NO: 18, 19, 20, 21, 75, 88, 95, 96, 97, 98, 99, or 107.

Animal-derived antibodies produced by immunizing non-immune animals with a desired antigen generally invoke immunogenicity when injected to humans for the purpose of medical treatment, and thus chimeric antibodies have been developed to inhibit such immunogenicity. Chimeric antibodies are prepared by replacing constant regions of animal-derived antibodies that cause an anti-isotype response with constant regions of human antibodies by genetic engineering. Chimeric antibodies are considerably improved in an anti-isotype response compared to animal-derived antibodies, but animal-derived amino acids still have variable regions, so that chimeric antibodies have side effects with respect to a potential anti-idiotype response. Humanized antibodies have been developed to reduce such side effects. Humanized antibodies are produced by grafting complementarity determining regions (CDR) which serve an important role in antigen binding in variable regions of chimeric antibodies into a human antibody framework.

The most important thing in CDR grafting to produce humanized antibodies is choosing the optimized human antibodies for accepting CDRs of animal-derived antibodies. Antibody databases, analysis of a crystal structure, and technology for molecule modeling are used. However, even when the CDRs of animal-derived antibodies are grafted to the most optimized human antibody framework, amino acids positioned in a framework of the animal-derived CDRs affecting antigen binding are present. Therefore, in many cases, antigen binding affinity is not maintained, and thus application of additional antibody engineering technology for recovering the antigen binding affinity is necessary.

The anti c-Met antibodies may be mouse-derived antibodies, mouse-human chimeric antibodies, humanized antibodies, or human antibodies. The antibodies or antigen-binding fragments thereof may be isolated from a living body or non-naturally occurring. The antibodies or antigen-binding fragments thereof may be recombinant or synthetic.

An intact antibody includes two full-length light chains and two full-length heavy chains, in which each light chain is linked to a heavy chain by disulfide bonds. The antibody has a heavy chain constant region and a light chain constant region. The heavy chain constant region is of a gamma ($\gamma$), mu ($\mu$), alpha ($\alpha$), delta ($\delta$), or epsilon ($\epsilon$) type, which may be further categorized as gamma 1 ($\gamma$1), gamma 2 ($\gamma$2), gamma 3 ($\gamma$3), gamma 4 ($\gamma$4), alpha 1 ($\alpha$1), or alpha 2 ($\alpha$2). The light chain constant region is of either a kappa ($\kappa$) or lambda ($\lambda$) type.

As used herein, the term "heavy chain" refers to full-length heavy chain, and fragments thereof, including a variable region $V_H$ that includes amino acid sequences sufficient to provide specificity to antigens, and three constant regions, $C_{H1}$, $C_{H2}$, and $C_{H3}$, and a hinge. The term "light chain" refers to a full-length light chain and fragments thereof, including a variable region $V_L$ that includes amino acid sequences sufficient to provide specificity to antigens, and a constant region $C_L$.

The term "complementarity determining region (CDR)" refers to an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDR may provide contact residues that play an important role in the binding of antibodies to antigens or epitopes. The terms "specifically binding" and "specifically recognized" are well known to one of ordinary skill in the art, and indicate that an antibody and an antigen specifically interact with each other to lead to an immunological activity.

The term "antigen-binding fragment" used herein refers to fragments of an intact immunoglobulin including portions of a polypeptide including antigen-binding regions having the ability to specifically bind to the antigen. In a particular embodiment, the antigen-binding fragment may be scFv, (scFv)$_2$, scFvFc, Fab, Fab', or F(ab')$_2$, but is not limited thereto.

Among the antigen-binding fragments, Fab that includes light chain and heavy chain variable regions, a light chain constant region, and a first heavy chain constant region $C_{H1}$, has one antigen-binding site.

The Fab' fragment is different from the Fab fragment, in that Fab' includes a hinge region with at least one cysteine residue at the C-terminal of $C_{H1}$.

The F(ab')$_2$ antibody is formed through disulfide bridging of the cysteine residues in the hinge region of the Fab' fragment.

Fv is the smallest antibody fragment with only a heavy chain variable region and a light chain variable region. Recombination techniques of generating the Fv fragment are widely known in the art.

Two-chain Fv includes a heavy chain variable region and a light chain region which are linked by a non-covalent bond. Single-chain Fv generally includes a heavy chain variable region and a light chain variable region which are linked by a covalent bond via a peptide linker or linked at the C-terminals to have a dimer structure like the two-chain Fv. The peptide linker may be the same as described in the above, for example, those including the amino acid length of about 1 to about 100, about 2 to about 50, particularly about 5 to about 25, and any kinds of amino acids may be included without any restrictions.

The antigen-binding fragments may be attainable using protease (for example, the Fab fragment may be obtained by restricted cleavage of a whole antibody with papain, and the F(ab')$_2$ fragment may be obtained by cleavage with pepsin), or may be prepared by using a genetic recombination technique.

The term "hinge region," as used herein, refers to a region between CH1 and CH2 domains within the heavy chain of an antibody which functions to provide flexibility for the antigen-binding site.

When an animal antibody undergoes a chimerization process, the IgG1 hinge of animal origin is replaced with a human IgG1 hinge or IgG2 hinge while the disulfide bridges between two heavy chains are reduced from three to two in number. In addition, an animal-derived IgG1 hinge is shorter than a human IgG1 hinge. Accordingly, the rigidity of the hinge is changed. Thus, a modification of the hinge region may bring about an improvement in the antigen binding efficiency of the humanized antibody. The modification of the hinge region through amino acid deletion, addition, or substitution is well-known to those skilled in the art.

In one embodiment, the anti-c-Met antibody or an antigen-binding fragment thereof may be modified by the deletion, insertion, addition, or substitution of at least one amino acid residue on the amino acid sequence of the hinge region so that it exhibit enhanced antigen-binding efficiency. For example, the antibody may include a hinge region including the amino acid sequence of SEQ ID NO: 100(U7-HC6), 101(U6-HC7), 102(U3-HC9), 103(U6-HC8), or 104(U8-HC5), or a hinge region including the amino acid sequence of SEQ ID NO: 105 (non-modified human hinge). In particular, the hinge region has the amino acid sequence of SEQ ID NO: 100 or 101.

In one embodiment, the anti-c-Met antibody may be a monoclonal antibody. The monoclonal antibody may be produced by the hybridoma cell line deposited with Accession No. KCLRF-BP-00220, which binds specifically to the extracellular region of c-Met protein (refer to Korean Patent Publication No. 2011-0047698, the disclosure of which is incorporated in its entirety herein by reference). The anti-c-Met antibody may include any of the antibodies defined in Korean Patent Publication No. 2011-0047698, the disclosure of which is hereby incorporated by reference.

In the anti-c-Met antibody, the rest portion of the light chain and the heavy chain portion excluding the CDRs, the light chain variable region, and the heavy chain variable region as defined above, that is the light chain constant region and the heavy chain constant region, may be those from any subtype of immunoglobulin (e.g., IgA, IgD, IgE, IgG (IgG1, IgG2, IgG3, IgG4), IgM, and the like).

By way of further example, the anti-c-Met antibody or the antibody fragment may include:

a heavy chain including the amino acid sequence selected from the group consisting of the amino acid sequence of SEQ ID NO: 62 (wherein the amino acid sequence from amino acid residues from the $1^{st}$ to $17^{th}$ positions is a signal peptide), or the amino acid sequence from the $18^{th}$ to $462^{nd}$ positions of SEQ ID NO: 62, the amino acid sequence of SEQ ID NO: 64 (wherein the amino acid sequence from the $1^{st}$ to $17^{th}$ positions is a signal peptide), the amino acid sequence from the $18^{th}$ to $461^{st}$ positions of SEQ ID NO: 64, the amino acid sequence of SEQ ID NO: 66 (wherein the amino acid sequence from the $1^{st}$ to $17^{th}$ positions is a signal peptide), and the amino acid sequence from the $18^{th}$ to $460^{th}$ positions of SEQ ID NO: 66; and a light chain including the amino acid sequence selected from the group consisting of the amino acid sequence of SEQ ID NO: 68 (wherein the amino acid sequence from the $1^{st}$ to $20^{th}$ positions is a signal peptide), the amino acid sequence from the $21^{st}$ to $240^{th}$ positions of SEQ ID NO: 68, the amino acid sequence of SEQ ID NO: 70 (wherein the amino acid sequence from the $1^{st}$ to $20^{th}$ positions is a signal peptide), the amino acid sequence from the $21^{st}$ to $240^{th}$ positions of SEQ ID NO: 70, and the amino acid sequence of SEQ ID NO: 108.

For example, the anti-c-Met antibody may be selected from the group consisting of:

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 108;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 108; and an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 108.

According to an embodiment, the anti-c-Met antibody may include a heavy chain including the amino acid sequence from the $18^{th}$ to $460^{th}$ positions of SEQ ID NO: 66 and a light chain including the sequence from the $21^{st}$ to $240^{th}$ positions of SEQ ID NO: 68, or a heavy chain including the amino acid sequence from the $18^{th}$ to $460^{th}$ positions of SEQ ID NO: 66 and a light chain including the sequence of SEQ ID NO: 108.

The polypeptide of SEQ ID NO: 70 is a light chain including human kappa (κ) constant region, and the polypeptide with the amino acid sequence of SEQ ID NO: 68 is a polypeptide obtained by replacing histidine at position 62 (corresponding to position 36 of SEQ ID NO: 68 according to kabat numbering) of the polypeptide with the amino acid sequence of SEQ ID NO: 70 with tyrosine. The production yield of the antibodies may be increased by the replacement. The polypeptide with the amino acid sequence of SEQ ID NO: 108 is a polypeptide obtained by replacing serine at position 32 of the amino acid sequence of SEQ ID NO: 68 (corresponding to position 52 of SEQ ID NO: 68, which corresponds to position 27e according to kabat numbering in the amino acid sequence from amino acid residues 21 to 240 of SEQ ID NO: 68; positioned within CDR-L1) with tryptophan. By such replacement, antibodies and antibody fragments including such sequences exhibits increased activities, such as c-Met biding affinity, c-Met degradation activity, Akt phosphorylation inhibition, and the like.

In another embodiment, the anti-c-Met antibody may include a light chain complementarity determining region including the amino acid sequence of SEQ ID NO: 106, a light chain variable region including the amino acid sequence of SEQ ID NO: 107, or a light chain including the amino acid sequence of SEQ ID NO: 108.

In an embodiment, the anti-c-Met antibody may be in an IgG form, for example, in a form of IgG1 or IgG2 subtype. The structure of the antibody in an IgG is as described above.

The anti-c-Met antibody having an IgG form may be a monospecific antibody (single targeting antibody) including an antigen-binding region (e.g., a heavy chain CDR, a light chain CDR, a heavy chain variable region, a light chain variable region, or a combination thereof) for c-Met at both of the two heavy chain-light chain structures. Alternatively, the anti-c-Met antibody having an IgG form may be an antibody capable of targeting two antigens (dual targeting antibody) including an antigen-binding region (e.g., a heavy chain CDR, a light chain CDR, a heavy chain variable region, a light chain variable region, or a combination thereof) for c-Met at one of the two heavy chain-light chain structures, and an antigen-binding region for an antigen other than c-Met at the other heavy chain-light chain structure. In this case, the antigen other than c-Met may be an EGFR.

In another embodiment, the anti-c-Met antibody having an IgG form may be a top and bottom asymmetric antibody capable of binding multiple epitopes, which may include a monospecific antibody in a IgG form including an antigen-binding region for c-Met at both of the two heavy chain-light chain structures and an antigen-binding region (e.g., a heavy chain CDR, a light chain CDR, a heavy chain variable region, a light chain variable region, or a combination thereof (e.g., scFv, (scFv)2, Fab, Fab', or F(ab')2)) for an antigen other than c-Met linked to C-terminus of Fc of the monospecific antibody in a IgG form with or without a linker. In this case, the antigen other than c-Met may be an EGFR. The linker is described as above.

In another embodiment, the antibody having a scFv-Fc form may be a monospecific antibody in a monomeric form for targeting c-Met, which includes one scFv-Fc fragment including an antigen-binding region (e.g., a heavy chain CDR, a light chain CDR, a heavy chain variable region, a light chain variable region, or a combination thereof) for c-Met; a monospecific antibody in a dimeric form for targeting a single antigen, which includes two scFv-Fc fragments including antigen-binding regions for c-Met, where the two scFv-Fc fragments are linked to each other at Fc region; or a an antibody in a dimeric form capable of targeting c-Met and another antigen, which includes a scFv-Fc fragment including an antigen-binding region for c-Met and a scFv-Fc fragment including an antigen-binding region for an antigen other than c-Met, where the two scFv-Fc fragments are linked to each other at Fc region. The antigen other than c-Met may be an EGFR.

In another embodiment, the bispecific chimeric protein may include an anti-EGFR DARPin and an antibody having an IgG form or a scFv-Fc form against a tumor-related protein other than c-Met, for example, selected from the group consisting of receptors, signal transduction molecules, and the like. The signal transduction molecule may be selected from the group consisting of growth factors, such as EGF, PDGF, FGF, VEGF, and the like. The receptor may be a receptor specifically binding to a signal transduction molecule, and selected from the group consisting of ErbBs (such as EGFR, HER2, HER3, and the like), PDGFR, FGFR, VEGFR, HGFR other than c-Met, and the like.

For example, the antibody having an IgG form or a scFv-Fc form may include an antigen-binding region selected from the group consisting of the following:

(1) an antigen-binding region for HER2: an antigen-binding region (e.g., a heavy chain CDR, a light chain CDR, a heavy chain variable region, a light chain variable region, or a combination thereof (e.g., scFv, (scFv)2, Fab, Fab', or F(ab')2)) of an anti-HER2 antibody selected from the group consisting of trastuzumab, pertuzumab, trastuzumab emtansine (T-DM1), and the like; or a heavy chain variable region including the amino acid sequence of SEQ ID NO: 113, a light chain variable region including the amino acid sequence of SEQ ID NO: 114, or a combination thereof (wherein, the heavy chain variable region and the light chain variable region may be linked to each other with or without a peptide linker).

Wherein the amino acid sequence of a heavy chain variable region of an anti-HER2 antibody comprises

```
                                     (SEQ ID NO: 113)
EVQLVESGGGLVQPGGSLRLSCAASGFNIKDTYIHWVRQAPGKGLEWVARI

YPTNGYTRYADSVKGRFTISADTSKNTAYLQMNSLRAEDTAVYYCSRWGGD

GFYAMDYWGQGTLVTVSS
``` and the amino acid sequence of a light chain variable region of an anti-HER2 antibody comprises>

```
                                     (SEQ ID NO: 114)
DIQMTQSPSSLSASVGDRVTITCRASQDVNTAVAWYQQKPGKAPKLLIYSA

SFLYSGVPSRFSGSRSGTDFTLTISSLQPEDFATYYCQQHYTTPPTFGQGT

KVEIKR
```

(2) an antigen-binding region for HER3: a heavy chain variable region including the amino acid sequence of SEQ ID NO: 115, a light chain variable region including the amino acid sequence of SEQ ID NO: 116, or a combination thereof (wherein, the heavy chain variable region and the light chain variable region may be linked to each other with or without a peptide linker).

wherein the amino acid sequence of a heavy chain variable region of an anti-HER3 antibody comprises

```
                                     (SEQ ID NO: 115)
QVQLQESGGGLVKPGGSLRLSCAASGFTFSSYWMSWVRQAPGKGLEWVANI

NRDGSASYYVDSVKGRFTISRDDAKNSLYLQMNSLRAEDTAVYYCARDRGV

GYFDLWGRGTLVTVSSAST
``` and the amino acid sequence of a light chain variable region of an anti-HER3 antibody comprises

```
                                     (SEQ ID NO: 116)
QSALTQPASVSGSPGQSITISCTGTSSDVGGYNFVSWYQQHPGKAPKLMIY

DVSDRPSGVSDRFSGSKSGNTASLIISGLQADDEADYYCSSYGSSSTHVIF

GGGTKVTVLG
```

(3) anti-EGGFR/anti-HER3 bispecific chimeric protein: a heavy chain variable region including the amino acid sequence of SEQ ID NO: 117, a light chain variable region including the amino acid sequence of SEQ ID NO: 118, or a combination thereof (wherein, the heavy chain variable region and the light chain variable region may be linked to each other with or without a peptide linker).

wherein the amino acid sequence of a heavy chain variable region of an anti-EGFR/anti-HER3 antibody comprises

```
                                           (SEQ ID NO: 117)
EVQLVESGGGLVQPGGSLRLSCAASGFTLSGDWIHWVRQAPGKGLEWVGEI

SAAGGYTDYADSVKGRFTISADTSKNTAYLQMNSLRAEDTAVYYCARESRV

SFEAAMDYWGQGTLVTVSS
``` and the amino acid sequence of a light chain variable region of an anti-EGFR/anti-HER3 antibody>

```
                                           (SEQ ID NO: 118)
DIQMTQSPSSLSASVGDRVTITCRASQNIATDVAWYQQKPGKAPKLLIYSA

SFLYSGVPSRFSGSGSGTDFTLTISSLQPEDFATYYCQQSEPEPYTFGQGT

KVEIK
```

The bispecific chimeric protein including an anti-EGFR DARPin and an antibody against a tumor-related protein may inhibit not only EGFR activity but also the tumor-related protein activity, thereby leading to more increased therapeutic effects. In particular, the bispecific chimeric protein including an anti-EGFR DARPin and an anti-c-Met antibody can fundamentally inhibit c-Met and EGFR by inhibiting the activity of c-Met and EGFR and decreasing the total amount of c-Met and EGFR by internalization and degradation activities of the antibody. Therefore, bispecific chimeric protein including an anti-EGFR DARPin and an anti-c-Met antibody can have therapeutic effects even when it is applied to a subject having a resistance to pre-existing anti-EGFR antagonist (antibody).

Another embodiment provides a pharmaceutical composition including the bispecific chimeric protein as an active ingredient. Another embodiment provides a pharmaceutical composition for preventing and/or treating a cancer including the bispecific chimeric protein as an active ingredient. Another embodiment provides a method of preventing and/or treating a cancer including administering a pharmaceutically effective amount of the bispecific chimeric protein to a subject in need of preventing and/or treating a cancer. The method may further include a step of identifying the subject in need of preventing and/or treating a cancer, prior to the step of administering. Another embodiment provides a use of the bispecific chimeric protein for preventing and/or treating a cancer. The bispecific chimeric protein may be a bispecific chimeric protein including (a) anti-EGFR DARPin and (b) an antibody in an IgG form, an antibody in a scFv-Fc form, or a combination thereof, or including (a) anti-EGFR DARPin, and (b) an anti-c-Met antibody in an IgG form, an anti-c-Met antibody in a scFv-Fc form, or a combination thereof.

The cancer may be associated with overexpression (overproduction) and/or abnormal activation of EGFR and/or c-Met. The cancer may be a solid cancer or hematological cancer and for instance, may be, but not limited to, one or more selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastric cancer, gastrointestinal cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head or neck cancer, brain cancer, osteosarcoma, and the like. In particular, the cancer may be cancer having resistance against pre-existing anticancer drugs, for example, antagonists against EGFR. The prevention and/or treatment effects of the cancers may include effects of not only suppressing the growth of the cancer cells but also suppressing deterioration of cancers due to migration, invasion, and metastasis thereof. Therefore, the curable cancers may include both primary cancers and metastatic cancers.

The bispecific chimeric protein may be administered or formulated along with a pharmaceutically acceptable carrier, diluent, and/or excipient.

The pharmaceutically acceptable carrier to be included in the composition may be those commonly used for the formulation of antibodies, which may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but are not limited thereto. The pharmaceutical composition may further include one or more selected from the group consisting of a lubricant, a wetting agent, a sweetener, a flavor enhancer, an emulsifying agent, a suspension agent, and preservative.

The pharmaceutical composition or the bispecific chimeric protein may be administered orally or parenterally. The parenteral administration may include intravenous injection, subcutaneous injection, muscular injection, intraperitoneal injection, endothelial administration, local administration, intranasal administration, intrapulmonary administration, and rectal administration. Since oral administration leads to digestion of proteins or peptides, an active ingredient in the compositions for oral administration must be coated or formulated to prevent digestion in stomach. In addition, the compositions may be administered using an optional device that enables an active substance to be delivered to target cells.

A suitable dosage of the pharmaceutical composition or the bispecific chimeric protein may be prescribed in a variety of ways, depending on factors such as formulation methods, administration methods, age of patients, body weight, gender, pathologic conditions, diets, administration time, administration route, excretion speed, and reaction sensitivity. A desirable dosage of the pharmaceutical composition or the bispecific chimeric protein may be in the range of about 0.001 to 100 mg/kg or 0.02 to 10 mg/kg per a day for an adult. The term "pharmaceutically effective amount" used herein refers to an amount exhibiting effects in preventing or treating cancer.

The pharmaceutical composition or the bispecific chimeric protein may be formulated with a pharmaceutically acceptable carrier and/or excipient into a unit or a multiple dosage form by a method easily carried out by a skilled person in the pertinent art. The dosage form may be a solution in oil or an aqueous medium, a suspension, syrup, an emulsifying solution, an extract, powder, granules, a tablet, or a capsule, and may further include a dispersing or a stabilizing agent.

In addition, the pharmaceutical composition or the bispecific chimeric protein may be administered as an individual drug, or together with other drugs, and may be administered sequentially in any order or simultaneously with pre-existing drugs.

Since the bispecific chimeric protein or the pharmaceutical composition includes an antibody or an antigen binding fragment thereof, it may be formulated as an immunoliposome. The liposome containing an antibody may be prepared using a well-known method in the pertinent art. The immunoliposome is a lipid composition including phosphatidylcholine, cholesterol, and polyethyleneglycol-derivatized phosphatidylethanolamine, and may be prepared by a reverse phase evaporation method. For example, Fab' fragments of an antibody may be conjugated to the liposome through a disulfide exchange reaction. A chemical drug such as doxorubicin may be additionally included in the liposome.

The subject to which the pharmaceutical composition or the bispecific chimeric protein is administered or the patient to which the prevention and/treatment method is applied may be a mammal, for example, a primate such as human and monkey, or a rodent such as rat and mouse, but are not be limited thereto. The subject or the patient may be a cancer patient having resistance against pre-existing anticancer drugs, for example, EGFR antagonists (e.g., an anti-EGFR antibody, etc.) and/or an anti-c-Met antibody.

As described above, DARPin has an excellent properties (e.g., pharmacokinetic (PK) properties) and stability in the body, and thus, when it is fused with a pre-existing antibody (e.g., an antibody in an IgG form) to prepare a bispecific chimeric protein, it can be achieved not only to simultaneously target at least two antigens including the target of the DARPin but also to enhance the properties and/or stability of the antibody in an IgG form. That is, by fusing a DARPin and a pre-existing antibody in an IgG form, the defect in stability, which is the main problem of the pre-existing bispecific chimeric protein, can be solved, and more increased effect can be achieved.

Accordingly, another embodiment provides a method of enhancement of an efficacy of an antibody, including binding (a) a DARPin to (b) an antibody having an IgG form, an antibody having a scFv-Fc form, or a combination thereof. Another embodiment provides a method of enhancement of an efficacy of an antibody, including binding (a) an anti-EGFR DARPin to (b) an antibody having an IgG form, an antibody having a scFv-Fc form, or a combination thereof. Another embodiment provides a method of enhancement of an efficacy of an anti-c-Met antibody, including binding (a) an anti-EGFR DARPin to (b) an anti-c-Met antibody having an IgG form, an anti-c-Met antibody having a scFv-Fc form, or a combination thereof.

The enhancement of an efficacy of an antibody (e.g., an anti-c-Met antibody) may include at least one selected from the group consisting of a synergistic effects obtained by targeting at least two antigen, improved properties as a medicament such as pharmacokinetic (PK) properties, increased stability in vivo or ex vivo, overcoming resistance to the antibody (e.g., an anti-c-Met antibody), decreased side effects (e.g., agonism) of the antibody (e.g., an anti-c-Met antibody), and the like.

In the method of enhancement of an efficacy of an antibody, the DARPin, the anti-EGFR DARPin, the antibody having an IgG form, the antibody having a scFv-Fc form IgG, and their linkage form are described as above.

Another embodiment provides a nucleic acid encoding the bispecific chimeric protein as described above. The nucleic acid may be provided in a vector. Therefore, another embodiment provides a recombinant vector comprising (carrying) the nucleic acid. The term "vector" may refer to a means for expressing a target gene in a host cell, as exemplified by a plasmid vector, a cozmid vector, and a viral vector such as a bacteriophage vector, adenovirus vector, retrovirus vector, and an adeno-related virus vector. In the recombinant vector, the nucleic acid may be operatively linked to a promoter. The term "operatively linked" as used herein is intended to pertain to a functional linkage between a nucleotide sequence of interest and an expression regulatory element (for example, a promoter sequence) so that the expression of the nucleotide sequence of interest is governed by the regulatory element. For instance, when it is "operatively linked" to the regulatory element, the nucleotide sequence of interest can be transcribed and/or translated under the control of the regulatory element. The recombinant vector may be constructed typically as a cloning vector or an expression vector. For recombinant expression vectors, a vector typically available for expressing a foreign protein in plant, animal or microorganism cells may be employed. Various methods well known in the art may be used for the construction of recombinant vectors.

Another embodiment provides a (recombinant) cell comprising (transfected with) the nucleic acid or the recombinant vector comprising the nucleic acid. in the recombinant vector may be inserted into a variety of hosts, such as prokaryotic cells (e.g., by transformation) or eukaryotic (e.g., by transfection) cells. Using a method well known in the art, (e.g., the nucleic acid or a recombinant vector carrying the nucleic acid may be introduced (incorporated) into a host cell. This transformation is carried out through $CaCl_2$ or electroporation when the host cell is prokaryotic. For eukaryotic host cells, the genetic introduction may be achieved using, but not limited to, microinjection, calcium phosphate precipitation, electroporation, liposome-mediated transfection, or particle bombardment. To select a transformed host cell, advantage may be taken of the phenotype attributed to a selection marker according to a method known in the art. For example, when the selection marker is a gene resistant to a certain antibiotic, the host cells may be grown in the presence of the antibiotic in a medium to select a transformant of interest.

The bispecific chimeric protein as described above may be produced by expressing the nucleic acid encoding the bispecific chimeric protein in the cell (e.g., by culturing the cell under the conditions allowing the expression of the nucleic acid) and optionally, isolating and/or purifying the expressed bispecific chimeric protein by general methods. Therefore, another embodiment provides a method of preparing the bispecific chimeric protein as described above, comprising expressing a nucleic acid encoding the bispecific chimeric protein in a cell.

The bispecific chimeric protein, for example, the bispecific chimeric protein including an anti-EGFR DARPin and an anti-c-Met antibody may have improved effects compared to the pre-existing antibody, for example, the pre-existing anti-c-Met antibody, as follows:

1. Establishment of platform of a bispecific chimeric protein having an IgG-DARPin form,
2. General utilization of anti-EGFR DARPins,
3. Inhibition of EGFR activity by new MOA (mechanism of action)
4. Synergistic anticancer effects compared to pre-existing anti-c-Met antibodies, anti-HER2 antibodies, or anti-EGFR antagonists.
5. Anticancer effects on cancer cells having resistance to pre-existing anti-c-Met antibodies, anti-HER2 antibodies, or anti-EGFR antagonists.

6. Presentation of a bispecific chimeric protein in an IgG-DARPins form displaying excellent effects compared to combination therapy using inhibitors of EGFR/MET, or EGFR/HER2.

Hereafter, the present invention will be described in detail by examples.

The following examples are intended merely to illustrate the invention and are not construed to restrict the invention.

EXAMPLES

Reference Example 1

Construction of Anti-c-Met Antibody 1.1. Production of "AbF46", a Mouse Antibody to c-Met
1.1.1. Immunization of Mouse To obtain immunized mice necessary for the development of a hybridoma cell line, each of five BALB/c mice (Japan SLC, Inc.), 4 to 6 weeks old, was intraperitoneally injected with a mixture of 100 μg of human c-Met/Fc fusion protein (R&D Systems) and one volume of complete Freund's adjuvant. Two weeks after the injection, a second intraperitoneal injection was conducted on the same mice with a mixture of 50 μg of human c-Met/Fc protein and one volume of incomplete Freund's adjuvant. One week after the second immunization, the immune response was finally boosted. Three days later, blood was taken from the tails of the mice and the sera were 1/1000 diluted in PBS and used to examine a titer of antibody to c-Met by ELISA. Mice found to have a sufficient antibody titer were selected for use in the cell fusion process.

1.1.2. Cell Fusion and Production of Hybridoma

Three days before cell fusion, BALB/c mice (Japan SLC, Inc.) were immunized with an intraperitoneal injection of a mixture of 50 μg of human c-Met/Fc fusion protein and one volume of PBS. The immunized mice were anesthetized before excising the spleen from the left half of the body. The spleen was meshed to separate splenocytes which were then suspended in a culture medium (DMEM, GIBCO, Invitrogen). The cell suspension was centrifuged to recover the cell layer. The splenocytes thus obtained ($1 \times 10^8$ cells) were mixed with myeloma cells (Sp2/0) ($1 \times 10^8$ cells), followed by spinning to give a cell pellet. The cell pellet was slowly suspended, treated with 45% polyethylene glycol (PEG) (1 mL) in DMEM for 1 min at 37° C., and supplemented with 1 mL of DMEM. To the cells was added 10 mL of DMEM over 10 min, after which incubation was conducted in a water bath at 37° C. for 5 min. Then the cell volume was adjusted to 50 mL before centrifugation. The cell pellet thus formed was resuspended at a density of $1 \sim 2 \times 10^5$ cells/mL in a selection medium (HAT medium) and 0.1 mL of the cell suspension was allocated to each well of 96-well plates which were then incubated at 37° C. in a $CO_2$ incubator to establish a hybridoma cell population.

1.1.3. Selection of Hybridoma Cells Producing Monoclonal Antibodies to c-Met Protein From the hybridoma cell population established in Reference Example 1.1.2, hybridoma cells which showed a specific response to c-Met protein were screened by ELISA using human c-Met/Fc fusion protein and human Fc protein as antigens.

Human c-Met/Fc fusion protein was seeded in an amount of 50 μL (2 μg/mL)/well to microtiter plates and allowed to adhere to the surface of each well. The antibody that remained unbound was removed by washing. For use in selecting the antibodies that do not bind c-Met but recognize Fc, human Fc protein was attached to the plate surface in the same manner.

The hybridoma cell culture obtained in Reference Example 1.1.2 was added in an amount of 50 μL to each well of the plates and incubated for 1 hour. The cells remaining unreacted were washed out with a sufficient amount of Tris-buffered saline and Tween 20 (TBST). Goat anti-mouse IgG-horseradish peroxidase (HRP) was added to the plates and incubated for 1 hour at room temperature. The plates were washed with a sufficient amount of TBST, followed by reacting the peroxidase with a substrate (OPD). Absorbance at 450 nm was measured on an ELISA reader.

Hybridoma cell lines which secrete antibodies that specifically and strongly bind to human c-Met but not human Fc were selected repeatedly. From the hybridoma cell lines obtained by repeated selection, a single clone producing a monoclonal antibody was finally separated by limiting dilution. The single clone of the hybridoma cell line producing the monoclonal antibody was deposited with the Korean Cell Line Research Foundation, an international depository authority located at Yungun-Dong, Jongno-Gu, Seoul, Korea, on Oct. 9, 2009, with Accession No. KCLRF-BP-00220 according to the Budapest Treaty (refer to Korean Patent Laid-Open Publication No. 2011-0047698).

1.1.4. Production and Purification of Monoclonal Antibody

The hybridoma cell line obtained in Reference Example 1.1.3 was cultured in a serum-free medium, and the monoclonal antibody (AbF46) was produced and purified from the cell culture.

First, the hybridoma cells cultured in 50 mL of a medium (DMEM) supplemented with 10% (v/v) FBS were centrifuged and the cell pellet was washed twice or more with 20 mL of PBS to remove the FBS therefrom. Then, the cells were resuspended in 50 mL of DMEM and incubated for 3 days at 37° C. in a $CO_2$ incubator.

After the cells were removed by centrifugation, the supernatant was stored at 4° C. before use or immediately used for the separation and purification of the antibody. An AKTA system (GE Healthcare) equipped with an affinity column (Protein G agarose column; Pharmacia, USA) was used to purify the antibody from 50 to 300 mL of the supernatant, followed by concentration with an filter (Amicon). The antibody in PBS was stored before use in the following examples.

1.2. Construction of chAbF46, a Chimeric Antibody to c-Met

A mouse antibody is apt to elicit immunogenicity in humans. To solve this problem, chAbF46, a chimeric antibody, was constructed from the mouse antibody AbF46 produced in Experimental Example 1.1.4 by replacing the constant region, but not the variable region responsible for antibody specificity, with an amino sequence of the human IgG1 antibody.

In this regard, a gene was designed to include the nucleotide sequence of "EcoRI-signal sequence-VH-NheI-CH-TGA-XhoI" (SEQ ID NO: 38) for a heavy chain and the nucleotide sequence of "EcoRI-signal sequence-VL-BsiWI-CL-TGA-XhoI" (SEQ ID NO: 39) for a light chain and synthesized. Then, a DNA fragment having the heavy chain nucleotide sequence (SEQ ID NO: 38) and a DNA fragment having the light chain nucleotide sequence (SEQ ID NO: 39) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen), and a pcDNA™3.3-TOPO TA Cloning Kit (Cat no. 8300-01), respectively.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5\times10^5$ cells/ml, and after 24 hours, when the cell number reached to $1\times10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

Afterwards, the cells were incubated in DMEM supplemented with 10% (v/v) FBS for 5 hours at 37° C. under a 5% $CO_2$ condition and then in FBS-free DMEM for 48 hours at 37° C. under a 5% $CO_2$ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a chimeric antibody AbF46 (hereinafter referred to as "chAbF46").

1.3. Construction of Humanized Antibody huAbF46 from Chimeric Antibody chAbF46

1.3.1. Heavy Chain Humanization

To design two domains H1-heavy and H3-heavy, human germline genes which share the highest identity/homology with the VH gene of the mouse antibody AbF46 purified in Reference Example 1.2 were analyzed. An Ig BLAST (www.ncbi.nlm.nih.gov/igblast/) result revealed that VH3-71 has an identity/identity/homology of 83% at the amino acid level. CDR-H1, CDR-H2, and CDR-H3 of the mouse antibody AbF46 were defined according to Kabat numbering. A design was made to introduce the CDR of the mouse antibody AbF46 into the framework of VH3-71. Hereupon, back mutations to the amino acid sequence of the mouse AbF46 were conducted at positions 30 (S→T), 48 (V→L), 73 (D→N), and 78 (T→L). Then, H1 was further mutated at positions 83 (R→K) and 84 (A→T) to finally establish H1-heavy (SEQ ID NO: 40) and H3-heavy (SEQ ID NO: 41).

For use in designing H4-heavy, human antibody frameworks were analyzed by a BLAST search. The result revealed that the VH3 subtype, known to be most stable, is very similar in framework and sequence to the mouse antibody AbF46. CDR-H1, CDR-H2, and CDR-H3 of the mouse antibody AbF46 were defined according to Kabat numbering and introduced into the VH3 subtype to construct H4-heavy (SEQ ID NO: 42).

1.3.2. Light Chain Humanization

To design two domains H1-light (SEQ ID NO: 43) and H2-light (SEQ ID NO: 44), human germline genes which share the highest identity/homology with the VH gene of the mouse antibody AbF46 were analyzed. An Ig BLAST search result revealed that VK4-1 has a identity/homology of 75% at the amino acid level. CDR-L1, CDR-L2, and CDR-L3 of the mouse antibody AbF46 were defined according to Kabat numbering. A design was made to introduce the CDR of the mouse antibody AbF46 into the framework of VK4-1. Hereupon, back mutations to the amino acid sequence of the mouse AbF46 were conducted at positions 36 (Y→H), 46 (L→M), and 49 (Y→I). Only one back mutation was conducted at position 49 (Y→I) on H2-light.

To design H3-light (SEQ ID NO: 45), human germline genes which share the highest identity/homology with the VL gene of the mouse antibody AbF46 were analyzed by a search for BLAST. As a result, VK2-40 was selected. VL and VK2-40 of the mouse antibody AbF46 were found to have a identity/homology of 61% at an amino acid level. CDR-L1, CDR-L2, and CDR-L3 of the mouse antibody were defined according to Kabat numbering and introduced into the framework of VK4-1. Back mutations were conducted at positions 36 (Y→H), 46 (L→M), and 49 (Y→I) on H3-light.

For use in designing H4-light (SEQ ID NO: 46), human antibody frameworks were analyzed. A Blast search revealed that the Vk1 subtype, known to be the most stable, is very similar in framework and sequence to the mouse antibody AbF46. CDR-L1, CDR-L2, and CDR-L3 of the mouse antibody AbF46 were defined according to Kabat numbering and introduced into the Vk1 subtype. Hereupon, back mutations were conducted at positions 36 (Y→H), 46 (L→M), and 49 (Y→I) on H4-light.

Thereafter, DNA fragments having the heavy chain nucleotide sequences (H1-heavy: SEQ ID NO: 47, H3-heavy: SEQ ID NO: 48, H4-heavy: SEQ ID NO: 49) and DNA fragments having the light chain nucleotide sequences (H1-light: SEQ ID NO: 50, H2-light: SEQ ID NO: 51, H3-light: SEQ ID NO: 52, H4-light: SEQ ID NO: 53) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™3.3-TOPO TA Cloning Kit (Cat no. 8300-01), respectively, so as to construct recombinant vectors for expressing a humanized antibody.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. One day before the transient expression, the cells were provided in the concentration of $5\times10^5$ cells/ml, and after 24 hours, when the cell number reached to $1\times10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a humanized antibody AbF46 (hereinafter referred to as "huAbF46"). The humanized antibody huAbF46 used in the following examples included a combination of H4-heavy (SEQ ID NO: 42) and H4-light (SEQ ID NO: 46).

1.4. Construction of scFV Library of huAbF46 Antibody

For use in constructing an scFv of the huAbF46 antibody from the heavy and light chain variable regions of the huAbF46 antibody, a gene was designed to have the structure of "VH-linker-VL" for each of the heavy and the light chain variable region, with the linker having the amino acid sequence "GLGGLGGGGSGGGGSGGSSGVGS" (SEQ ID NO: 54). A polynucleotide sequence (SEQ ID NO: 55) encoding the designed scFv of huAbF46 was synthesized in Bioneer and an expression vector for the polynucleotide had the nucleotide sequence of SEQ ID NO: 56.

After expression, the product was found to exhibit specificity to c-Met.

1.5. Construction of Library Genes for Affinity Maturation 1.5.1. Selection of Target CDRs and Synthesis of Primers The affinity maturation of huAbF46 was achieved. First, six complementary determining regions (CDRs) were defined according to Kabat numbering. The CDRs are given in Table 1, below.

TABLE 1

| CDR | Amino Acid Sequence |
|---|---|
| CDR-H1 | DYYMS (SEQ ID NO: 1) |
| CDR-H2 | FIRNKANGYTTEYSASVKG (SEQ ID NO: 2) |
| CDR-H3 | DNWFAY (SEQ ID NO: 3) |
| CDR-L1 | KSSQSLLASGNQNNYLA (SEQ ID NO: 10) |
| CDR-L2 | WASTRVS (SEQ ID NO: 11) |
| CDR-L3 | QQSYSAPLT (SEQ ID NO: 12) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of huAbF46 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

1.5.2. Construction of a Library of huAbF46 Antibodies and Affinity for c-Met

The construction of antibody gene libraries through the introduction of random sequences was carried out using the primers synthesized in the same manner as in Reference Example 1.5.1. Two PCR products were obtained using a polynucleotide covering the scFV of huAbF46 as a template, and were subjected to overlap extension PCR to give scFv library genes for huAbF46 antibodies in which only desired CDRs were mutated. Libraries targeting each of the six CDRs prepared from the scFV library genes were constructed.

The affinity for c-Met of each library was compared to that of the wildtype. Most libraries were lower in affinity for c-Met, compared to the wild-type. The affinity for c-Met was retained in some mutants.

1.6. Selection of Antibody with Improved Affinity from Libraries

After maturation of the affinity of the constructed libraries for c-Met, the nucleotide sequence of scFv form each clone was analyzed. The nucleotide sequences thus obtained are summarized in Table 2 and were converted into IgG forms. Four antibodies which were respectively produced from clones L3-1, L3-2, L3-3, and L3-5 were used in the subsequent experiments.

TABLE 2

| Clone | Library constructed | CDR Sequence |
|---|---|---|
| H11-4 | CDR-H1 | PEYYMS (SEQ ID NO: 22) |
| YC151 | CDR-H1 | PDYYMS (SEQ ID NO: 23) |
| YC193 | CDR-H1 | SDYYMS (SEQ ID NO: 24) |
| YC244 | CDR-H2 | RNNANGNT (SEQ ID NO: 25) |
| YC321 | CDR-H2 | RNKVNGYT (SEQ ID NO: 26) |
| YC354 | CDR-H3 | DNWLSY (SEQ ID NO: 27) |
| YC374 | CDR-H3 | DNWLTY (SEQ ID NO: 28) |
| L1-1 | CDR-L1 | KSSHSLLASGNQNNYLA (SEQ ID NO: 29) |
| L1-3 | CDR-L1 | KSSRSLLSSGNHKNYLA (SEQ ID NO: 30) |
| L1-4 | CDR-L1 | KSSKSLLASGNQNNYLA (SEQ ID NO: 31) |
| L1-12 | CDR-L1 | KSSRSLLASGNQNNYLA (SEQ ID NO: 32) |
| L1-22 | CDR-L1 | KSSHSLLASGNQNNYLA (SEQ ID NO: 33) |
| L2-9 | CDR-L2 | WASKRVS (SEQ ID NO: 34) |
| L2-12 | CDR-L2 | WGSTRVS (SEQ ID NO: 35) |
| L2-16 | CDR-L2 | WGSTRVP (SEQ ID NO: 36) |
| L3-1 | CDR-L3 | QQSYSRPYT (SEQ ID NO: 13) |
| L3-2 | CDR-L3 | GQSYSRPLT (SEQ ID NO: 14) |
| L3-3 | CDR-L3 | AQSYSHPFS (SEQ ID NO: 15) |
| L3-5 | CDR-L3 | QQSYSRPFT (SEQ ID NO: 16) |
| L3-32 | CDR-L3 | QQSYSKPFT (SEQ ID NO: 37) |

1.7. Conversion of Selected Antibodies into IgG

Respective polynucleotides encoding heavy chains of the four selected antibodies were designed to have the structure of "EcoRI-signal sequence-VH-NheI-CH-XhoI" (SEQ ID NO: 38). The heavy chains of huAbF46 antibodies were used as they were because their amino acids were not changed during affinity maturation. In the case of the hinge region, however, the U6-HC7 hinge (SEQ ID NO: 57) was employed instead of the hinge of human IgG1. Genes were also designed to have the structure of "EcoRI-signal sequence-VL-BsiWI-CL-XhoI" for the light chain. Polypeptides encoding light chain variable regions of the four antibodies which were selected after the affinity maturation were synthesized in Bioneer. Then, a DNA fragment having the heavy chain nucleotide sequence (SEQ ID NO: 38) and DNA fragments having the light chain nucleotide sequences (DNA fragment including L3-1-derived CDR-L3: SEQ ID NO: 58, DNA fragment including L3-2-derived CDR-L3: SEQ ID NO: 59, DNA fragment including L3-3-derived CDR-L3: SEQ ID NO: 60, and DNA fragment including L3-5-derived CDR-L3: SEQ ID NO: 61) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™3.3-TOPO TA Cloning Kit (Cat no. 8300-01), respectively, so as to construct recombinant vectors for expressing affinity-matured antibodies.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify four affinity-matured antibodies (hereinafter referred to as "huAbF46-H4-A1 (L3-1 origin), huAbF46-H4-A2 (L3-2 origin), huAbF46-H4-A3 (L3-3 origin), and huAbF46-H4-A5 (L3-5 origin)," respectively).

1.8. Construction of Constant Region- and/or Hinge Region-Substituted huAbF46-H4-A1

Among the four antibodies selected in Reference Example 1.7, huAbF46-H4-A1 was found to be the highest in affinity for c-Met and the lowest in Akt phosphorylation and c-Met degradation degree. In the antibody, the hinge region, or the constant region and the hinge region, were substituted.

The antibody huAbF46-H4-A1 (U6-HC7) was composed of a heavy chain including the heavy chain variable region of huAbF46-H4-A1, U6-HC7 hinge, and the constant region of human IgG1 constant region, and a light chain including the light chain variable region of huAbF46-H4-A1 and human kappa constant region. The antibody huAbF46-H4-A1 (IgG2 hinge) was composed of a heavy chain including a heavy chain variable region, a human IgG2 hinge region, and a human IgG1 constant region, and a light chain including the light chain variable region of huAbF46-H4-A1 and a human kappa constant region. The antibody huAbF46-H4-A1 (IgG2 Fc) was composed of the heavy chain variable region of huAbF46-H4-A1, a human IgG2 hinge region, and a human IgG2 constant region, and a light chain including the light variable region of huAbF46-H4-A1 and a human kappa constant region. Hereupon, the histidine residue at position 36 on the human kappa constant region of the light chain was changed to tyrosine in all of the three antibodies to increase antibody production.

For use in constructing the three antibodies, a polynucleotide (SEQ ID NO: 63) encoding a polypeptide (SEQ ID NO: 62) composed of the heavy chain variable region of huAbF46-H4-A1, a U6-HC7 hinge region, and a human IgG1 constant region, a polynucleotide (SEQ ID NO: 65) encoding a polypeptide (SEQ ID NO: 64) composed of the heavy chain variable region of huAbF46-H4-A1, a human IgG2 hinge region, and a human IgG1 region, a polynucleotide (SEQ ID NO: 67) encoding a polypeptide (SEQ ID NO: 66) composed of the heavy chain variable region of huAbF46-H4-A1, a human IgG2 region, and a human IgG2 constant region, and a polynucleotide (SEQ ID NO: 69) encoding a polypeptide (SEQ ID NO: 68) composed of the light chain variable region of huAbF46-H4-A1, with a tyrosine residue instead of histidine at position 36, and a human kappa constant region were synthesized in Bioneer. Then, the DNA fragments having heavy chain nucleotide sequences were inserted into a pOptiVEC™-TOPO TA Cloning Kit enclosed in an OptiCHO™ Antibody Express Kit (Cat no. 12762-019, Invitrogen) while DNA fragments having light chain nucleotide sequences were inserted into a pcDNA™3.3-TOPO TA Cloning Kit (Cat no. 8300-01) so as to construct vectors for expressing the antibodies.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with IgG elution buffer (Thermo Scientific, 21004). The buffer was exchanged with PBS to finally purify three antibodies (huAbF46-H4-A1 (U6-HC7), huAbF46-H4-A1 (IgG2 hinge), and huAbF46-H4-A1 (IgG2 Fc)). Among the three antibodies, huAbF46-H4-A1 (IgG2 Fc) was representatively selected for the following examples, and referred as L3-1Y-IgG2.

Example 1

Preparation of an Anti-c-Met/Anti-EGFR DARPin Bispecific Chimeric Protein 1

Figure 3:
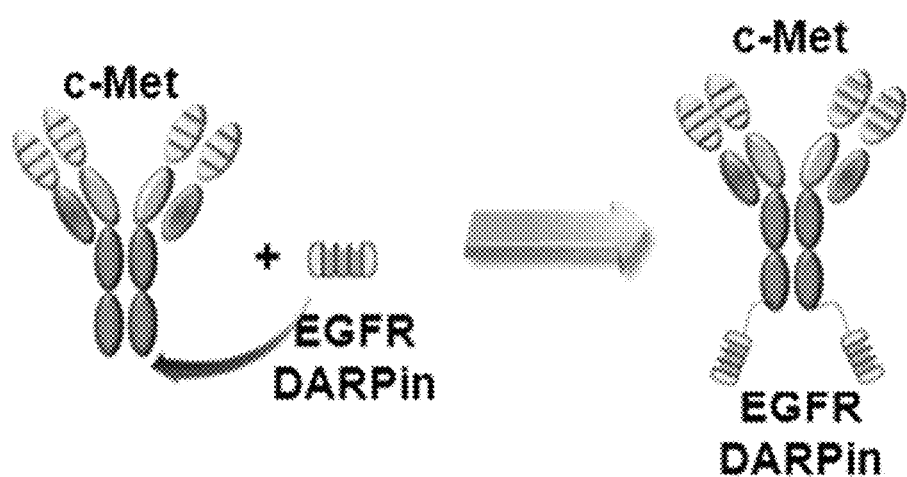
FIG. 3 is a schematic depicting a process of preparing an anti-c-Met/anti-EGFR bispecific chimeric protein according to an embodiment.

Each of the 4 anti-EGFR DARPins (SEQ ID NOs: 109, 110, 111, and 112) was fused to the C-terminus of the L3-1Y-IgG2 prepared in Reference Example 1, to prepare 4 kinds of anti-c-Met antibody/anti-EGFR DARPin fusion complexes (i.e., anti-c-Met/anti-EGFR bispecific chimeric proteins) (FIG. 3). The heavy chain of L3-1Y-IgG2 antibody and the anti-EGFR DARPin were linked to each other through a peptide linker having 10 amino acids (GGGGSGGGGS; $(G4S)_2$ (SEQ ID NO. 152)), to give 'L3-1Y-IgG2 heavy chain—(G4S)2—anti-EGFR DARPins' form.

The binding affinities to EGFR of The 4 kinds of anti-c-Met/anti-EGFR bispecific chimeric proteins were examined by Biacore (see following Example 2), to select one which has highest affinity to EGFR(R&D systems). The selected bispecific chimeric protein was named as ME-19 (including E01 DARPin (SEQ ID NO: 109)).

Example 2

Examination of Properties and EGFR Affinity of the Anti-c-Met/Anti-EGFR DARPin Bispecific Chimeric Protein To examine properties of the bispecific chimeric protein ME-19 (anti-c-Met/anti-EGFR bispecific chimeric protein) prepared in Example 1, 20 ug of the bispecific chimeric protein was injected to a HPLC system (WATERS 2695) equipped with TSKG3000SWXL column (Tosho) to the velocity of 0.5 ml/min, to conduct a Size Exclusion Chromatography.

Figure 4:
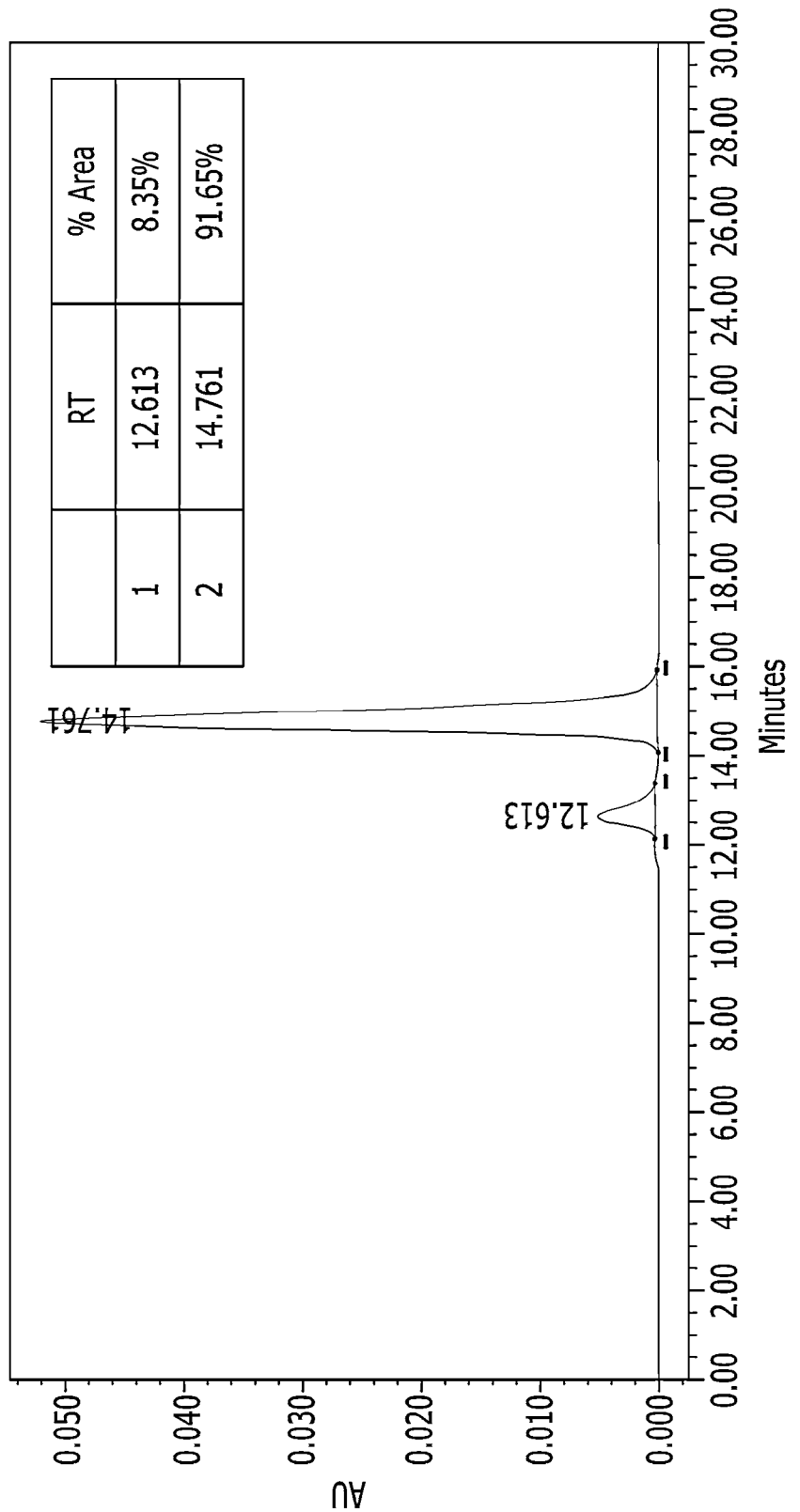
FIG. 4 is a graph displaying the stability properties of an anti-c-Met/anti-EGFR bispecific chimeric protein in solution according to an embodiment.

The obtained results are shown in FIG. 4. In FIG. 4, "1" refers to a quantitative value of the peak for a soluble dimer, and "2" refers to a quantitative value of the peak for a monomer. As shown in FIG. 4, the selected bispecific chimeric protein ME-19 forms a slight amount of soluble dimer (<10%), which demonstrates that the bispecific chimeric protein is a very stable molecule.

The binding affinity of bispecific chimeric protein ME-19 to each of the two antigens c-Met and EGFR was examined using Biacore T100 (GE). Human Fab binder (GE Healthcare) was immobilized on the surface of CM5 chip (#BR-1005-30, GE) according to the manufacturer's manual. About 90~120 RU of the bispecific chimeric protein ME-19 was captured, and various concentrations of EGFR-Fc (#344-ER, R&D Systems) were added to the captured bispecific chimeric protein. 10 mM Glycine-HCl (pH 1.5) solution was added hereto, to regenerate the surface. To determine the affinity, the obtained data were fitted using BIA evaluation software (GE Healthcare, Biacore T100 evaluation software).

The obtained results are shown in Table 3.

TABLE 3

| Antibody | Antigen | $K_D$ (nM) | $K_a$ (1/Ms) | $K_d$ (1/s) |
|---|---|---|---|---|
| ME19 | EGFR | 0.35 | $1.8 \times 10^5$ | $6.4 \times 10^{-5}$ |

As shown in Table 3, the bispecific chimeric protein ME-19 prepared in Example 1 exhibits very high affinity to EGFR as KD=0.35 nM as measured by Biacore.

Example 3

EGF Competition Test of the Anti-c-Met/Anti-EGFR DARPin Bispecific Chimeric Protein In order to confirm whether or not the bispecific chimeric protein ME-19 prepared in Example 1 competes with EGF, a competition assay was conducted using ELISA. 96-well immunoplate (Nunc) was coated with EGFR (#344-ER, R&D Systems) in the amount of 0.25 µg/well. Then, 20 ng/ml of biotinylated EGF (invitrogen) and serially diluted ME-19 were mixed and the mixture was inoculated on the plate and reacted at room temperature for 2 hours. The resulted reacting product was washed with PBS containing 0.05% (w/v) of Tween 20. HRP (Horse radish peroxidase) conjugated anti-streptavidin antibody (#21140, Thermo scientific) was added to the each well and reacted at room temperature for 1 hour. After washing as above, TMB substrate (eBioscience) was added to the each well for inducing color reaction, and then absorbance at 405 nm was measured. For comparison, the same examination as above except using Erbitux (Merck) instead of the bispecific chimeric protein ME-19 was conducted.

Figure 5:
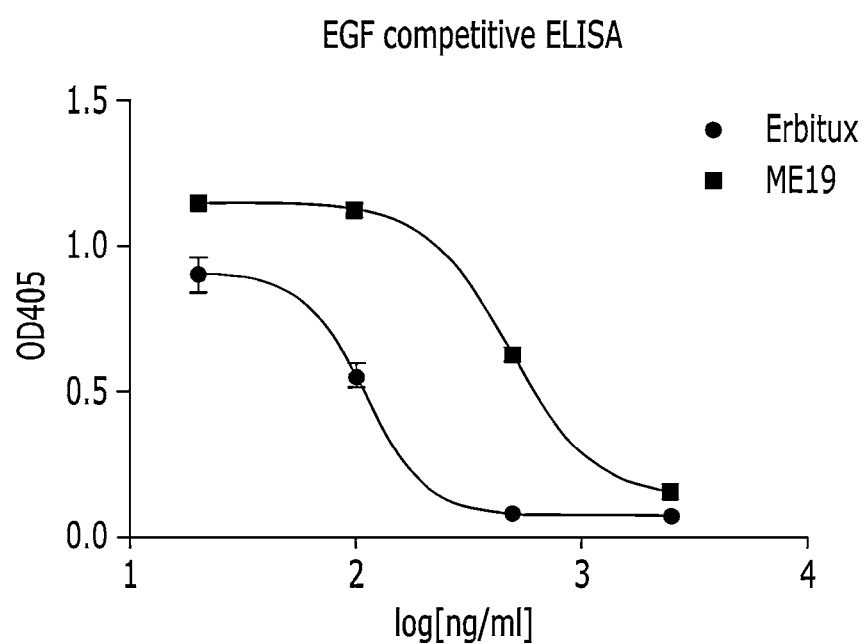
FIG. 5 is a graph displaying the competition of an anti-c-Met/anti-EGFR bispecific chimeric protein with EGF in a competitive ELISA assay according to an embodiment.

The obtained results are shown in FIG. 5. As shown in FIG. 5, the bispecific chimeric protein ME-19 competes with EGF.

Example 4

Examination of EGFR Phosphorylation Inhibition of the Anti-c-Met/Anti-EGFR DARPin Bispecific Chimeric Protein In order to examine the EGFR phosphorylation inhibition effect of the bispecific chimeric protein ME-19 prepared in Example 1, phospho-EGFR test was conducted using human epidermoid carcinoma, A431 cell line, where c-Met is expressed at a low level. A431 cells (ATCC) were inoculated on 96-well cell culture plate in the amount of $2 \times 10^4$ cells/well, and incubated in RPMI1640 medium (#11875-093, Gibco) supplemented with 10% (v/v) FBS and 1% (v/v) Penicillin-Streptomycin under the conditions of 5% $CO_2$ and 37° C. for 24 hours. After removing medium from the obtained cell culture, serum-free medium (#30-2002, ATCC) was added to the cell culture, and the cell culture was further cultured for 18 hours. The cultured cells were treated with 5 µg/ml of the bispecific chimeric protein ME-19 and further cultured for 30 minutes, then, treated with 200 ng/ml of EGF (R&D systems) and further cultured for 30 minutes. After lysis of the cultured cells, the degree of EGFR phosphorylation was determined by measuring the absorbance at 405 nm using phospho-EGFR detection kit (Cell signaling). For comparison, the same examination as above except using Erbitux (#ET509081213, Merck) (positive control) instead of the bispecific chimeric protein ME-19 was conducted.

Figure 6:
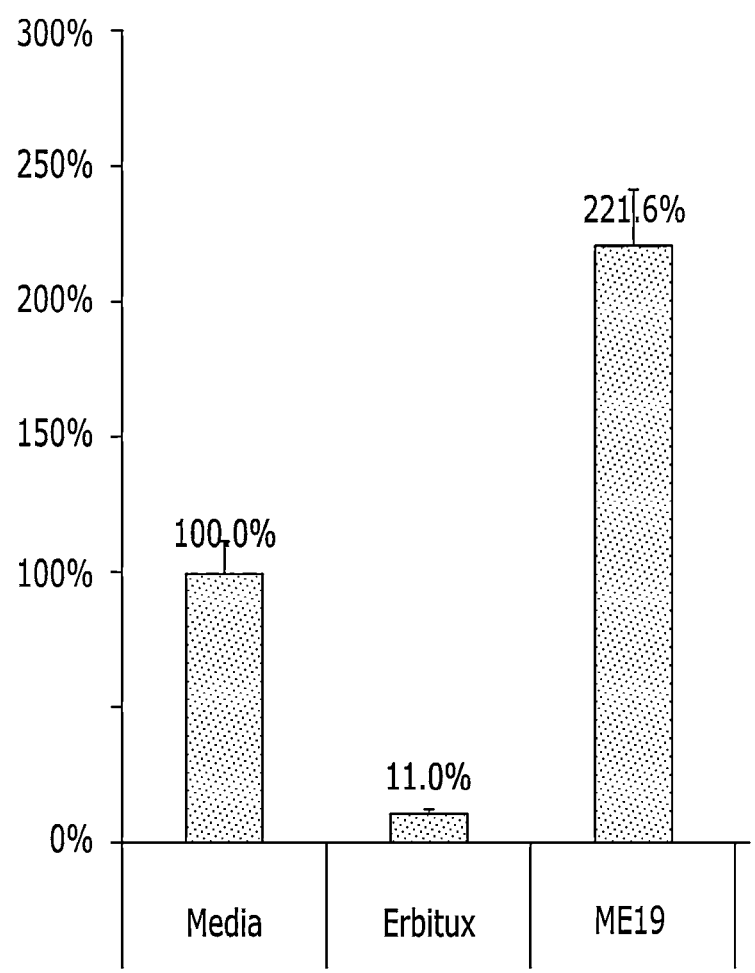
FIG. 6 is a graph displaying the degree of EGFR phosphorylation inhibition in A431 cells by an anti-c-Met/anti-EGFR bispecific chimeric protein according to an embodiment.

The obtained results are shown in FIG. 6. In FIG. 6, "media" refers to the case treated with no antibody. As shown in FIG. 6, in A431 cells having low expression of c-Met, the EGFR phosphorylation is increased by ME-19 compared to the case treated with natural EGF only (media). These results suggest that EGFR signal pathway is perturbed (i.e., disrupted) with hyper phosphorylation of EGFR by ME-19 in A431 cells.

Example 5

Examination of Cell Proliferation Inhibition of the Anti-c-Met/Anti-EGFR DARPin Bispecific Chimeric Protein In order to examine the cancer cell proliferation inhibition effect of the bispecific chimeric protein ME-19 prepared in Example 1, the degree of cell proliferation was tested in SNU5 cell line (KCLB No. 00005), MKN45 cell line (KCLB No. 80103), H1993 cell line (ATCC CRL-5909) and A431 cell line (ATCC).

All the cells were cultured in RPMI1640 medium (#11875-093, Gibco) supplemented with 10% (v/v) FBS and 1% (v/v) Penicillin-Streptomycin under the conditions of 5% $CO_2$ and 37° C. To conduct cell proliferation assay, each cell line was sub-cultured in 96-well plate at the concentration of $1 \times 10^4$ cell/well, treated with the anti-c-Met/anti-EGFR DARPin bispecific chimeric protein ME-19 prepared in Example 1 at the amount of 5 ug (microgram)/ml, and further cultured for 72 hours. A group treated with no antibody was used as a negative control. Groups treated with commercially obtained EGFR inhibitors Erlotinib (represented as "Er"; #S1023, Selleckchem; 2 uM (micromole)), Erbitux (represented as "Ebt"; #ET509081213, Merck; 5 µg/ml), 5 µg/ml of L3-1Y-IgG2 antibody prepared in Reference Example 1, or a combination of L3-1Y-IgG2 antibody prepared in Reference Example 1 and Erbitux were used as positive controls.

After culturing, the cell proliferation was measured by Cell Counting Kit-8 assay (Dojindo Molecular Technologies, Gaithersburg, Md.) according to the manufacturer's manual. In brief, after culturing for 72 hours, 10 ul (microliter) of CCK8 solution was added to each well, and further cultured 2.5 hours. Then, the absorbance at 450 nm was measured using microplate reader.

Figure 7:
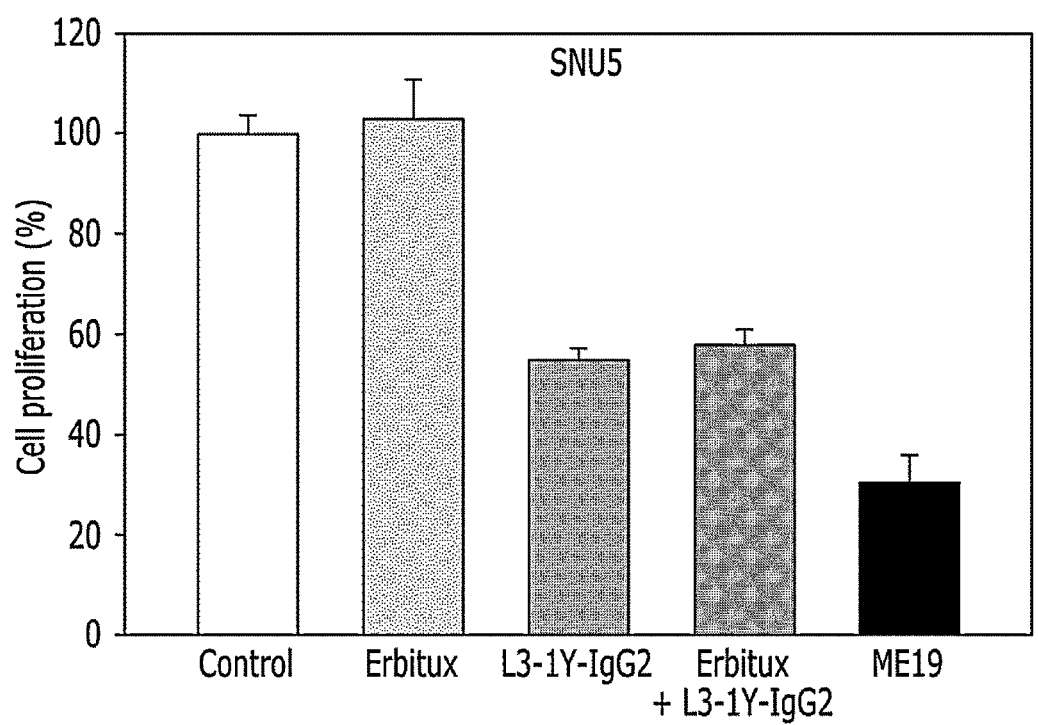
FIG. 7 is a graph displaying the degree of proliferation inhibition of SNU5 cells by an anti-c-Met/anti-EGFR bispecific chimeric protein according to an embodiment.
Figure 8:
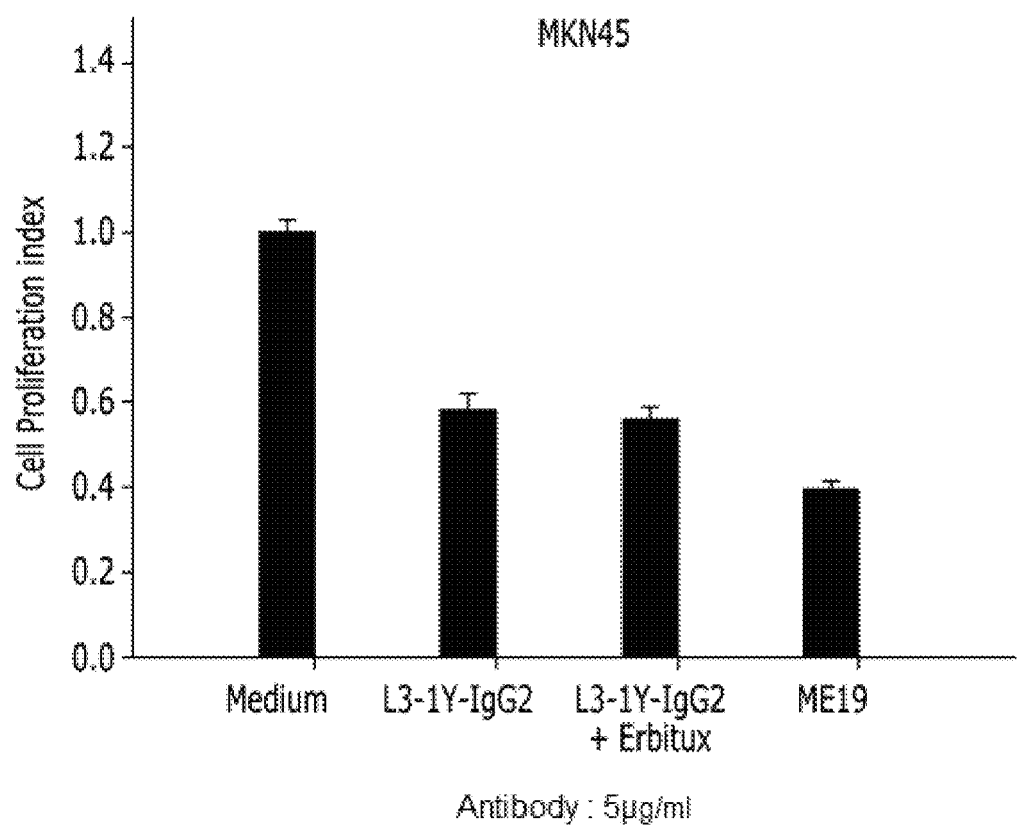
FIG. 8 is a graph displaying the degree of proliferation inhibition of MKN45 cells by an anti-c-Met/anti-EGFR bispecific chimeric protein according to an embodiment.
Figure 9:
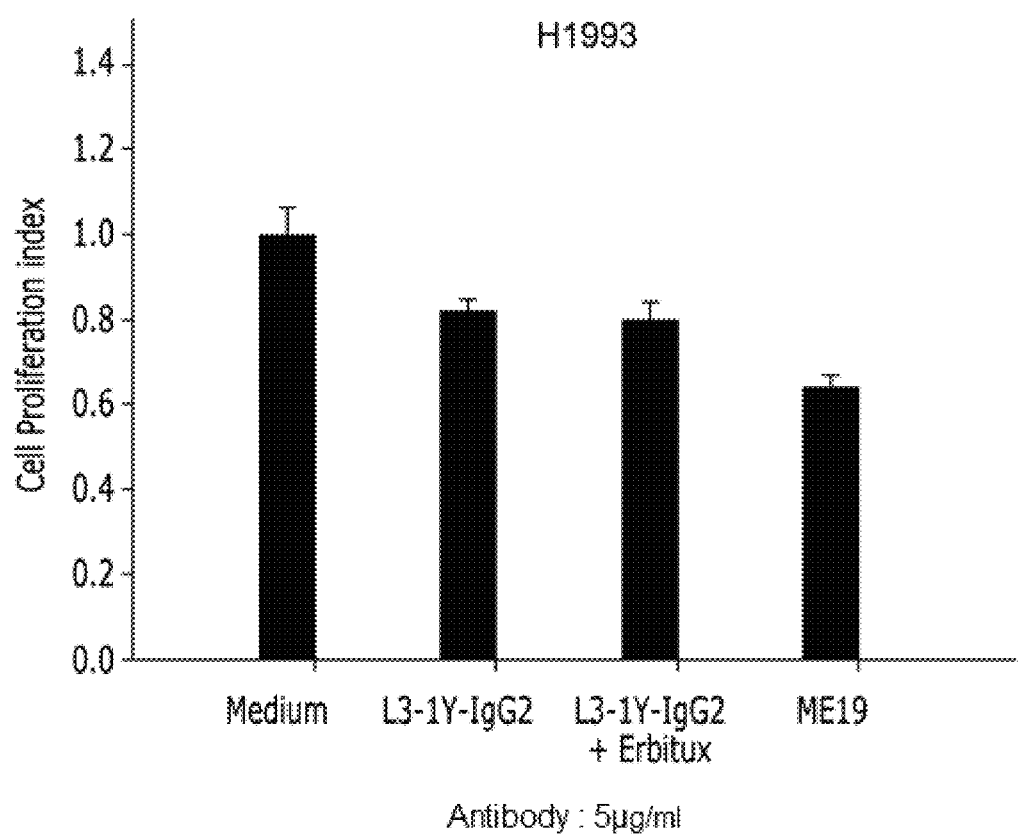
FIG. 9 is a graph displaying the degree of proliferation inhibition of H1993 cells by an anti-c-Met/anti-EGFR bispecific chimeric protein according to an embodiment.
Figure 10:
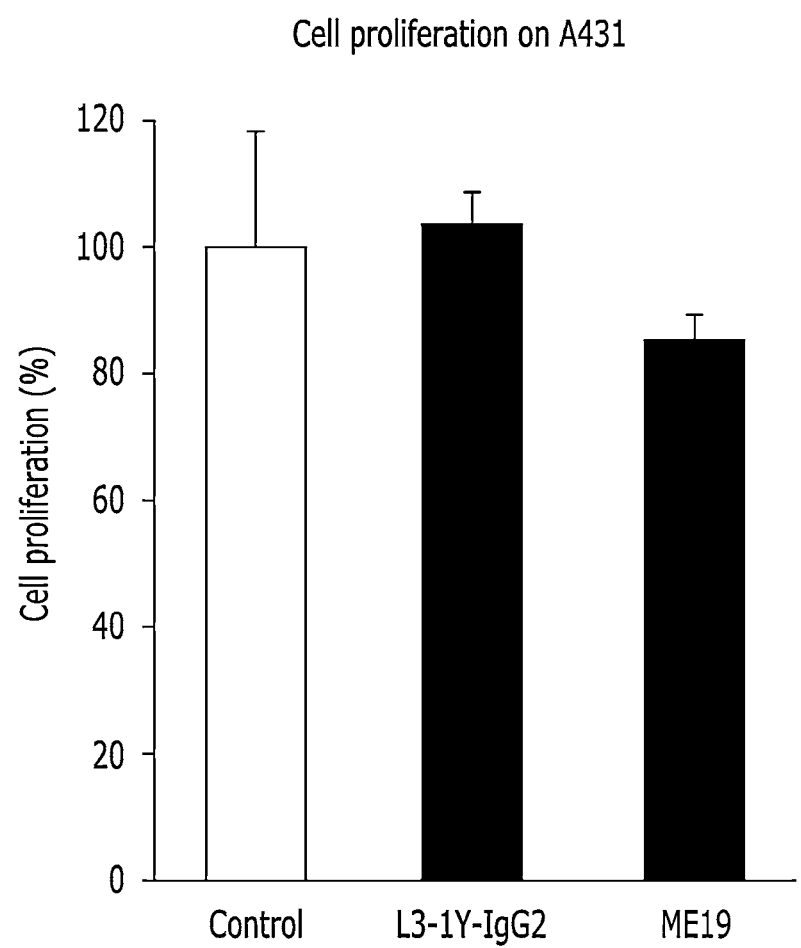
FIG. 10 is a graph displaying the degree of proliferation inhibition of A431 cells by an anti-c-Met/anti-EGFR bispecific chimeric protein according to an embodiment.

The obtained results are shown in FIG. 7 (SNU5), FIG. 8 (MKN45), FIG. 9 (H1993), and FIG. 10 (A431), respectively. In FIGS. 7 and 10, "control" refers to a medium treated with no antibody, and in FIGS. 8 and 9, "Cell proliferation index" on Y-axis refers to a value for cell proliferation measured by CCK8. As shown in FIGS. 7-9, in gastric cancer cell lines such as SNU5 and MKN45 where c-Met is overexpressed and H1993 cell line where both of c-Met and EGFR are overexpressed, ME-19 demonstrates exhibits excellent anticancer effects (cancer cell proliferation inhibition effect) compared to L3-1Y-IgG2, Erbitux, and the combination thereof. In addition, as shown in FIG. 10, ME-19 also exhibits excellent anticancer effect even on A431 where c-Met is expressed at a low level, compared to L3-1Y-IgG2.

Example 6

Internalization of c-Met and EGFR by the Anti-c-Met/Anti-EGFR DARPin Bispecific Chimeric Protein Gastric cancer cell line MKN45 (KCLB No. 80103) was provided at the amount of $4 \times 10^4$ cell/well. To the cells, L3-1Y-IgG2 prepared Reference Example 1, cetuximab (#ET509081213, Merck), and ME-19 prepared in Example 1 were treated alone or in combination at the amount of 1 µg/ml per each well (when treated in combination, each treated amount is 1 µg/ml), and incubated at 37° C. for 2 hours. The incubated cells were treated with 4% (v/v) formaldehyde for 15 minutes, to be immobilized on plate, and then, washed three times with PBS. Thereafter, the resulted cells were treated with blocking buffer (0.5% (v/v) triton x-100 and 5% (v/v) donkey serum) for 1 hour, and then, with primary antibodies respectively against c-Met and EGFR (primary antibody for c-Met; #FAB3582A, R&D systems, primary antibody for EGFR; #5616, Cell signaling) at the amount of 100 ul (microliter) (1:100 diluted) at 4° C. for 15 hours. The resultant was washed three times with PBS, treated with secondary antibody (#A21433, Invitrogen) at the amount of 100 ul (1:2000 diluted) at room temperature for 1 hour, and washed again three times with PBS, to prepare a plate with mounting medium (#H-1200, Vector). The cells in the prepared plate were observed by a confocal microscope (Zeiss, LSM710).

Figure 11:
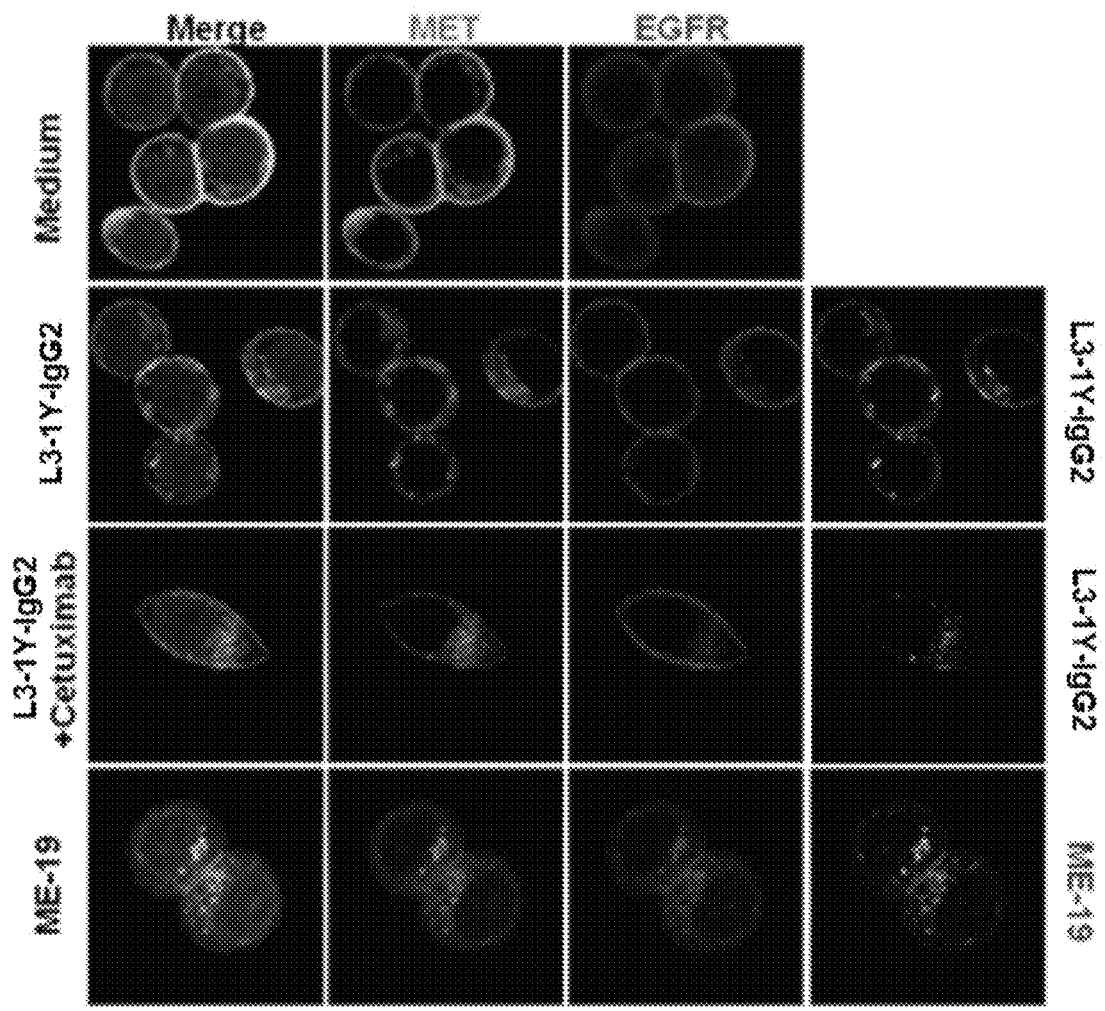
FIG. 11 is a fluorescent image depicting the internalization of c-Met and EGFR by an anti-c-Met/anti-EGFR bispecific chimeric protein according to an embodiment.

The obtained results are shown in FIG. 11. As shown in FIG. 11, when L3-1Y-IgG2 is treated alone, only c-Met moves into a cell (internalized) and EGFR is still remained on cell membrane, whereas when ME-19 is treated, both of c-Met and EGFR move into a cell.

In conclusion, the anti-c-Met/anti-EGFR DARPin bispecific chimeric protein with an anti-EGFR DARPin inhibits EGFR and c-Met functions by different mechanism from that of pre-existing anti-EGFR or anti-c-Met antibody.

Example 7

Decreased Expression of Target Receptor by the Anti-c-Met/Anti-EGFR DARPin Bispecific Chimeric Protein To confirm the decreased expression of the target receptors, c-Met and EGFR, by the anti-c-Met/anti-EGFR DARPin bispecific chimeric protein, human gastric cancer cell lines MKN45 (KCLB No. 80103) and SNU638 (ATCC) were respectively sub-cultured at the amount of $2 \times 10^3$ cells/well in 96-well plate, treated with 5 µg/ml of L3-1Y-IgG2, 5 µg/ml of Erbitux and 5 µg/ml of ME19, respectively, and incubated for 24 hours. A medium treated with no antibody was used as a negative control. After incubation, the cells were lysed with Complete Lysis-M (#04719956001, Roche), and the cell lysates were collected. the expression level of c-Met was measured by Total cMet detection ELISA kit (DYC358E, R&D systems), and the expression level of EGFR was measured by Total EGF Receptor ELISA kit (#7297, Cell Signaling), according to the manufacturer's manual.

Figure 12:
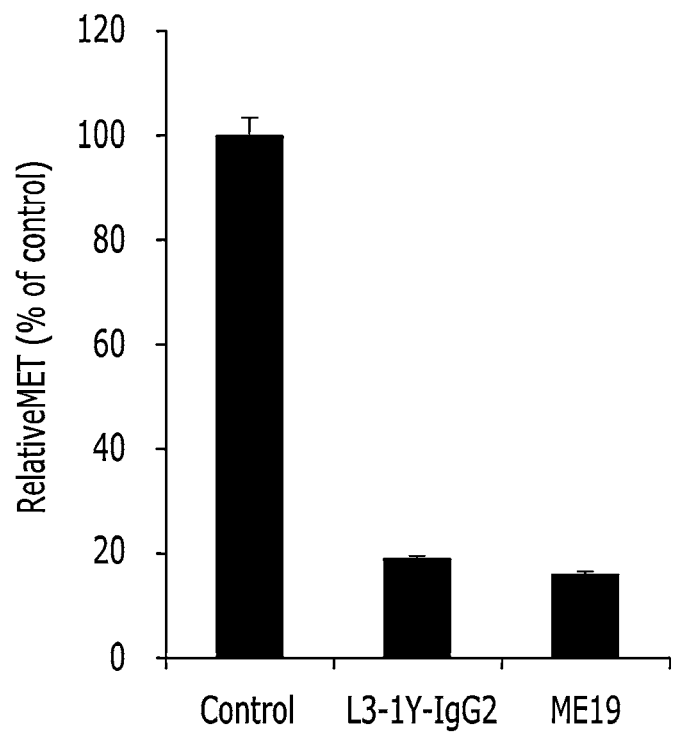
FIG. 12 is a graph displaying the expression amount of c-Met (upper) and EGFR (lower) by an anti-c-Met/anti-EGFR bispecific chimeric protein according to an embodiment.
Figure 12:
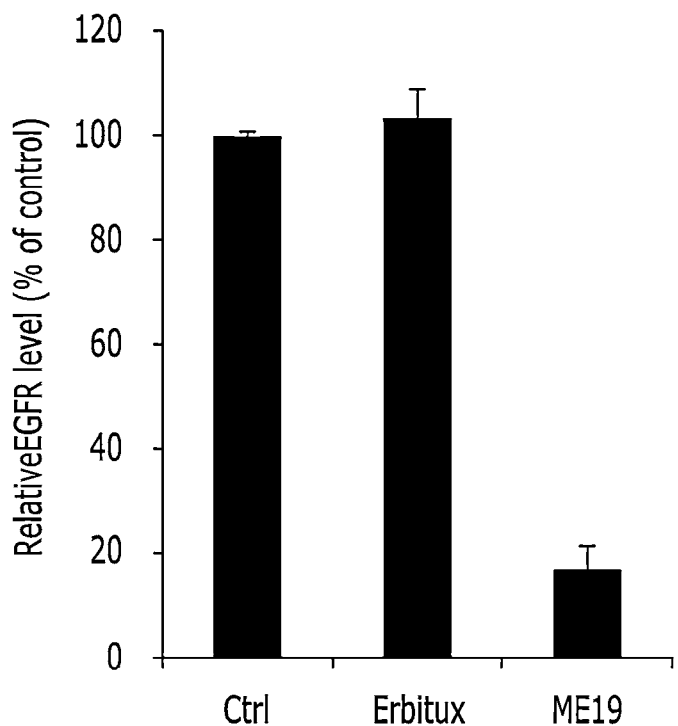

The obtained results are shown in FIG. 12. L3-1Y-IgG2 and ME19 all decrease the expression level of c-Met compared to the negative control (see upper of FIG. 12). Erbitux has no effect on the expression of EGFR, whereas ME19 considerably decreases the expression level of EGFR (see lower of FIG. 12) as well as the expression level of c-Met (see upper of FIG. 12).

Example 8

Preparation of an Anti-HER2/Anti-EGFR DARPin Bispecific Chimeric Protein

Figure 13:
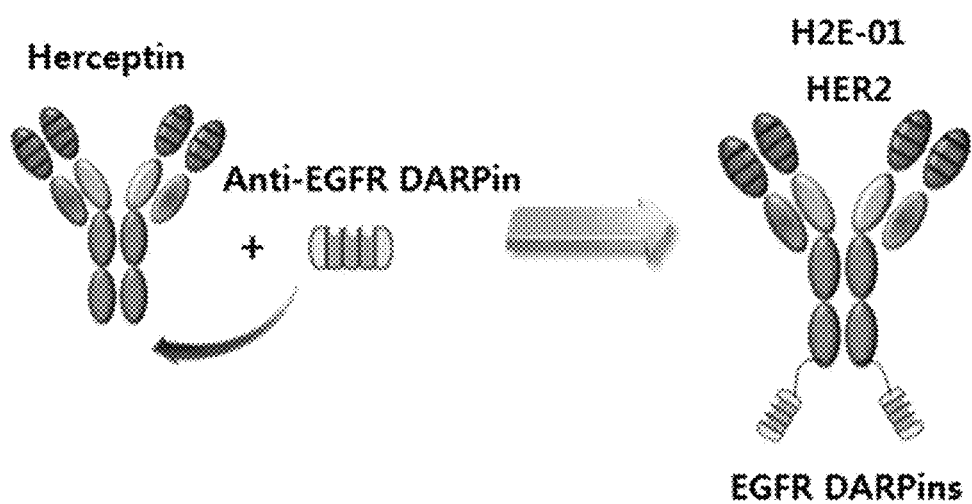
FIG. 13 is a schematic depicting a process of preparing an anti-HER2/anti-EGFR bispecific chimeric protein according to an embodiment.

The anti-EGFR DARPins (SEQ ID NO: 109) was fused to the C-terminus of Herceptin (Roche), to prepare an anti-HER2 antibody/anti-EGFR DARPin fusion complex (i.e., anti-HER2/anti-EGFR bispecific chimeric protein) (FIG. 13). The heavy chain of Herceptin antibody and the anti-EGFR DARPin were linked to each other through a peptide linker having 10 amino acids (GGGGSGGGGS; $(G_4S)_2$ (SEQ ID NO: 152)), to give 'Herceptin heavy chain—$(G_4S)_2$—anti-EGFR DARPins' form.

The prepared anti-HER2/anti-EGFR bispecific chimeric protein was named as "H2E-01".

Example 9

Examination of Properties and EGFR Affinity of the Anti-HER2/Anti-EGFR DARPin Bispecific Chimeric Protein To examine properties of the bispecific chimeric protein H2E-01 (anti-HER2/anti-EGFR DARPin bispecific chimeric protein) prepared in Example 8, 20 ug of the bispecific chimeric protein was injected to a HPLC system (WATERS 2695) equipped with TSKG3000SWXL column (Tosho) to the velocity of 0.5 ml/min, to conduct a Size Exclusion Chromatography.

Figure 14:
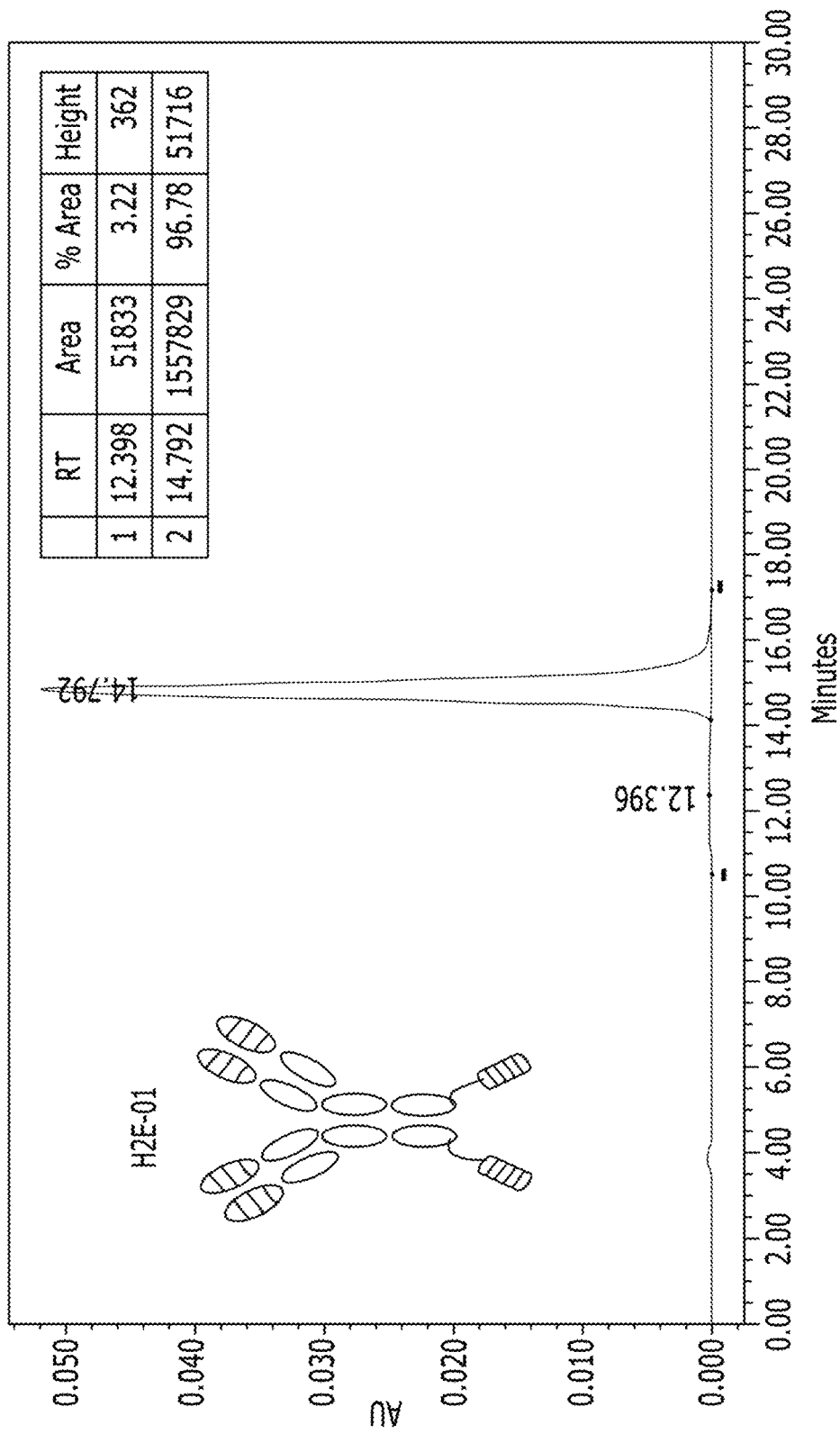
FIG. 14 is a graph displaying the stability properties of an anti-HER2/anti-EGFR bispecific chimeric protein according to an embodiment.

The obtained results are shown in FIG. 14. In FIG. 14, "1" refers to a quantitative value of the peak for a soluble dimer, and "2" refers to a quantitative value of the peak for a monomer. As shown in FIG. 14, similarly to ME-19 prepared in Example 1, anti-HER2/anti-EGFR DARPin bispecific chimeric protein H2E-01 forms very slight amount of soluble dimer (<1), which demonstrates that the bispecific chimeric protein is a very stable molecule.

The binding affinity of bispecific chimeric protein H2E-01 to each of the two antigens HER2 and EGFR was examined using Biacore T100 (GE). Human Fab binder (GE Healthcare) was immobilized on the surface of CM5 chip (#BR-1005-30, GE) according to the manufacturer's manual. About 90~120 RU of the bispecific chimeric protein H2E-01 was captured, and various concentrations of EGFR-Fc (#344-ER, R&D Systems) were added to the captured bispecific chimeric protein. 10 mM Glycine-HCl (pH 1.5) solution was added hereto, to regenerate the surface. To determine the affinity, the obtained data were fitted using BIA evaluation software (GE Healthcare, Biacore T100 evaluation software).

The obtained results are shown in Table 4.

TABLE 4

| Sample | Antigen | Flow Cell | $R_{max}$ (RU) | $K_D$ (nM) | $K_a$ (1/Ms) | $K_d$ (1/s) | Chi$^2$ | U-value | T($K_a$) | T ($K_d$) |
|---|---|---|---|---|---|---|---|---|---|---|
| H2E-01 | EGFR-Fc | #4, #1 | 78.89 | 0.03 | $1.0 \times 10^5$ | $<2.8 \times 10^{-5}$ | 1.58 | 95 | $6.2 \times 10^2$ | 1.2 |
|  | Her2-Fc | #2, #1 | 80.45 | <0.01 | $6.9 \times 10^5$ | $<7.5 \times 10^{-5}$ | 1.56 | 95 | $9.8 \times 10^2$ | 1.4 |

As shown in Table 4, the bispecific chimeric protein H2E-01 prepared in Example 8 exhibits very high affinity to EGFR and HER2 as KD=0.03 nM and <0.01 nM, respectively, as measured by Biacore.

Example 10

Examination of Cell Proliferation Inhibition of the Anti-HER2/Anti-EGFR Bispecific Chimeric Protein In order to examine the cancer cell proliferation inhibition effect of the bispecific chimeric protein H2E-01 prepared in Example 8, the degree of cell proliferation was tested in MKN45 cell line (KCLB No. 80103).

The MKN45 cells were cultured in RPMI1640 medium (#11875-093, Gibco) supplemented with 10% (v/v) FBS and 1% (v/v) Penicillin-Streptomycin under the conditions of 5% $CO_2$ and 37° C. To conduct cell proliferation assay, the cells were sub-cultured in 96-well plate at the concentration of $1 \times 10^4$ cell/well, treated with the anti-HER2/anti-EGFR DARPin bispecific chimeric protein H2E-01 prepared in Example 8 at the amount of 5 μg/ml, and further cultured for 72 hours. A group treated with no antibody was used as a negative control. Groups treated with one of commercially obtained EGFR inhibitor, Erbitux (#ET509081213, Merck; 5 μg/ml), HER2 inhibitor Herceptin (Trastuzumab, Roche; 5 μg/ml), or a combination thereof were used as positive controls.

After culturing, the cell proliferation was measured by Cell Counting Kit-8 assay (Dojindo Molecular Technologies, Gaithersburg, Md.) according to the manufacturer's manual. In brief, after culturing for 72 hours, 10 μl of CCK8 solution was added to each well, and further cultured 2.5 hours. Then, the absorbance at 450 nm was measured using microplate reader.

Figure 15:
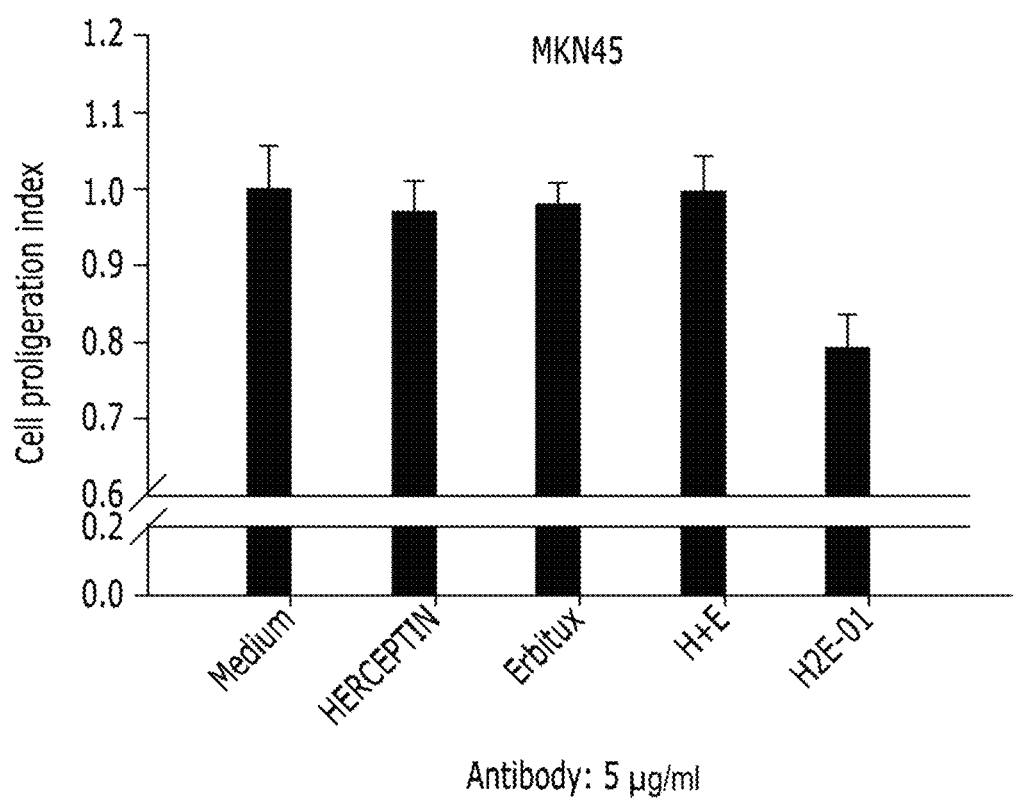
FIG. 15 is a graph displaying the degree of proliferation inhibition of MKN45 cells by an anti-HER2/anti-EGFR bispecific chimeric protein according to an embodiment.

The obtained results are shown in FIG. 15. As shown in FIG. 15, the anti-HER2/anti-EGFR DARPin bispecific chimeric protein H2E-01 exhibits excellent anticancer effect on gastric cancer cells such as MKN45, compared to Herceptin, Erbitux, and the combination thereof.

Example 11

Internalization of HER2 and EGFR by the Anti-HER2/Anti-EGFR Bispecific Chimeric Protein Gastric cancer cell line MKN45 (KCLB No. 80103) was provided at the amount of $4 \times 10^4$ cell/well. To the cells, Trastuzumab (Herceptin, Roche), Cetuximab (Erbitux, #ET509081213, Merck), and H2E-01 prepared in Example 8 were treated alone or in combination at the amount of 1 μg/ml per each well (when treated in combination, each treated amount is 1 μg/ml), and incubated at 37° C. for 2 hours. The incubated cells were treated with 4% (v/v) formaldehyde for 15 minutes, to be immobilized on plate, and then, washed three times with PBS. Thereafter, the resulted cells were treated with blocking buffer (0.5% (v/v) triton x-100 and 5% (v/v) donkey serum) for 1 hour at room temperature, and then, treated with primary antibodies respectively against HER2 and EGFR (primary antibody for HER2; #280003Z, Invitrogen, primary antibody for EGFR; #5616, Cell signaling) at the amount of 100 μl (1:100 diluted) at 4° C. for 15 hours. The resultant was washed three times with PBS, treated with secondary antibody (#A21433, Invitrogen) at the amount of 100 μl (1:2000 diluted) at room temperature for 1 hour, and washed again three times with PBS, to prepare a plate with mounting medium (#H-1200, Vector). The cells in the prepared plate were observed by a confocal microscope (Zeiss, LSM710).

Figure 16:
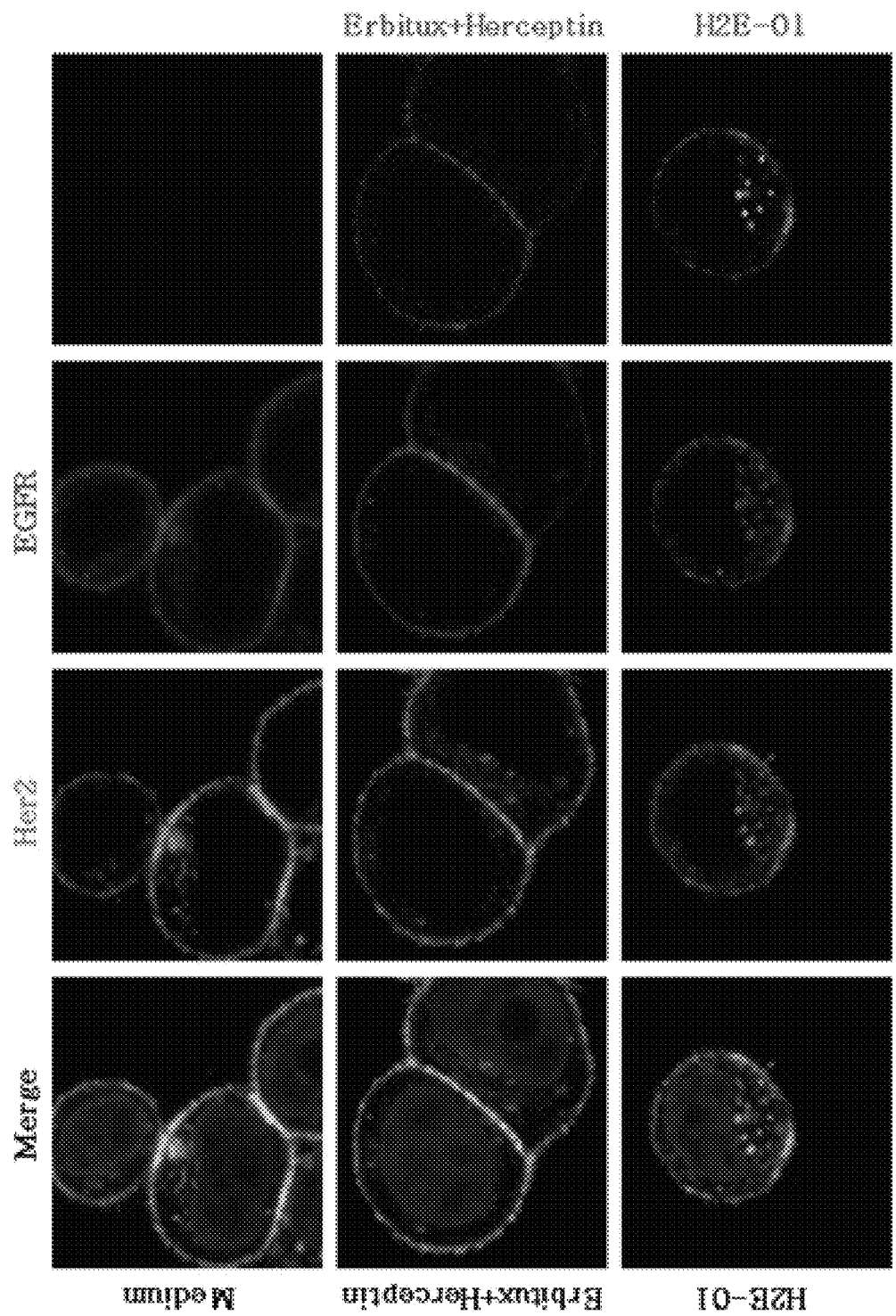
FIG. 16 is a fluorescent image depicting the internalization of HER2 and EGFR by an anti-HER2/anti-EGFR bispecific chimeric protein according to an embodiment.

The obtained results are shown in FIG. 16. As shown in FIG. 16, when Herceptin and Erbitux are treated in combination, EGFR and HER2 still remain on cell membrane, whereas when H2E-01 is treated, both of HER2 and EGFR move into a cell.

In conclusion, the anti-HER2/anti-EGFR DARPin bispecific chimeric protein with an anti-EGFR DARPin inhibits EGFR and HER2 functions by different mechanism from that of pre-existing anti-EGFR or anti-HER2 antibody.

Example 12

Preparation of an Anti-EGFR/HER3 Antibody/Anti-EGFR DARPin Fusion Complex

Figure 17:
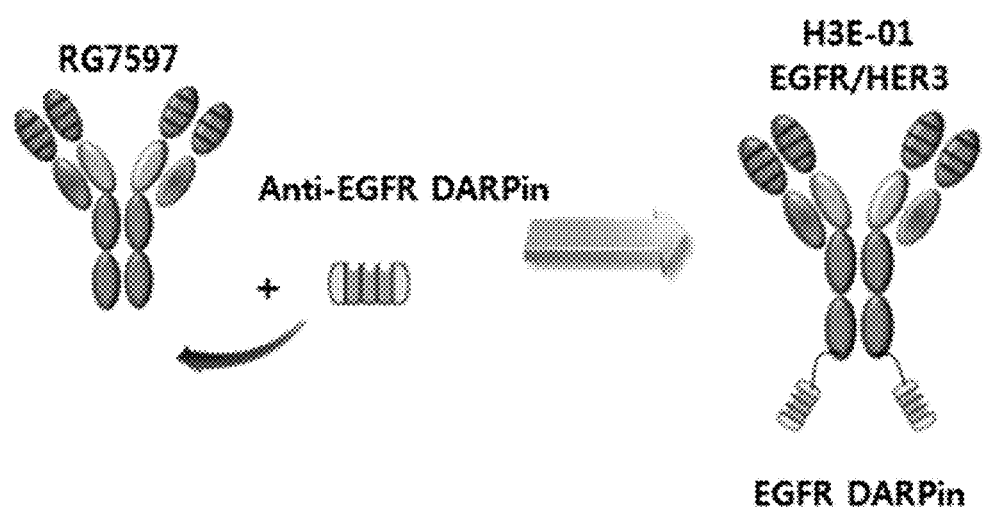
FIG. 17 is a schematic depicting a process of preparing an anti-HER3/anti-EGFR bispecific chimeric protein according to an embodiment.

The anti-EGFR DARPins (SEQ ID NO: 109) was fused to the C-terminus of anti-HER3 antibody RG-7597, to prepare an anti-HER3antibody/anti-EGFR DARPin fusion complex (i.e., anti-HER3/anti-EGFR bispecific chimeric protein) (FIG. 17). The heavy chain of RG-7597 antibody and the anti-EGFR DARPin were linked to each other through a peptide linker having 10 amino acids (GGGGSGGGGS; $(G_4S)_2$ (SEQ ID NO. 152)), to give 'RG-7597 heavy chain—$(G_4S)_2$—anti-EGFR DARPins' form. The anti-HER3 antibody RG-7597 was prepared using a heavy chain variable region of SEQ ID NO: 117, a light chain variable region of SEQ ID NO: 118, and IgG1 Fc region.

<Amino Acid Sequence of a Heavy Chain Variable Region of the Anti-EGFR/HER3 Antibody RG-7597>

(SEQ ID NO: 117)
EVQLVESGGGLVQPGGSLRLSCAASGFTLSGDWIHWVRQAPGKGLEWVGEI

SAAGGYTDYADSVKGRFTISADTSKNTAYLQMNSLRAEDTAVYYCARESRV

SFEAAMDYWGQGTLVTVSS

<Amino Acid Sequence of a Light Chain Variable Region of the Anti-EGFR/HER3 Antibody RG-7597>

(SEQ ID NO: 118)
DIQMTQSPSSLSASVGDRVTITCRASQNIATDVAWYQQKPGKAPKLLIYSA

SFLYSGVPSRFSGSGSGTDFTLTISSLQPEDFATYYCQQSEPEPYTFGQGT

KVEIK

The prepared anti-EGFR/HER3 antibody/anti-EGFR DARPin fusion complex was named as "EH3E-01".

To examine properties of the bispecific chimeric protein EH3E-01 (anti-HER3/anti-EGFR DARPin bispecific chimeric protein) prepared as above, 20 ug of the bispecific chimeric protein was injected to a HPLC system (WATERS 2695) equipped with TSKG3000SWXL column (Tosho) to the velocity of 0.5 ml/min, to conduct a Size Exclusion Chromatography.

Figure 18:
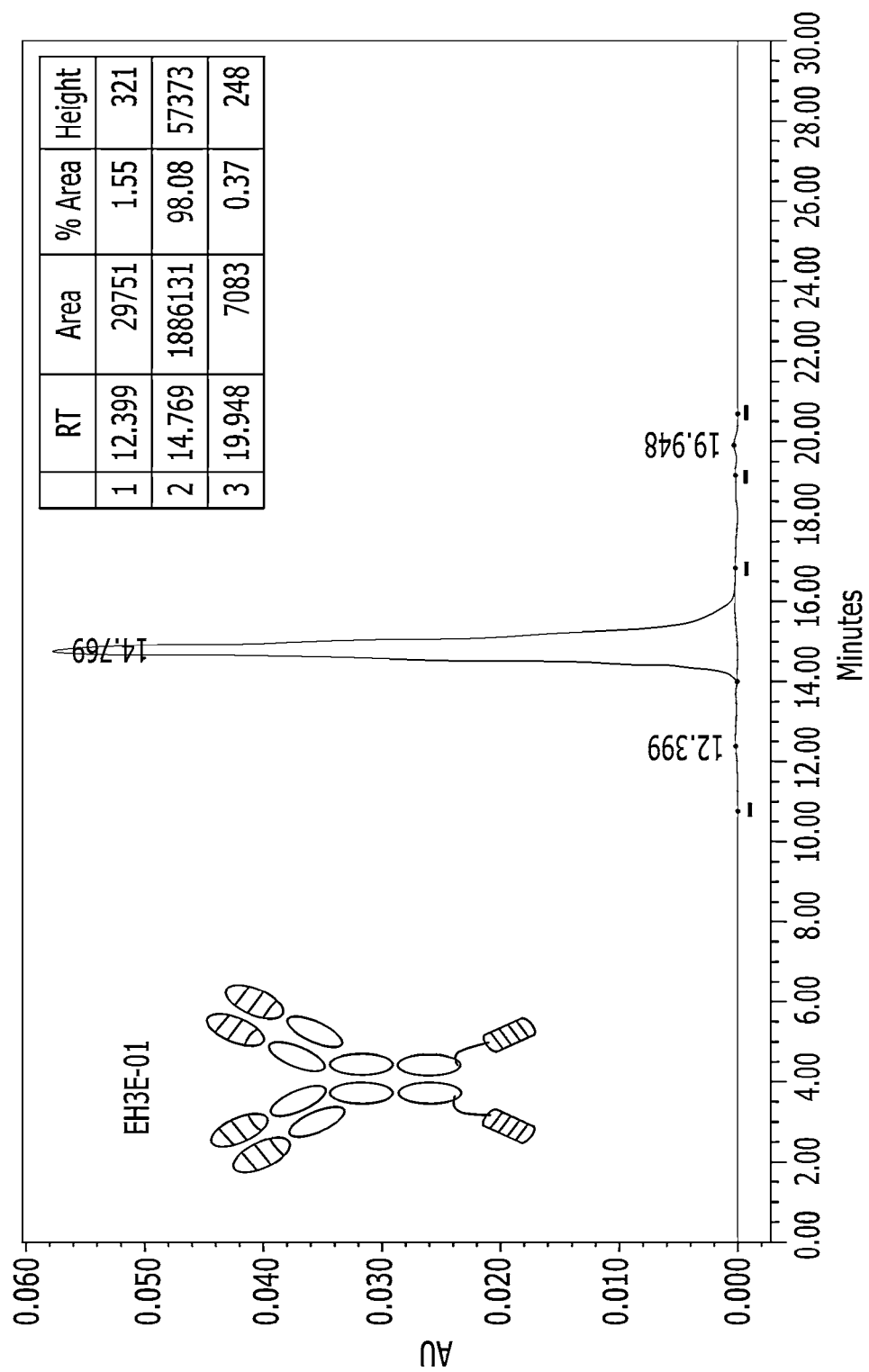
FIG. 18 is a graph displaying the stability properties of an anti-HER3/anti-EGFR bispecific chimeric protein according to an embodiment.

The obtained results are shown in FIG. 18. In FIG. 18, "1" refers to a quantitative value of the peak for a soluble dimer, and "2" refers to a quantitative value of the peak for a monomer. As shown in FIG. 18, similarly to ME-19 prepared in Example 1, anti-HER3/anti-EGFR DARPin bispecific chimeric protein EH3E-01 forms very slight amount of soluble dimer (<1), which demonstrates that the bispecific chimeric protein is a very stable molecule.

Example 13

Preparation of an Anti-c-Met/Anti-EGFR DARPins Bispecific Chimeric Protein 2

Figure 19:
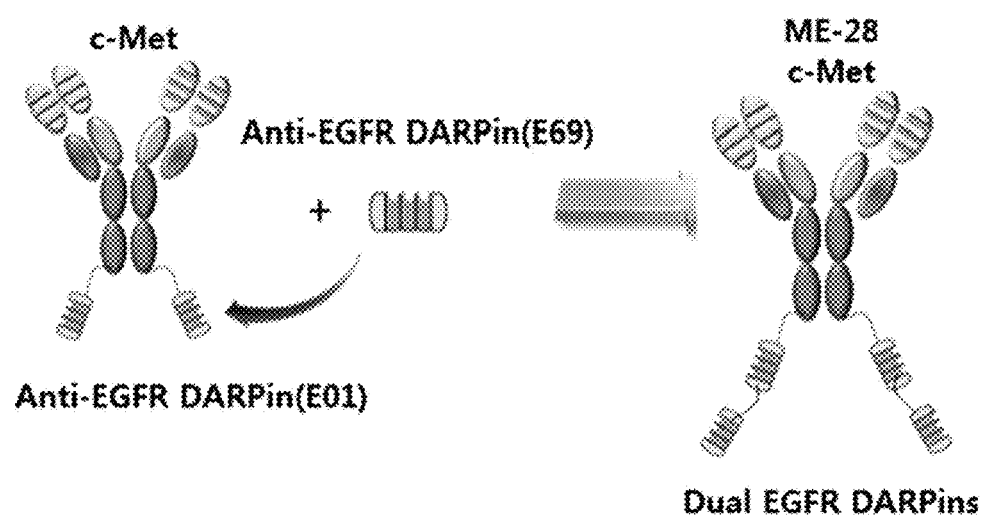
FIG. 19 is a schematic depicting a process of preparing an anti-c-Met/anti-EGFR (E01+E69) DARPins bispecific chimeric protein according to an embodiment.

Two anti-EGFR DARPins (DARPin-01 (SEQ ID NOs: 109) and DARPin-69 (SEQ ID NO: 112)) were fused to the C-terminus of the L3-1Y-IgG2 prepared in Reference Example 1, to prepare anti-c-Met antibody/anti-EGFR DARPin fusion complexes (i.e., anti-c-Met/anti-EGFR bispecific chimeric proteins), where two anti-EGFR DARPins are tandemly inked to each C-terminus of the dimeric anti-c-Met antibody in the IgG form (FIG. 19). The heavy chain of L3-1Y-IgG2 antibody and the anti-EGFR DARPin-01 were linked to each other through a peptide linker having 10 amino acids (GGGGSGGGGS; $(G4S)_2$ (SEQ ID NO. 152)), and anti-EGFR DARPin -01 and anti-EGFR DARPin-69 were also linked to each other through a peptide linker having 10 amino acids (GGGGSGGGGS; $(G4S)_2$ (SEQ ID NO. 152)), to give 'L3-1Y -IgG2 heavy chain—$(G4S)_2$—anti-EGFR DARPin-01—$(G4S)_2$—anti-EGFR DARPin -69' form.

The prepared anti-c-Met/anti-EGFR bispecific chimeric protein was named as "ME-28".

To examine properties of the prepared anti-c-Met/anti-EGFR bispecific chimeric protein ME-28, 20 ug of the bispecific chimeric protein was injected to a HPLC system (WATERS 2695) equipped with TSKG3000SWXL column (Tosho) to the velocity of 0.5 ml/min, to conduct a Size Exclusion Chromatography.

Figure 20:
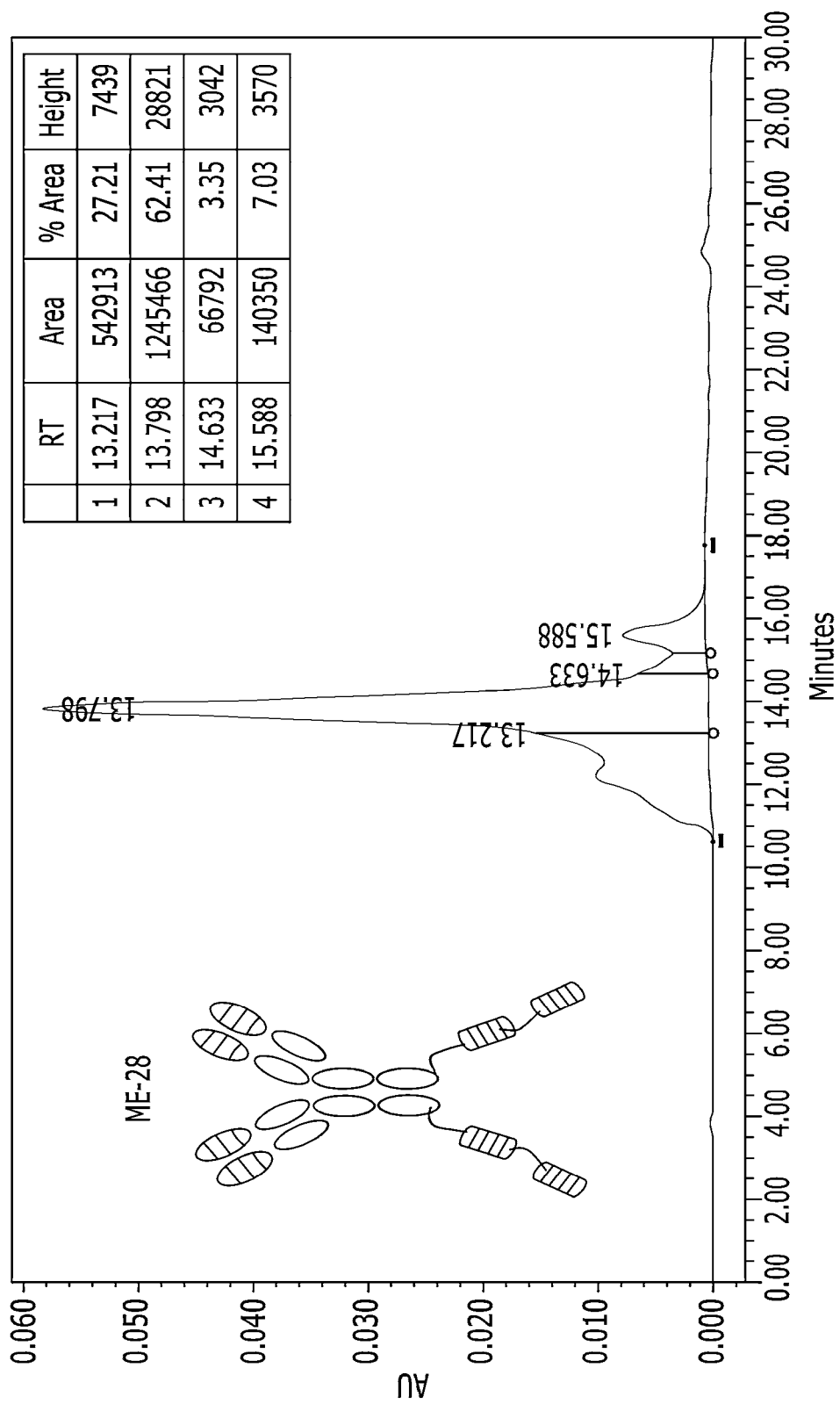
FIG. 20 is a graph displaying the stability properties of an anti-c-Met/anti-EGFR (E01+E69) DARPins bispecific chimeric protein according to an embodiment.

The obtained results are shown in FIG. 20. In FIG. 20, "1" refers to a quantitative value of the peak for a soluble dimer, and "2" refers to a quantitative value of the peak for a monomer ("3" and "4" is presumed to refer to each degraded bispecific chimeric protein fragment. As shown in FIG. 20, the bispecific chimeric protein ME-28 forms relatively increased amount of soluble dimer or polymer (>5), compared to ME-19.

The binding affinity of bispecific chimeric protein ME-28 to EGFR was examined using Biacore T100 (GE). Human Fab binder (GE Healthcare) was immobilized on the surface of CM5 chip (#BR-1005-30, GE) according to the manufacturer's manual. About 90~120 RU of the bispecific chimeric protein ME-28 was captured, and various concentrations of EGFR-Fc (#344-ER, R&D Systems) were added to the captured bispecific chimeric protein. 10 mM Glycine-HCl (pH 1.5) solution was added hereto, to regenerate the surface. To determine the affinity, the obtained data were fitted using BIA evaluation software (GE Healthcare, Biacore T100 evaluation software).

The obtained results are shown in Table 5.

TABLE 5

| Sample | Antigen | $K_D$ (nM) | $k_a$ (1/Ms) | $k_d$ (1/s) |
|---|---|---|---|---|
| ME28 | EGFR | <0.01 | $1.1 \times 10^5$ | $<3.4 \times 10^{-5}$ |

As shown in Table 5, the bispecific chimeric protein ME-28 exhibits very high affinity to EGFR as KD<0.01 nM as measured by Biacore.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having,"

"including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A bispecific chimeric protein comprising:
   (a) anti-epidermal growth factor receptor (EGFR) DARPins, and
   (b) an anti-c-Met IgG antibody or a dimeric anti-c-Met scFv-Fc antibody fragment; wherein the C-terminus of each Fc region of the anti-c-Met IgG antibody or the dimeric anti-c-Met scFv-Fc antibody fragment is linked to one or more anti-EGFR DARPins.

2. The bispecific chimeric protein according to claim 1, wherein each of the one or more anti-EGFR DARPins linked to the C-terminus of each Fc region comprises one or more of SEQ ID NO: 109, SEQ ID NO: 110, SEQ ID NO: 111, or SEQ ID NO: 112, any of which are, optionally, repeated 2 to 10 times.

3. The bispecific chimeric protein according to claim 1, wherein the anti-c-Met IgC antibody or the dimeric anti-c-Met scFv-Fc antibody fragment comprises:
   (a) a CDR-H1 comprising the amino acid sequence of SEQ ID NO: 4;
   (b) a CDR-H2 comprising the amino acid sequence of SEQ ID NO: 5 or SEQ ID NO: 2;
   (c) a CDR-H3 comprising the amino acid sequence of SEQ ID NO: 6, SEQ ID NO: 85, or an amino acid sequence having 6-13 consecutive amino acids within SEQ ID NO: 85 including the amino acid residues from the $1^{st}$ to $6^{th}$ positions of SEQ ID NO: 85;
   (d) a CDR-L1 comprising the amino acid sequence of SEQ ID NO: 7;
   (e) a CDR-L2 comprising the amino acid sequence of SEQ ID NO: 8, and
   (f) a CDR-L3 comprising the amino acid sequence of SEQ ID NO: 9, SEQ ID NO: 15, SEQ ID NO: 86, or an amino acid sequence comprising 9-17 consecutive amino acids within SEQ ID NO: 89 including the amino acid residues from the $1^{st}$ to $9^{th}$ positions of SEQ ID NO: 89.

4. The bispecific chimeric protein according to claim 1, wherein the anti-c-Met IgC antibody or the dimeric anti-c-Met scFv-Fc antibody fragment comprises
   a CDR-H1 comprising the amino acid sequence of SEQ ID NO: 1, SEQ ID NO: 22, SEQ ID NO: 23, or SEQ ID NO: 24,
   a CDR-H2 comprising the amino acid sequence of SEQ ID NO: 2, SEQ ID NO: 25, or SEQ ID NO: 26,
   a CDR-H3 comprising the amino acid sequence of SEQ ID NO: 3, SEQ ID NO: 27, SEQ ID NO: 28, or SEQ ID NO: 85; and
   a CDR-L1 comprising the amino acid sequence of SEQ ID NO: 10, SEQ ID NO: 29, SEQ ID NO: 30, SEQ ID NO: 31, SEQ ID NO: 32, SEQ ID NO: 33, or SEQ ID NO: 106,
   a CDR-L2 comprising the amino acid sequence of SEQ ID NO: 11, SEQ ID NO: 34, SEQ ID NO: 35, or SEQ ID NO: 36, and
   a CDR-L3 comprising the amino acid sequence of SEQ ID NO: 12, SEQ ID NO: 13, SEQ ID NO: 14, SEQ ID NO: 15, SEQ ID NO: 16, SEQ ID NO: 37, SEQ ID NO: 86, or SEQ ID NO: 89.

5. The bispecific chimeric protein according to claim 1, wherein the anti-c-Met IgC antibody or the dimeric anti-c-Met scFv-Fc antibody fragment comprises:
   a heavy chain variable region comprising an amino acid sequence selected from the group consisting of SEQ ID NOs: 17, 74, 87, 90, 91, 92, 93, and 94, a light chain variable region comprising an amino acid sequence selected from the group consisting of SEQ ID NOs: 119, 18, 19, 20, 21, 75, 88, 95, 96, 97, 98, 99, and 107, or a combination of the heavy chain variable region and the light chain variable region.

6. The bispecific chimeric protein according to claim 1, wherein the anti-c-Met IgC antibody or the dimeric anti-c-Met scFv-Fc antibody fragment comprises:

a heavy chain comprising the amino acid sequence of SEQ ID NO: 62, the amino acid sequence from the $18^{th}$ to $462^{nd}$ positions of SEQ ID NO: 62, the amino acid sequence of SEQ ID NO: 64, the amino acid sequence from the $18^{th}$ to $461^{st}$ positions of SEQ ID NO: 64, the amino acid sequence of SEQ ID NO: 66, or the amino acid sequence from the $18^{th}$ to $460^{th}$ positions of SEQ ID NO: 66; and a light chain comprising the amino acid sequence of SEQ ID NO: 68, the amino acid sequence from the $21^{st}$ to $240^{th}$ positions of SEQ ID NO: 68, the amino acid sequence of SEQ ID NO: 70, the amino acid sequence from the $21^{st}$ to $240^{th}$ positions of SEQ ID NO: 70, or the amino acid sequence of SEQ ID NO: 108.

7. The bispecific chimeric protein of claim 1, further comprising a peptide linker linking the one or more anti-EGFR DARPins to the C-terminus of each Fc region of the anti-c-Met IgG antibody or the dimeric anti-c-Met scFv-Fc antibody fragment.

8. The bispecific chimeric protein of claim 1, wherein the C-terminus of each Fc region of the anti-c-Met IgG antibody or the dimeric anti-c-Met scFv-Fc antibody fragment is linked to two or more anti-EGFR DARPins.

9. The bispecific chimeric protein according to claim 8, wherein each of the two or more anti-EGFR DARPins linked to the C-terminus of each Fc region comprises one or more of SEQ ID NO: 109, SEQ ID NO: 110, SEQ ID NO: 111, or SEQ ID NO: 112, any of which are, optionally, repeated 2 to 10 times.

10. A method of preparing the bispecific chimeric protein of claim 1 comprising linking one or more anti-EGFR DARPins to the C-terminus of each Fc region of an anti-c-Met IgG antibody or a dimeric anti-c-Met scFv-Fc antibody fragment to provide the bispecific chimeric protein.

11. The method of claim 10, wherein each of the one or more anti-EGFR DARPins linked to the C-terminus of each Fc region comprises one or more of SEQ ID NO: 109, SEQ ID NO: 110, SEQ ID NO: 111, or SEQ ID NO: 112, any of which are, optionally, repeated 2 to 10 times.

12. The method of claim 10, wherein the anti-c-Met antibody or antibody fragment comprises:

(a) a CDR-H1 comprising the amino acid sequence of SEQ ID NO: 4;

(b) a CDR-H2 comprising the amino acid sequence of SEQ ID NO: 5, SEQ ID NO: 2, or an amino acid sequence having 8-19 consecutive amino acids within SEQ ID NO: 2 including the amino acid residues from the $3^{rd}$ to $10^{th}$ positions of SEQ ID NO: 2;

(c) a CDR-H3 comprising the amino acid sequence of SEQ ID NO: 6, SEQ ID NO: 85, or an amino acid sequence having 6-13 consecutive amino acids within SEQ ID NO: 85 including the amino acid residues from the $1^{st}$ to $6^{th}$ positions of SEQ ID NO: 85;

(d) a CDR-L1 comprising the amino acid sequence of SEQ ID NO: 7, (e) a CDR-L2 comprising the amino acid sequence of SEQ ID NO: 8, and (f) a CDR-L3 comprising the amino acid sequence of SEQ ID NO: 9, SEQ ID NO: 15, SEQ ID NO: 86, or an amino acid sequence having 9-17 consecutive amino acids within SEQ ID NO: 89 including the amino acid residues from the $1^{st}$ to $9^{th}$ positions of SEQ ID NO: 89.

13. The method of claim 10, wherein the anti-cancer efficacy of the bispecific chimeric protein is enhanced compared to the anti-c-Met IgG antibody or the dimeric anti-c-Met scFv-Fc antibody fragment without the DARPins linked thereto.

14. A pharmaceutical composition comprising the bispecific chimeric protein of claim 1.

15. A nucleic acid encoding the bispecific chimeric protein of claim 1, optionally in a vector.

16. A cultured cell comprising the nucleic acid of claim 15.

17. A method of preparing the bispecific chimeric protein of claim 1 comprising expressing a nucleic acid encoding the bispecific chimeric protein in a cell, whereby the bispecific chimeric protein is provided.

18. A method of treating a cancer comprising administering the bispecific chimeric protein of claim 1 to a subject in need of the treatment of a cancer.

* * * * *

```
                        SEQUENCE LISTING

<160> NUMBER OF SEQ ID NOS: 152

<210> SEQ ID NO 1
<211> LENGTH: 5
<212> TYPE: PRT
<213> ORGANISM: Artificial Sequence
<220> FEATURE:
<223> OTHER INFORMATION: Synthetic (heavy chain CDR1 of AbF46)

<400> SEQUENCE: 1

Asp Tyr Tyr Met Ser
1               5

<210> SEQ ID NO 2
<211> LENGTH: 19
<212> TYPE: PRT
<213> ORGANISM: Artificial Sequence
<220> FEATURE:
<223> OTHER INFORMATION: Synthetic (heavy chain CDR2 of AbF46)

<400> SEQUENCE: 2

Phe Ile Arg Asn Lys Ala Asn Gly Tyr Thr Thr Glu Tyr Ser Ala Ser
1               5                   10                  15

Val Lys Gly

<210> SEQ ID NO 3
<211> LENGTH: 6
<212> TYPE: PRT
<213> ORGANISM: Artificial Sequence
<220> FEATURE:
<223> OTHER INFORMATION: Synthetic (heavy chain CDR3 of AbF46)

<400> SEQUENCE: 3

Asp Asn Trp Phe Ala Tyr
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic (heavy chain CDR1 of c-Met antibody)
<220> FEATURE:
<221> NAME/KEY: MOD_RES
<222> LOCATION: (1)..(1)
<223> OTHER INFORMATION: Xaa is Pro or Ser or absent
<220> FEATURE:
<221> NAME/KEY: MOD_RES
<222> LOCATION: (2)..(2)
<223> OTHER INFORMATION: Xaa is Glu or Asp
```

```
<400> SEQUENCE: 4

Xaa Xaa Tyr Tyr Met Ser
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic (heavy chain CDR2 of c-Met antibody)
<220> FEATURE:
<221> NAME/KEY: MOD_RES
<222> LOCATION: (3)..(3)
<223> OTHER INFORMATION: Xaa is Asn or Lys
<220> FEATURE:
<221> NAME/KEY: MOD_RES
<222> LOCATION: (4)..(4)
<223> OTHER INFORMATION: Xaa is Ala or Val
<220> FEATURE:
<221> NAME/KEY: MOD_RES
<222> LOCATION: (7)..(7)
<223> OTHER INFORMATION: Xaa is Asn or Thr

<400> SEQUENCE: 5

Arg Asn Xaa Xaa Asn Gly Xaa Thr
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic (heavy chain CDR3 of c-Met antibody)
<220> FEATURE:
<221> NAME/KEY: MOD_RES
<222> LOCATION: (5)..(5)
<223> OTHER INFORMATION: Xaa is Ser or Thr

<400> SEQUENCE: 6

Asp Asn Trp Leu Xaa Tyr
1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic (light chain CDR1 of c-Met antibody)
<220> FEATURE:
<221> NAME/KEY: MOD_RES
<222> LOCATION: (4)..(4)
<223> OTHER INFORMATION: Xaa is His, Arg, Gln or Lys
<220> FEATURE:
<221> NAME/KEY: MOD_RES
<222> LOCATION: (9)..(9)
<223> OTHER INFORMATION: Xaa is Ser or Trp
<220> FEATURE:
<221> NAME/KEY: MOD_RES
<222> LOCATION: (12)..(12)
<223> OTHER INFORMATION: Xaa is His or Gln
<220> FEATURE:
<221> NAME/KEY: MOD_RES
<222> LOCATION: (13)..(13)
<223> OTHER INFORMATION: Xaa is Lys or Asn

<400> SEQUENCE: 7

Lys Ser Ser Xaa Ser Leu Leu Ala Xaa Gly Asn Xaa Xaa Asn Tyr Leu
1               5                   10                  15

Ala
```

```
<210> SEQ ID NO 8
<211> LENGTH: 7
<212> TYPE: PRT
<213> ORGANISM: Artificial Sequence
<220> FEATURE:
<223> OTHER INFORMATION: Synthetic (light chain CDR2 of c-Met antibody)
<220> FEATURE:
<221> NAME/KEY: MOD_RES
<222> LOCATION: (2)..(2)
<223> OTHER INFORMATION: Xaa is Ala or Gly
<220> FEATURE:
<221> NAME/KEY: MOD_RES
<222> LOCATION: (4)..(4)
<223> OTHER INFORMATION: Xaa is Thr or Lys
<220> FEATURE:
<221> NAME/KEY: MOD_RES
<222> LOCATION: (7)..(7)
<223> OTHER INFORMATION: Xaa is Ser or Pro

<400> SEQUENCE: 8

Trp Xaa Ser Xaa Arg Val Xaa
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic (light chain CDR3 of c-Met antibody)
<220> FEATURE:
<221> NAME/KEY: MOD_RES
<222> LOCATION: (1)..(1)
<223> OTHER INFORMATION: Xaa is Gly, Ala or Gln
<220> FEATURE:
<221> NAME/KEY: MOD_RES
<222> LOCATION: (6)..(6)
<223> OTHER INFORMATION: Xaa is Arg, His, Ser, Ala, Gly or Lys
<220> FEATURE:
<221> NAME/KEY: MOD_RES
<222> LOCATION: (8)..(8)
<223> OTHER INFORMATION: Xaa is Leu, Tyr, Phe or Met

<400> SEQUENCE: 9

Xaa Gln Ser Tyr Ser Xaa Pro Xaa Thr
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic (light chain CDR1 of AbF46)

<400> SEQUENCE: 10

Lys Ser Ser Gln Ser Leu Leu Ala Ser Gly Asn Gln Asn Asn Tyr Leu
1               5                   10                  15

Ala

<210> SEQ ID NO 11
<211> LENGTH: 7
<212> TYPE: PRT
<213> ORGANISM: Artificial Sequence
<220> FEATURE:
<223> OTHER INFORMATION: Synthetic (light chain CDR2 of AbF46)

<400> SEQUENCE: 11

Trp Ala Ser Thr Arg Val Ser
1               5
```

<210> SEQ ID NO 12
<211> LENGTH: 9
<212> TYPE: PRT
<213> ORGANISM: Artificial Sequence
<220> FEATURE:
<223> OTHER INFORMATION: Synthetic (light chain CDR3 of AbF46)

<400> SEQUENCE: 12

Gln Gln Ser Tyr Ser Ala Pro Leu Thr
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic (CDR-L3 derived from L3-1 clone)

<400> SEQUENCE: 13

Gln Gln Ser Tyr Ser Arg Pro Tyr Thr
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic (CDR-L3 derived from L3-2 clone)

<400> SEQUENCE: 14

Gly Gln Ser Tyr Ser Arg Pro Leu Thr
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic (CDR-L3 derived from L3-3 clone)

<400> SEQUENCE: 15

Ala Gln Ser Tyr Ser His Pro Phe Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic (CDR-L3 derived from L3-5 clone)

<400> SEQUENCE: 16

Gln Gln Ser Tyr Ser Arg Pro Phe Thr
1               5

<210> SEQ ID NO 17
<211> LENGTH: 117
<212> TYPE: PRT
<213> ORGANISM: Artificial Sequence
<220> FEATURE:
<223> OTHER INFORMATION: Synthetic (heavy chain variable region of anti
      c-Met humanized antibody(huAbF46-H4))

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr

```
            20                  25                  30
Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 18
<211> LENGTH: 114
<212> TYPE: PRT
<213> ORGANISM: Artificial Sequence
<220> FEATURE:
<223> OTHER INFORMATION: Synthetic (light chain variable region of
      anti c-Met humanized antibody(huAbF46-H4))

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg

<210> SEQ ID NO 19
<211> LENGTH: 114
<212> TYPE: PRT
<213> ORGANISM: Artificial Sequence
<220> FEATURE:
<223> OTHER INFORMATION: Synthetic (light chain variable region of
      anti c-Met humanized antibody(huAbF46-H4))

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80
```

Ile Ser Ser Leu Gln Pro Glu Asp Phe Ala Thr Tyr Tyr Cys Gly Gln
            85                  90                  95

Ser Tyr Ser Arg Pro Leu Thr Phe Gly Gln Gly Thr Lys Val Glu Ile
        100                 105                 110

Lys Arg

<210> SEQ ID NO 20
<211> LENGTH: 114
<212> TYPE: PRT
<213> ORGANISM: Artificial Sequence
<220> FEATURE:
<223> OTHER INFORMATION: Synthetic (light chain variable region of
      anti c-Met humanized antibody(huAbF46-H4))

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Ala Gln
            85                  90                  95

Ser Tyr Ser His Pro Phe Ser Phe Gly Gln Gly Thr Lys Val Glu Ile
        100                 105                 110

Lys Arg

<210> SEQ ID NO 21
<211> LENGTH: 114
<212> TYPE: PRT
<213> ORGANISM: Artificial Sequence
<220> FEATURE:
<223> OTHER INFORMATION: Synthetic (light chain variable region of
      anti c-Met humanized antibody(huAbF46-H4))

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
            85                  90                  95

Ser Tyr Ser Arg Pro Phe Thr Phe Gly Gln Gly Thr Lys Val Glu Ile
        100                 105                 110

Lys Arg

<210> SEQ ID NO 22

```
<211> LENGTH: 6
<212> TYPE: PRT
<213> ORGANISM: Artificial Sequence
<220> FEATURE:
<223> OTHER INFORMATION: Synthetic (CDR-H1 derived from H11-4 clone)

<400> SEQUENCE: 22

Pro Glu Tyr Tyr Met Ser
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic (CDR-H1 derived from YC151 clone)

<400> SEQUENCE: 23

Pro Asp Tyr Tyr Met Ser
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic (CDR-H1 derived from YC193 clone)

<400> SEQUENCE: 24

Ser Asp Tyr Tyr Met Ser
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic (CDR-H2 derived from YC244 clone)

<400> SEQUENCE: 25

Arg Asn Asn Ala Asn Gly Asn Thr
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic (CDR-H2 derived from YC321 clone)

<400> SEQUENCE: 26

Arg Asn Lys Val Asn Gly Tyr Thr
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic (CDR-H3 derived from YC354 clone)

<400> SEQUENCE: 27

Asp Asn Trp Leu Ser Tyr
1               5

<210> SEQ ID NO 28
<211> LENGTH: 6
```

```
<212> TYPE: PRT
<213> ORGANISM: Artificial Sequence
<220> FEATURE:
<223> OTHER INFORMATION: Synthetic (CDR-H3 derived from YC374 clone)

<400> SEQUENCE: 28

Asp Asn Trp Leu Thr Tyr
1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic (CDR-L1 derived from L1-1 clone)

<400> SEQUENCE: 29

Lys Ser Ser His Ser Leu Leu Ala Ser Gly Asn Gln Asn Asn Tyr Leu
1               5                   10                  15

Ala

<210> SEQ ID NO 30
<211> LENGTH: 17
<212> TYPE: PRT
<213> ORGANISM: Artificial Sequence
<220> FEATURE:
<223> OTHER INFORMATION: Synthetic (CDR-L1 derived from L1-3 clone)

<400> SEQUENCE: 30

Lys Ser Ser Arg Ser Leu Leu Ser Ser Gly Asn His Lys Asn Tyr Leu
1               5                   10                  15

Ala

<210> SEQ ID NO 31
<211> LENGTH: 17
<212> TYPE: PRT
<213> ORGANISM: Artificial Sequence
<220> FEATURE:
<223> OTHER INFORMATION: Synthetic (CDR-L1 derived from L1-4 clone)

<400> SEQUENCE: 31

Lys Ser Ser Lys Ser Leu Leu Ala Ser Gly Asn Gln Asn Asn Tyr Leu
1               5                   10                  15

Ala

<210> SEQ ID NO 32
<211> LENGTH: 17
<212> TYPE: PRT
<213> ORGANISM: Artificial Sequence
<220> FEATURE:
<223> OTHER INFORMATION: Synthetic (CDR-L1 derived from L1-12 clone)

<400> SEQUENCE: 32

Lys Ser Ser Arg Ser Leu Leu Ala Ser Gly Asn Gln Asn Asn Tyr Leu
1               5                   10                  15

Ala

<210> SEQ ID NO 33
<211> LENGTH: 17
<212> TYPE: PRT
<213> ORGANISM: Artificial Sequence
<220> FEATURE:
<223> OTHER INFORMATION: Synthetic (CDR-L1 derived from L1-22 clone)

<400> SEQUENCE: 33
```

Lys Ser Ser His Ser Leu Leu Ala Ser Gly Asn Gln Asn Asn Tyr Leu
1               5                   10                  15

Ala

<210> SEQ ID NO 34
<211> LENGTH: 7
<212> TYPE: PRT
<213> ORGANISM: Artificial Sequence
<220> FEATURE:
<223> OTHER INFORMATION: Synthetic (CDR-L2 derived from L2-9 clone)

<400> SEQUENCE: 34

Trp Ala Ser Lys Arg Val Ser
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic (CDR-L2 derived from L2-12 clone)

<400> SEQUENCE: 35

Trp Gly Ser Thr Arg Val Ser
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic (CDR-L2 derived from L2-16 clone)

<400> SEQUENCE: 36

Trp Gly Ser Thr Arg Val Pro
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic (CDR-L3 derived from L3-32 clone)

<400> SEQUENCE: 37

Gln Gln Ser Tyr Ser Lys Pro Phe Thr
1               5

<210> SEQ ID NO 38
<211> LENGTH: 1416
<212> TYPE: DNA
<213> ORGANISM: Artificial Sequence
<220> FEATURE:
<223> OTHER INFORMATION: Synthetic (nucleotide sequence of heavy chain
      of chAbF46)
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:

<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 38

```
gaattcgccg ccaccatgga atggagctgg gtttttctcg taacactttt aaatggtatc      60
cagtgtgagg tgaagctggt ggagtctgga ggaggcttgg tacagcctgg gggttctctg     120
agactctcct gtgcaacttc tgggttcacc ttcactgatt actacatgag ctgggtccgc     180
cagcctccag gaaaggcact tgagtggttg gttttattag aaacaaagc taatggttac     240
acaacagagt acagtgcatc tgtgaagggt cggttcacca tctccagaga taattcccaa     300
agcatcctct atcttcaaat ggacaccctg agagctgagg acagtgccac ttattactgt     360
gcaagagata actggtttgc ttactggggc caagggactc tggtcactgt ctctgcagct     420
agcaccaagg gcccatcggt cttccccctg gcaccctcct ccaagagcac ctctgggggc     480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttcccccc aaaacccaag gacaccctca tgatctcccg gacccctgag     840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc cccatcccg ggaggagatg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga ctcgag                               1416
```

<210> SEQ ID NO 39
<211> LENGTH: 759
<212> TYPE: DNA
<213> ORGANISM: Artificial Sequence
<220> FEATURE:
<223> OTHER INFORMATION: Synthetic (nucleotide sequence of light chain of chAbF46)
<220> FEATURE:
<221> NAME/KEY: misc_difference
<222> LOCATION: (1)..(6)
<223> OTHER INFORMATION: EcoRI restriction site
<220> FEATURE:

<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 39

```
gaattcacta gtgattaatt cgccgccacc atggattcac aggcccaggt cctcatgttg    60
ctgctgctat cggtatctgg tacctgtgga gacattttga tgacccagtc tccatcctcc   120
ctgactgtgt cagcaggaga aaggtcact atgagctgca agtccagtca gagtctttta   180
gctagtggca accaaaataa ctacttggcc tggcaccagc agaaaccagg acgatctcct   240
aaaatgctga taatttgggc atccactagg gtatctggag tccctgatcg cttcataggc   300
agtggatctg ggacggattt cactctgacc atcaacagtg tgcaggctga agatctggct   360
gtttattact gtcagcagtc ctacagcgct ccgctcacgt tcggtgctgg gaccaagctg   420
gagctgaaac gtacggtggc tgcaccatct gtcttcatct tcccgccatc tgatgagcag   480
ttgaaatctg gaactgcctc tgttgtgtgc ctgctgaata acttctatcc cagagaggcc   540
aaagtacagt ggaaggtgga taacgcccte caatcgggta actcccagga gagtgtcaca   600
gagcaggaca gcaaggacag cacctacagc ctcagcagca ccctgacgct gagcaaagca   660
gactacgaga aacacaaagt ctacgcctgc gaagtcaccc atcagggcct gagctcgccc   720
gtcacaaaga gcttcaacag gggagagtgt tgactcgag                         759
```

<210> SEQ ID NO 40
<211> LENGTH: 447
<212> TYPE: PRT
<213> ORGANISM: Artificial Sequence
<220> FEATURE:
<223> OTHER INFORMATION: Synthetic (amino acid sequence of H1-heavy)

<400> SEQUENCE: 40

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95
```

```
Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 41
<211> LENGTH: 447
<212> TYPE: PRT
<213> ORGANISM: Artificial Sequence
<220> FEATURE:
<223> OTHER INFORMATION: Synthetic (amino acid sequence of H3-heavy)

<400> SEQUENCE: 41

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Thr Asp Tyr
         20                  25                  30

Tyr Met Ser Trp Val Arg Gln Ala Pro Gly Lys Gly Leu Glu Trp Leu
     35                  40                  45

Gly Phe Ile Arg Asn Lys Ala Asn Gly Tyr Thr Thr Glu Tyr Ser Ala
 50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Ala Glu Asp Thr Ala Val Tyr
                 85                  90                  95

Tyr Cys Ala Arg Asp Asn Trp Phe Ala Tyr Trp Gly Gln Gly Thr Leu
             100                 105                 110

Val Thr Val Ser Ser Ala Ser Thr Lys Gly Pro Ser Val Phe Pro Leu
         115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                 165                 170                 175

Ser Gly Leu Tyr Ser Leu Ser Ser Val Val Thr Val Pro Ser Ser Ser
             180                 185                 190

Leu Gly Thr Gln Thr Tyr Ile Cys Asn Val Asn His Lys Pro Ser Asn
         195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                 245                 250                 255

Pro Glu Val Thr Cys Val Val Val Asp Val Ser His Glu Asp Pro Glu
             260                 265                 270

Val Lys Phe Asn Trp Tyr Val Asp Gly Val Glu Val His Asn Ala Lys
         275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                 325                 330                 335

Ser Lys Ala Lys Gly Gln Pro Arg Glu Pro Gln Val Tyr Thr Leu Pro
             340                 345                 350

Pro Ser Arg Glu Glu Met Thr Lys Asn Gln Val Ser Leu Thr Cys Leu
         355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                 405                 410                 415

Trp Gln Gln Gly Asn Val Phe Ser Cys Ser Val Met His Glu Ala Leu
             420                 425                 430
```

His Asn His Tyr Thr Gln Lys Ser Leu Ser Leu Ser Pro Gly Lys
            435                 440                 445

<210> SEQ ID NO 42
<211> LENGTH: 447
<212> TYPE: PRT
<213> ORGANISM: Artificial Sequence
<220> FEATURE:
<223> OTHER INFORMATION: Synthetic (amino acid sequence of H4-heavy)

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

```
Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 43
<211> LENGTH: 220
<212> TYPE: PRT
<213> ORGANISM: Artificial Sequence
<220> FEATURE:
<223> OTHER INFORMATION: Synthetic (amino acid sequence of H1-light)

<400> SEQUENCE: 43

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 44
<211> LENGTH: 220
<212> TYPE: PRT
<213> ORGANISM: Artificial Sequence
<220> FEATURE:
<223> OTHER INFORMATION: Synthetic (amino acid sequence of H2-light)

<400> SEQUENCE: 44
```

```
Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Ala Ser
            20                  25                  30

Gly Asn Gln Asn Asn Tyr Leu Ala Trp His Leu Gln Lys Pro Gly Gln
        35                  40                  45

Ser Pro Gln Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Ser Tyr Ser Ala Pro Leu Thr Phe Gly Gln Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 45
<211> LENGTH: 220
<212> TYPE: PRT
<213> ORGANISM: Artificial Sequence
<220> FEATURE:
<223> OTHER INFORMATION: Synthetic (amino acid sequence of H3-light)

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp Tyr Gln Gln Lys Pro Gly Gln
        35                  40                  45

Pro Pro Lys Leu Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140
```

```
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 46
<211> LENGTH: 219
<212> TYPE: PRT
<213> ORGANISM: Artificial Sequence
<220> FEATURE:
<223> OTHER INFORMATION: Synthetic (amino acid sequence of H4-light)

<400> SEQUENCE: 46

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu
    210                 215
```

<210> SEQ ID NO 47
<211> LENGTH: 1350
<212> TYPE: DNA
<213> ORGANISM: Artificial Sequence
<220> FEATURE:
<223> OTHER INFORMATION: Synthetic (nucleotide sequence of H1-heavy)

<400> SEQUENCE: 47

```
gaggtgcagc tggtggagtc tgggggaggc ttggtccagc ctggagggtc cctgagactc    60
```

```
tcctgtgcag cctctggatt caccttcact gactactaca tgagctgggt ccgccaggct        120
ccagggaagg ggctggagtg gttgggcttt attagaaaca aagctaacgg ttacaccaca        180
gaatacagtg cgtctgtgaa aggcagattc accatctcaa gagataattc aaagaactca        240
ctgtatctgc aaatgaacag cctgaaaacc gaggacacgg ccgtgtatta ctgtgctaga        300
gataactggt ttgcttactg gggtcaagga accctggtca ccgtctcctc ggctagcacc        360
aagggcccat cggtcttccc cctggcaccc tcctccaaga gcacctctgg gggcacagcg        420
gccctgggct gcctggtcaa ggactacttc cccgaaccgg tgacggtgtc gtggaactca        480
ggcgccctga ccagcggcgt gcacaccttc ccggctgtcc tacagtcctc aggactctac        540
tccctcagca gcgtggtgac cgtgccctcc agcagcttgg gcacccagac ctacatctgc        600
aacgtgaatc acaagcccag caacaccaag gtggacaaga agttgagcc caaatcttgt         660 gacaaaactc acacatgccc accgtgccca gcacctgaac tcctgggggg accgtcagtc        720
ttcctcttcc ccccaaaacc caaggacacc ctcatgatct cccggacccc tgaggtcaca        780
tgcgtggtgg tggacgtgag ccacgaagac cctgaggtca agttcaactg gtacgtggac        840
ggcgtggagg tgcataatgc caagacaaag ccgcgggagg agcagtacaa cagcacgtac        900
cgtgtggtca gcgtcctcac cgtcctgcac caggactggc tgaatggcaa ggagtacaag        960
tgcaaggtct ccaacaaagc cctcccagcc cccatcgaga aaaccatctc caaagccaaa       1020
gggcagcccc gagaaccaca ggtgtacacc ctgcccccat cccgggagga gatgaccaag       1080
aaccaggtca gcctgacctg cctggtcaaa ggcttctatc ccagcgacat cgccgtggag       1140
tgggagagca atgggcagcc ggagaacaac tacaagacca cgcctcccgt gctggactcc       1200
gacggctcct tcttcctcta cagcaagctc accgtggaca agagcaggtg gcagcagggg       1260
aacgtcttct catgctccgt gatgcatgag gctctgcaca accactacac gcagaagagc       1320
ctctccctgt ctccgggtaa atgactcgag                                        1350
```

<210> SEQ ID NO 48
<211> LENGTH: 1350
<212> TYPE: DNA
<213> ORGANISM: Artificial Sequence
<220> FEATURE:
<223> OTHER INFORMATION: Synthetic (nucleotide sequence of H3-heavy)

<400> SEQUENCE: 48

```
gaggtgcagc tggtggagtc tgggggaggc ttggtccagc ctggagggtc cctgagactc         60
tcctgtgcag cctctggatt caccttcact gactactaca tgagctgggt ccgccaggct        120
ccagggaagg ggctggagtg gttgggcttt attagaaaca aagctaacgg ttacaccaca        180
gaatacagtg cgtctgtgaa aggcagattc accatctcaa gagataattc aaagaactca        240
ctgtatctgc aaatgaacag cctgcgtgct gaggacacgg ccgtgtatta ctgtgctaga        300
gataactggt ttgcttactg gggtcaagga accctggtca ccgtctcctc ggctagcacc        360
aagggcccat cggtcttccc cctggcaccc tcctccaaga gcacctctgg gggcacagcg        420
gccctgggct gcctggtcaa ggactacttc cccgaaccgg tgacggtgtc gtggaactca        480
ggcgccctga ccagcggcgt gcacaccttc ccggctgtcc tacagtcctc aggactctac        540
tccctcagca gcgtggtgac cgtgccctcc agcagcttgg gcacccagac ctacatctgc        600
aacgtgaatc acaagcccag caacaccaag gtggacaaga agttgagcc caaatcttgt         660 gacaaaactc acacatgccc accgtgccca gcacctgaac tcctgggggg accgtcagtc        720
```

```
ttcctcttcc ccccaaaacc caaggacacc ctcatgatct cccggacccc tgaggtcaca      780
tgcgtggtgg tggacgtgag ccacgaagac cctgaggtca agttcaactg gtacgtggac      840
ggcgtggagg tgcataatgc caagacaaag ccgcgggagg agcagtacaa cagcacgtac      900
cgtgtggtca gcgtcctcac cgtcctgcac caggactggc tgaatggcaa ggagtacaag      960
tgcaaggtct ccaacaaagc cctcccagcc cccatcgaga aaaccatctc caaagccaaa     1020
gggcagcccc gagaaccaca ggtgtacacc ctgcccccat cccgggagga gatgaccaag     1080
aaccaggtca gcctgacctg cctggtcaaa ggcttctatc ccagcgacat cgccgtggag     1140
tgggagagca atgggcagcc ggagaacaac tacaagacca cgcctcccgt gctggactcc     1200
gacggctcct tcttcctcta cagcaagctc accgtggaca agagcaggtg gcagcagggg     1260
aacgtcttct catgctccgt gatgcatgag gctctgcaca accactacac gcagaagagc     1320
ctctccctgt ctccgggtaa atgactcgag                                      1350
```

<210> SEQ ID NO 49
<211> LENGTH: 1350
<212> TYPE: DNA
<213> ORGANISM: Artificial Sequence
<220> FEATURE:
<223> OTHER INFORMATION: Synthetic (nucleotide sequence of H4-heavy)

<400> SEQUENCE: 49

```
gaggttcagc tggtggagtc tggcggtggc ctggtgcagc caggggggctc actccgtttg       60 tcctgtgcag cttctggctt caccttcact gattactaca tgagctgggt gcgtcaggcc      120
ccgggtaagg gcctggaatg gttgggtttt attagaaaca agctaatgg ttacacaaca       180 gagtacagtg catctgtgaa gggtcgtttc actataagca gagataattc caaaaacaca      240
ctgtacctgc agatgaacag cctgcgtgct gaggacactg ccgtctatta ttgtgctaga      300
gataactggt ttgcttactg gggccaaggg actctggtca ccgtctcctc ggctagcacc      360
aagggcccat cggtcttccc cctggcaccc tcctccaaga gcacctctgg gggcacagcg      420
gccctgggct gcctggtcaa ggactacttc cccgaaccgg tgacggtgtc gtggaactca      480
ggcgccctga ccagcggcgt gcacaccttc ccggctgtcc tacagtcctc aggactctac      540
tccctcagca gcgtggtgac cgtgccctcc agcagcttgg gcacccagac ctacatctgc      600
aacgtgaatc acaagcccag caacaccaag gtggacaaga agttgagcc caaatcttgt       660 gacaaaactc acacatgccc accgtgccca gcacctgaac tcctgggggg accgtcagtc      720
ttcctcttcc ccccaaaacc caaggacacc ctcatgatct cccggacccc tgaggtcaca      780
tgcgtggtgg tggacgtgag ccacgaagac cctgaggtca agttcaactg gtacgtggac      840
ggcgtggagg tgcataatgc caagacaaag ccgcgggagg agcagtacaa cagcacgtac      900
cgtgtggtca gcgtcctcac cgtcctgcac caggactggc tgaatggcaa ggagtacaag      960
tgcaaggtct ccaacaaagc cctcccagcc cccatcgaga aaaccatctc caaagccaaa     1020
gggcagcccc gagaaccaca ggtgtacacc ctgcccccat cccgggagga gatgaccaag     1080
aaccaggtca gcctgacctg cctggtcaaa ggcttctatc ccagcgacat cgccgtggag     1140
tgggagagca atgggcagcc ggagaacaac tacaagacca cgcctcccgt gctggactcc     1200
gacggctcct tcttcctcta cagcaagctc accgtggaca agagcaggtg gcagcagggg     1260
aacgtcttct catgctccgt gatgcatgag gctctgcaca accactacac gcagaagagc     1320
ctctccctgt ctccgggtaa atgactcgag                                      1350
```

<210> SEQ ID NO 50
<211> LENGTH: 669
<212> TYPE: DNA
<213> ORGANISM: Artificial Sequence
<220> FEATURE:
<223> OTHER INFORMATION: Synthetic (nucleotide sequence of H1-light)

<400> SEQUENCE: 50

```
gacatcgtga tgacccagtc tccagactcc ctggctgtgt ctctgggcga gagggccacc      60
atcaactgca gtccagcca gagtcttta gctagcggca accaaaataa ctacttagct      120
tggcaccagc agaaaccagg acagcctcct aagatgctca ttatttgggc atctacccgg    180
gtatccgggg tccctgaccg attcagtggc agcgggtctg ggacagattt cactctcacc    240
atcagcagcc tgcaggctga agatgtggca gtttattact gtcagcaatc ctatagtgct    300
cctctcacgt tcggaggcgg taccaaggtg gagatcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga aacacaaagt ctacgcctgc    600
gaagtcaccc atcagggcct gagctcgccc gtcacaaaga gcttcaacag gggagagtgt    660
tgactcgag                                                              669
```

<210> SEQ ID NO 51
<211> LENGTH: 669
<212> TYPE: DNA
<213> ORGANISM: Artificial Sequence
<220> FEATURE:
<223> OTHER INFORMATION: Synthetic (nucleotide sequence of H2-light)

<400> SEQUENCE: 51

```
gatattgtga tgacccagac tccactctcc ctgcccgtca cccctggaga gccggcctcc      60
atctcctgca gtccagtca gagtctttta gctagtggca accaaaataa ctacttggcc      120
tggcacctgc agaagccagg gcagtctcca cagatgctga tcatttgggc atccactagg      180
gtatctggag tcccagacag gttcagtggc agtgggtcag gcactgattt cacactgaaa    240
atcagcaggg tggaggctga ggatgttgga gtttattact gccagcagtc ctacagcgct    300
ccgctcacgt tcggacaggg taccaagctg gagctcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga aacacaaagt ctacgcctgc    600
gaagtcaccc atcagggcct gagctcgccc gtcacaaaga gcttcaacag gggagagtgt    660
tgactcgag                                                              669
```

<210> SEQ ID NO 52
<211> LENGTH: 669
<212> TYPE: DNA
<213> ORGANISM: Artificial Sequence
<220> FEATURE:
<223> OTHER INFORMATION: Synthetic (nucleotide sequence of H3-light)

<400> SEQUENCE: 52

```
gacatcgtga tgacccagtc tccagactcc ctggctgtgt ctctgggcga gagggccacc      60
```

```
atcaactgca agtccagcca gagtcttta gctagcggca accaaaataa ctacttagct    120
tggtaccagc agaaaccagg acagcctcct aagctgctca ttatttgggc atctacccgg    180
gtatccgggg tccctgaccg attcagtggc agcgggtctg ggacagattt cactctcacc    240
atcagcagcc tgcaggctga agatgtggca gtttattact gtcagcaatc ctatagtgct    300
cctctcacgt tcggaggcgg taccaaggtg gagatcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga aacacaaagt ctacgcctgc    600
gaagtcaccc atcagggcct gagctcgccc gtcacaaaga gcttcaacag gggagagtgt    660
tgactcgag                                                            669

<210> SEQ ID NO 53
<211> LENGTH: 669
<212> TYPE: DNA
<213> ORGANISM: Artificial Sequence
<220> FEATURE:
<223> OTHER INFORMATION: Synthetic (nucleotide sequence of H4-light)

<400> SEQUENCE: 53
gatatccaga tgacccagtc cccgagctcc ctgtccgcct ctgtgggcga tagggtcacc     60
atcacctgca gtccagtca gagtctttta gctagtggca accaaaataa ctacttggcc    120
tggcaccaac agaaaccagg aaaagctccg aaaatgctga ttatttgggc atccactagg    180
gtatctggag tcccttctcg cttctctgga tccgggtctg ggacggattt cactctgacc    240
atcagcagtc tgcagccgga agacttcgca acttattact gtcagcagtc ctacagcgct    300
ccgctcacgt tcggacaggg taccaaggtg gagatcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga aacacaaagt ctacgcctgc    600
gaagtcaccc atcagggcct gagctcgccc gtcacaaaga gcttcaacag gggagagtgt    660
tgactcgag                                                            669

<210> SEQ ID NO 54
<211> LENGTH: 23
<212> TYPE: PRT
<213> ORGANISM: Artificial Sequence
<220> FEATURE:
<223> OTHER INFORMATION: Synthetic (linker between VH and VL)

<400> SEQUENCE: 54

Gly Leu Gly Gly Leu Gly Gly Gly Ser Gly Gly Gly Gly Ser Gly
1               5                   10                  15

Gly Ser Ser Gly Val Gly Ser
            20

<210> SEQ ID NO 55
<211> LENGTH: 1088
<212> TYPE: DNA
<213> ORGANISM: Artificial Sequence
<220> FEATURE:
<223> OTHER INFORMATION: Synthetic (polynucleotide encoding scFv of
``` huAbF46 antibody)

<400> SEQUENCE: 55

```
gctagcgttt tagcagaagt tcaattggtt gaatctggtg gtggtttggt tcaaccaggt    60
ggttctttga gattgtcttg tgctgcttct ggttttactt tcaccgatta ttacatgtcc   120
tgggttagac aagctccagg taaaggtttg aatggttgg gtttcattag aaacaaggct    180
aacggttaca ctaccgaata ttctgcttct gttaagggta gattcaccat ttctagagac   240
aactctaaga cacccttgta cttgcaaatg aactccttga gagctgaaga tactgctgtt   300
tattactgcg ctagagataa ttggtttgct tattggggtc aaggtacttt ggttactgtt   360
tcttctggcc tcgggggcct cggaggagga ggtagtggcg gaggaggctc cggtggatcc   420
agcggtgtgg gttccgatat tcaaatgacc caatctccat cttctttgtc tgcttcagtt   480
ggtgatagag ttaccattac ttgtaagtcc tcccaatctt tgttggcttc tggtaatcag   540
aacaattact ggcttggcca tcaacaaaaa ccaggtaaag ctccaaagat gttgattatt   600
tgggcttcta ccagagtttc tggtgttcca tctagatttt ctggttctgg ttccggtact   660
gattttactt tgaccatttc atccttgcaa ccagaagatt tcgctactta ctactgtcaa   720
caatcttact ctgctccatt gactttggt caaggtacaa aggtcgaaat caagagagaa    780
ttcggtaagc ctatccctaa ccctctcctc ggtctcgatt ctacgggtgg tgtggatct    840
ggtggtggtg ttctggtgg tggtggttct caggaactga caactatatg cgagcaaatc   900
ccctcaccaa ctttagaatc gacgccgtac tctttgtcaa cgactactat tttggccaac   960
gggaaggcaa tgcaaggagt ttttgaatat tacaaatcag taacgtttgt cagtaattgc  1020
ggttctcacc cctcaacaac tagcaaaggc agccccataa acacacagta tgttttttga  1080
gtttaaac                                                            1088
```

<210> SEQ ID NO 56
<211> LENGTH: 5597
<212> TYPE: DNA
<213> ORGANISM: Artificial Sequence
<220> FEATURE:
<223> OTHER INFORMATION: Synthetic (expression vector including polynucleotide encoding scFv of huAbF46 antibody)
<220> FEATURE:
<221> NAME/KEY: misc_difference
<222> LOCATION: (573)..(578)
<223> OTHER INFORMATION: NheI restriction site
<220> FEATURE:
<221> NAME/KEY: misc_difference
<222> LOCATION: (588)..(938)
<223> OTHER INFORMATION: huAbF46 VH
<220> FEATURE:
<221> NAME/KEY: misc_difference
<222> LOCATION: (939)..(1007)
<223> OTHER INFORMATION: linker
<220> FEATURE:
<221> NAME/KEY: misc_difference
<222> LOCATION: (1008)..(1349)
<223> OTHER INFORMATION: huAbF46 VL
<220> FEATURE:
<221> NAME/KEY: misc_difference
<222> LOCATION: (1350)..(1355)
<223> OTHER INFORMATION: EcoRI restriction site
<220> FEATURE:
<221> NAME/KEY: misc_difference
<222> LOCATION: (1356)..(1397)
<223> OTHER INFORMATION: V5 epitope
<220> FEATURE:
<221> NAME/KEY: misc_difference
<222> LOCATION: (1398)..(1442)
<223> OTHER INFORMATION: (G4S)3 linker
<220> FEATURE:

<221> NAME/KEY: misc_difference
<222> LOCATION: (1443)..(1649)
<223> OTHER INFORMATION: Aga2
<220> FEATURE:
<221> NAME/KEY: misc_difference
<222> LOCATION: (1650)..(1652)
<223> OTHER INFORMATION: TGA(stop codon)
<220> FEATURE:
<221> NAME/KEY: misc_difference
<222> LOCATION: (1653)..(1660)
<223> OTHER INFORMATION: PmeI restriction site

<400> SEQUENCE: 56

```
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagttttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaaatac    480
gactcactat agggaatatt aagctaattc tacttcatac attttcaatt aagatgcagt     540
tacttcgctg ttttttcaata ttttctgtta ttgctagcgt tttagcagaa gttcaattgg    600
ttgaatctgg tggtggtttg gttcaaccag gtggttcttt gagattgtct tgtgctgctt     660
ctggttttac tttcaccgat tattacatgt cctgggttag acaagctcca ggtaaaggtt     720
tggaatggtt gggtttcatt agaaacaagg ctaacggtta cactaccgaa tattctgctt     780
ctgttaaggg tagattcacc atttctagag acaactctaa gaacaccttg tacttgcaaa     840
tgaactccct tgagagctgaa gatactgctg tttattactg cgctagagat aattggtttg     900
cttattgggg tcaaggtact ttggttactg ttttcttctgg cctcggggc ctcggaggag      960
gaggtagtgg cggaggaggc tccggtggat ccagcggtgt gggttccgat attcaaatga    1020
cccaatctcc atcttctttg tctgcttcag ttggtgatag agttaccatt acttgtaagt    1080
cctcccaatc tttgttggct tctggtaatc agaacaatta cttggcttgg catcaacaaa    1140
aaccaggtaa agctccaaag atgttgatta tttgggcttc taccagagtt tctggtgttc    1200
catctagatt ttctggttct ggttccggta ctgattttac tttgaccatt tcatccttgc    1260
aaccagaaga tttcgctact tactactgtc aacaatctta ctctgctcca ttgacttttg    1320
gtcaaggtac aaaggtcgaa atcaagagag aattcggtaa gcctatccct aaccctctcc    1380
tcggtctcga ttctacgggt ggtggtggat ctggtggtgg tggttctggt ggtggtggtt    1440
ctcaggaact gacaactata tgcgagcaaa tcccctcacc aactttagaa tcgacgccgt    1500
actctttgtc aacgactact attttggcca acgggaaggc aatgcaagga gttttttgaat   1560
attacaaatc agtaacgttt gtcagtaatt gcggttctca cccctcaaca actagcaaag    1620
gcagccccat aaacacacag tatgttttttt gagtttaaac ccgctgatct gataacaaca    1680
gtgtagatgt aacaaaatcg actttgttcc cactgtactt ttagctcgta caaaatacaa    1740
tatacttttc atttctccgt aaacaacatg ttttcccatg taatatcctt ttctattttt    1800
cgttccgtta ccaactttac acatacttta tatagctatt cacttctata cactaaaaaa    1860
ctaagacaat tttaattttg ctgcctgcca tatttcaatt tgttataaat tcctataatt    1920
tatcctatta gtagctaaaa aaagatgaat gtgaatcgaa tcctaagaga attgggcaag    1980
```

```
tgcacaaaca atacttaaat aaatactact cagtaataac ctatttctta gcattttga    2040 cgaaatttgc tattttgtta gagtctttta caccatttgt ctccacacct ccgcttacat    2100
caacaccaat aacgccattt aatctaagcg catcaccaac attttctggc gtcagtccac    2160
cagctaacat aaaatgtaag ctctcggggc tctcttgcct tccaacccag tcagaaatcg    2220
agttccaatc caaaagttca cctgtcccac ctgcttctga atcaaacaag ggaataaacg    2280
aatgaggttt ctgtgaagct gcactgagta gtatgttgca gtcttttgga aatacgagtc    2340
ttttaataac tggcaaaccg aggaactctt ggtattcttg ccacgactca tctccgtgca    2400
gttggacgat atcaatgccg taatcattga ccagagccaa aacatcctcc ttaggttgat    2460
tacgaaacac gccaaccaag tatttcggag tgcctgaact attttatat gcttttacaa    2520 gacttgaaat tttccttgca ataaccgggt caattgttct ctttctattg ggcacacata    2580
taatacccag caagtcagca tcggaatcta gagcacattc tgcggcctct gtgctctgca    2640
agccgcaaac tttcaccaat ggaccagaac tacctgtgaa attaataaca gacatactcc    2700
aagctgcctt tgtgtgctta atcacgtata ctcacgtgct caatagtcac caatgccctc    2760
cctcttggcc ctctccttt ctttttcga ccgaatttct tgaagacgaa agggcctcgt    2820
gatacgccta ttttatagg ttaatgtcat gataataatg gtttcttagg acggatcgct    2880
tgcctgtaac ttcacgcgc ctcgtatctt ttaatgatgg aataatttgg gaatttactc    2940
tgtgtttatt tattttatg ttttgtattt ggattttaga aagtaaataa agaaggtaga    3000
agagttacgg aatgaagaaa aaaaaataaa caaaggttta aaaatttca acaaaaagcg    3060 tactttacat atatatttat tagacaagaa aagcagatta aatagatata cattcgatta    3120
acgataagta aaatgtaaaa tcacaggatt ttcgtgtgtg gtcttctaca cagacaagat    3180
gaaacaattc ggcattaata cctgagagca ggaagagcaa gataaaggt agtatttgtt    3240 ggcgatcccc ctagagtctt ttacatcttc ggaaaacaaa aactatttt tctttaattt    3300 cttttttac tttctatttt taatttatat atttatatta aaaatttaa attataatta    3360 tttttatagc acgtgatgaa aaggacccag gtggcacttt tcggggaaat gtgcgcggaa    3420
cccctatttg tttattttc taaatacatt caaatatgta tccgctcatg agacaataac    3480
cctgataaat gcttcaataa tattgaaaaa ggaagagtat gagtattcaa catttccgtg    3540
tcgcccttat tccctttttt gcggcatttt gccttcctgt ttttgctcac ccagaaacgc    3600
tggtgaaagt aaaagatgct gaagatcagt tgggtgcacg agtgggttac atcgaactgg    3660
atctcaacag cggtaagatc cttgagagtt ttcgccccga agaacgtttt ccaatgatga    3720
gcacttttaa agttctgcta tgtggcgcgg tattatcccg tgttgacgcc gggcaagagc    3780
aactcggtcg ccgcatacac tattctcaga atgacttggt tgagtactca ccagtcacag    3840
aaaagcatct tacggatggc atgacagtaa gagaattatg cagtgctgcc ataaccatga    3900
gtgataacac tgcggccaac ttacttctga acgatcgg aggaccgaag gagctaaccg    3960 ctttttgca acatgggg gatcatgtaa ctcgccttga tcgttgggaa ccggagctga    4020
atgaagccat accaaacgac gagcgtgaca ccacgatgcc tgtagcaatg gcaacaacgt    4080
tgcgcaaact attaactggc gaactactta ctctagcttc ccggcaacaa ttaatagact    4140
ggatggaggc ggataaagtt gcaggaccac ttctgcgctc ggcccttccg gctggctggt    4200
ttattgctga taaatctgga gccggtgagc gtgggtctcg cggtatcatt gcagcactgg    4260
ggccagatgg taagccctcc cgtatcgtag ttatctacac gacgggcagt caggcaacta    4320
```

```
tggatgaacg aaatagacag atcgctgaga taggtgcctc actgattaag cattggtaac    4380
tgtcagacca agtttactca tatatacttt agattgattt aaaacttcat ttttaattta    4440
aaaggatcta ggtgaagatc cttttgata atctcatgac caaaatccct taacgtgagt    4500
tttcgttcca ctgagcgtca gacccgtag aaaagatcaa aggatcttct tgagatcctt    4560
tttttctgcg cgtaatctgc tgcttgcaaa caaaaaaacc accgctacca gcggtggttt    4620
gtttgccgga tcaagagcta ccaactcttt ttccgaaggt aactggcttc agcagagcgc    4680
agataccaaa tactgtcctt ctagtgtagc cgtagttagg ccaccacttc aagaactctg    4740
tagcaccgcc tacatacctc gctctgctaa tcctgttacc agtggctgct gccagtggcg    4800
ataagtcgtg tcttaccggg ttggactcaa gacgatagtt accggataag cgcagcggt    4860 cgggctgaac ggggggttcg tgcacacagc ccagcttgga gcgaacgacc tacaccgaac    4920
tgagatacct acagcgtgag cattgagaaa gcgccacgct tcccgaaggg agaaaggcgg    4980
acaggtatcc ggtaagcggc agggtcggaa caggagagcg cacgagggag cttccagggg    5040
ggaacgcctg gtatctttat agtcctgtcg ggtttcgcca cctctgactt gagcgtcgat    5100
ttttgtgatg ctcgtcaggg gggcggagcc tatggaaaaa cgccagcaac gcggcctttt    5160
tacggttcct ggccttttgc tggccttttg ctcacatgtt ctttcctgcg ttatcccctg    5220
attctgtgga taaccgtatt accgcctttg agtgagctga taccgctcgc cgcagccgaa    5280
cgaccgagcg cagcgagtca gtgagcgagg aagcggaaga gcgcccaata cgcaaaccgc    5340
ctctccccgc gcgttggccg attcattaat gcagctggca cgacaggttt cccgactgga    5400
aagcgggcag tgagcgcaac gcaattaatg tgagttacct cactcattag gcaccccagg    5460
ctttacactt tatgcttccg gctcctatgt tgtgtggaat tgtgagcgga taacaatttc    5520
acacaggaaa cagctatgac catgattacg ccaagctcgg aattaaccct cactaaaggg    5580
aacaaaagct ggctagt    5597
```

<210> SEQ ID NO 57  
<211> LENGTH: 13  
<212> TYPE: PRT  
<213> ORGANISM: Artificial Sequence  
<220> FEATURE:  
<223> OTHER INFORMATION: Synthetic (U6-HC7 hinge)

<400> SEQUENCE: 57

Glu Pro Lys Ser Cys Asp Cys His Cys Pro Pro Cys Pro  
1               5                   10

<210> SEQ ID NO 58  
<211> LENGTH: 435  
<212> TYPE: DNA  
<213> ORGANISM: Artificial Sequence  
<220> FEATURE:  
<223> OTHER INFORMATION: Synthetic (polynucleotide encoding CDR-L3 derived from L3-1 clone)

<400> SEQUENCE: 58

```
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca gtccagtca gagtctttta    180 gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg gaacggattt cactctgacc atcagcagtc tgcagccgga agacttcgca    360
```

```
acttattact gtcagcagtc ctacagccgc ccgtacacgt tcggacaggg taccaaggtg    420
gagatcaaac gtacg                                                     435
```

<210> SEQ ID NO 59
<211> LENGTH: 435
<212> TYPE: DNA
<213> ORGANISM: Artificial Sequence
<220> FEATURE:
<223> OTHER INFORMATION: Synthetic (polynucleotide encoding CDR-L3 derived from L3-2 clone)

<400> SEQUENCE: 59

```
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca agtccagtca gagtctttta    180
gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg gacggattt cactctgacc atcagcagtc tgcagccgga agacttcgca    360
acttattact gtgggcagtc ctacagccgt ccgctcacgt tcggacaggg taccaaggtg    420
gagatcaaac gtacg                                                     435
```

<210> SEQ ID NO 60
<211> LENGTH: 435
<212> TYPE: DNA
<213> ORGANISM: Artificial Sequence
<220> FEATURE:
<223> OTHER INFORMATION: Synthetic (polynucleotide encoding CDR-L3 derived from L3-3 clone)

<400> SEQUENCE: 60

```
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca agtccagtca gagtctttta    180
gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg gacggattt cactctgacc atcagcagtc tgcagccgga agacttcgca    360
acttattact gtgcacagtc ctacagccat ccgttctctt tcggacaggg taccaaggtg    420
gagatcaaac gtacg                                                     435
```

<210> SEQ ID NO 61
<211> LENGTH: 435
<212> TYPE: DNA
<213> ORGANISM: Artificial Sequence
<220> FEATURE:
<223> OTHER INFORMATION: Synthetic (polynucleotide encoding CDR-L3 derived from L3-5 clone)

<400> SEQUENCE: 61

```
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca agtccagtca gagtctttta    180
gctagtggca accaaaataa ctacttggcc tggcaccaac agaaaccagg aaaagctccg    240
aaaatgctga ttatttgggc atccactagg gtatctggag tcccttctcg cttctctgga    300
```

-continued

```
tccgggtctg ggacggattt cactctgacc atcagcagtc tgcagccgga agacttcgca    360
acttattact gtcagcagtc ctacagccgc ccgtttacgt tcggacaggg taccaaggtg    420
gagatcaaac gtacg                                                     435
```

<210> SEQ ID NO 62
<211> LENGTH: 462
<212> TYPE: PRT
<213> ORGANISM: Artificial Sequence
<220> FEATURE:
<223> OTHER INFORMATION: Synthetic (polypeptide consisting of heavy
      chain of huAbF46-H4-A1, U6-HC7 hinge and constant region
      of human IgG1)

<400> SEQUENCE: 62

Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
                20                  25                  30

Gly Ser Leu Arg Leu Ser Cys Ala Ala Ser Gly Phe Thr Phe Thr Asp
            35                  40                  45

Tyr Tyr Met Ser Trp Val Arg Gln Ala Pro Gly Lys Gly Leu Glu Trp
        50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Cys His
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
            325                 330                 335

Lys Val Ser Asn Lys Ala Leu Pro Ala Pro Ile Glu Lys Thr Ile Ser
        340                 345                 350

Lys Ala Lys Gly Gln Pro Arg Glu Pro Gln Val Tyr Thr Leu Pro Pro
    355                 360                 365

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 63
<211> LENGTH: 1410
<212> TYPE: DNA
<213> ORGANISM: Artificial Sequence
<220> FEATURE:
<223> OTHER INFORMATION: Synthetic (polynucleotide encoding polypeptide
      consisting of heavy chain of huAbF46-H4-A1, U6-HC7
      hinge and constant region of human IgG1)

<400> SEQUENCE: 63
gaattcgccg ccaccatgga atggagctgg gtttttctcg taacactttt aaatggtatc      60
cagtgtgagg ttcagctggt ggagtctggc ggtggcctgg tgcagccagg gggctcactc     120
cgtttgtcct gtgcagcttc tggcttcacc ttcactgatt actacatgag ctgggtgcgt     180
caggccccgg gtaagggcct ggaatggttg gttttattta gaaacaaagc taatggttac     240
acaacagagt acagtgcatc tgtgaagggt cgtttcacta taagcagaga taattccaaa     300
aacacactgt acctgcagat gaacagcctg cgtgctgagg acactgccgt ctattattgt     360
gctagagata actggtttgc ttactggggc aagggactct ggtcaccgt ctcctcggct     420 agcaccaagg gcccatcggt cttccccctg gcaccctcct ccaagagcac ctctgggggc     480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
agctgcgatt gccactgtcc tccatgtcca gcacctgaac tcctgggggg accgtcagtc     780
ttcctcttcc ccccaaaacc caaggacacc ctcatgatct cccggacccc tgaggtcaca     840
tgcgtggtgg tggacgtgag ccacgaagac cctgaggtca agttcaactg gtacgtggac     900
ggcgtggagg tgcataatgc caagacaaag ccgcgggagg agcagtacaa cagcacgtac     960
cgtgtggtca gcgtcctcac cgtcctgcac caggactggc tgaatggcaa ggagtacaag    1020
tgcaaggtct ccaacaaagc cctcccagcc cccatcgaga aaaccatctc caaagccaaa    1080
gggcagcccc gagaaccaca ggtgtacacc ctgcccccat cccgggagga gatgaccaag    1140
aaccaggtca gcctgacctg cctggtcaaa ggcttctatc ccagcgacat cgccgtggag    1200

```
tgggagagca atgggcagcc ggagaacaac tacaagacca cgcctcccgt gctggactcc    1260
gacggctcct tcttcctcta cagcaagctc accgtggaca agagcaggtg gcagcagggg    1320
aacgtcttct catgctccgt gatgcatgag gctctgcaca accactacac gcagaagagc    1380
ctctccctgt ctccgggtaa atgactcgag                                     1410
```

<210> SEQ ID NO 64
<211> LENGTH: 461
<212> TYPE: PRT
<213> ORGANISM: Artificial Sequence
<220> FEATURE:
<223> OTHER INFORMATION: Synthetic (polypeptide consisting of heavy
      chain of huAbF46-H4-A1, human IgG2 hinge and constant region
      of human IgG1)

<400> SEQUENCE: 64

```
Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Arg Lys Cys Cys Val Glu Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320
```

```
Thr Val Leu His Gln Asp Trp Leu Asn Gly Lys Glu Tyr Lys Cys Lys
            325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
            355                 360                 365

Arg Glu Glu Met Thr Lys Asn Gln Val Ser Leu Thr Cys Leu Val Lys
        370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
            435                 440                 445

His Tyr Thr Gln Lys Ser Leu Ser Leu Ser Pro Gly Lys
            450                 455                 460

<210> SEQ ID NO 65
<211> LENGTH: 1407
<212> TYPE: DNA
<213> ORGANISM: Artificial Sequence
<220> FEATURE:
<223> OTHER INFORMATION: Synthetic (polynucleotide encoding polypeptide
      consisting of heavy chain of huAbF46-H4-A1, human
      IgG2 hinge and constant region of human IgG1)

<400> SEQUENCE: 65
gaattcgccg ccaccatgga atggagctgg gttttcctcg taacactttt aaatggtatc      60
cagtgtgagg ttcagctggt ggagtctggc ggtggcctgg tgcagccagg gggctcactc     120
cgtttgtcct gtgcagcttc tggcttcacc ttcactgatt actacatgag ctgggtgcgt     180
caggccccgg gtaagggcct ggaatggttg ggttttatta gaaacaaagc taatggttac     240
acaacagagt acagtgcatc tgtgaagggt cgtttcacta taagcagaga taattccaaa     300
aacacactgt acctgcagat gaacagcctg cgtgctgagg acactgccgt ctattattgt     360
gctagagata ctggtttgc ttactggggc caagggactc tggtcaccgt ctcctcggct     420
agcaccaagg gcccatcggt cttccccctg gcaccctcct ccaagagcac ctctggggc     480 acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagaggaag     720
tgctgtgtgg agtgccccc ctgcccagca cctgaactcc tggggggacc gtcagtcttc     780
ctcttccccc caaaacccaa ggacaccctc atgatctccc ggacccctga ggtcacatgc     840
gtggtggtgg acgtgagcca cgaagaccct gaggtcaagt tcaactggta cgtggacggc     900
gtggaggtgc ataatgccaa gacaaagccg cgggaggagc agtacaacag cacgtaccgt     960
gtggtcagcg tcctcaccgt cctgcaccag gactggctga atggcaagga gtacaagtgc    1020
aaggtctcca acaaagccct cccagccccc atcgagaaaa ccatctccaa agccaagggg    1080
cagccccgag aaccacaggt gtacaccctg cccccatccc gggaggagat gaccaagaac    1140
caggtcagcc tgacctgcct ggtcaaaggc ttctatccca gcgacatcgc cgtggagtgg    1200
```

```
gagagcaatg ggcagccgga gaacaactac aagaccacgc ctcccgtgct ggactccgac    1260
ggctccttct tcctctacag caagctcacc gtggacaaga gcaggtggca gcagggGaac    1320
gtcttctcat gctccgtgat gcatgaggct ctgcacaacc actacacgca gaagagcctc    1380
tccctgtctc cgggtaaatg actcgag                                        1407

<210> SEQ ID NO 66
<211> LENGTH: 460
<212> TYPE: PRT
<213> ORGANISM: Artificial Sequence
<220> FEATURE:
<223> OTHER INFORMATION: Synthetic (polypeptide consisting of heavy
      chain of huAbF46-H4-A1, human IgG2 hinge and constant region
      of human IgG2)

<400> SEQUENCE: 66
```

Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Asn Phe Gly Thr Gln Thr Tyr Thr Cys Asn Val Asp His Lys Pro Ser
    210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Phe Arg Val Val Ser Val Leu Thr

```
              305                 310                 315                 320
Val Val His Gln Asp Trp Leu Asn Gly Lys Glu Tyr Lys Cys Lys Val
                    325                 330                 335

Ser Asn Lys Gly Leu Pro Ala Pro Ile Glu Lys Thr Ile Ser Lys Thr
                340                 345                 350

Lys Gly Gln Pro Arg Glu Pro Gln Val Tyr Thr Leu Pro Pro Ser Arg
            355                 360                 365

Glu Glu Met Thr Lys Asn Gln Val Ser Leu Thr Cys Leu Val Lys Gly
        370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
                420                 425                 430

Gly Asn Val Phe Ser Cys Ser Val Met His Glu Ala Leu His Asn His
                435                 440                 445

Tyr Thr Gln Lys Ser Leu Ser Leu Ser Pro Gly Lys
    450                 455                 460

<210> SEQ ID NO 67
<211> LENGTH: 1404
<212> TYPE: DNA
<213> ORGANISM: Artificial Sequence
<220> FEATURE:
<223> OTHER INFORMATION: Synthetic (polynucleotide encoding polypeptide
      consisting of heavy chain of huAbF46-H4-A1, human
      IgG2 hinge and constant region of human IgG2)

<400> SEQUENCE: 67
gaattcgccg ccaccatgga atggagctgg gttttcctcg taacactttt aaatggtatc      60
cagtgtgagg ttcagctggt ggagtctggc ggtggcctgg tgcagccagg gggctcactc     120
cgtttgtcct gtgcagcttc tggcttcacc ttcactgatt actacatgag ctgggtgcgt     180
caggccccgg gtaagggcct ggaatggttg gtttttatta gaaacaaagc taatggttac     240
acaacagagt acagtgcatc tgtgaagggt cgtttcacta taagcagaga taattccaaa     300
aacacactgt acctgcagat gaacagcctg cgtgctgagg acactgccgt ctattattgt     360
gctagagata ctggttttgc ttactggggc caagggactc tggtcaccgt ctcctcggct     420
agcaccaagg gcccatcggt cttccccctg gcgccctgct ccaggagcac ctccgagagc     480
acagcggccc tgggctgcct ggtcaaggac tacttccccg aaccggtgac ggtgtcgtgg     540
aactcaggcg ctctgaccag cggcgtgcac accttcccag ctgtcctaca gtcctcagga     600
ctctactccc tcagcagcgt ggtgaccgtg ccctccagca acttcggcac ccagacctac     660
acctgcaacg tagatcacaa gcccagcaac accaaggtgg acaagacagt tgagcgcaaa     720
tgttgtgtcg agtgcccacc gtgcccagca ccacctgtgg caggaccgtc agtcttcctc     780
ttccccccaa aacccaagga caccctcatg atctcccgga cccctgaggt cacgtgcgtg     840
gtggtggacg tgagccacga agaccccgag gtccagttca actggtacgt ggacggcgtg     900
gaggtgcata atgccaagac aaagccacgg gaggagcagt tcaacagcac gttccgtgtg     960
gtcagcgtcc tcaccgttgt gcaccaggac tggctgaacg gcaaggagta caagtgcaag    1020
gtctccaaca aaggcctccc agcccccatc gagaaaacca tctccaaaac caaagggcag    1080
ccccgagaac cacaggtgta caccctgccc ccatcccggg aggagatgac caagaaccag    1140
```

```
gtcagcctga cctgcctggt caaaggcttc tacccccagcg acatcgccgt ggagtgggag      1200
agcaatgggc agccggagaa caactacaag accacgcctc ccatgctgga ctccgacggc      1260
tccttcttcc tctacagcaa gctcaccgtg gacaagagca ggtggcagca ggggaacgtc      1320
ttctcatgct ccgtgatgca tgaggctctg cacaaccact acacgcagaa gagcctctcc      1380
ctgtctccgg gtaaatgact cgag                                             1404
```

<210> SEQ ID NO 68
<211> LENGTH: 240
<212> TYPE: PRT
<213> ORGANISM: Artificial Sequence
<220> FEATURE:
<223> OTHER INFORMATION: Synthetic (polypeptide consisting of light
      chain of huAbF46-H4-A1(H36Y) and human kappa constant region)

<400> SEQUENCE: 68

```
Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Leu Ala Ser Gly Asn Gln Asn Asn Tyr Leu Ala Trp Tyr Gln Gln
    50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 69
<211> LENGTH: 758
<212> TYPE: DNA
<213> ORGANISM: Artificial Sequence
<220> FEATURE:
<223> OTHER INFORMATION: Synthetic (polynucleotide encoding polypeptide
      consisting of light chain of huAbF46-H4-A1(H36Y) and
      human kappa constant region)

<400> SEQUENCE: 69

```
aattcactag tgattaattc gccgccacca tggattcaca ggcccaggtc ctcatgttgc      60
```

```
tgctgctatc ggtatctggt acctgtggag atatccagat gacccagtcc ccgagctccc      120
tgtccgcctc tgtgggcgat agggtcacca tcacctgcaa gtccagtcag agtcttttag      180
ctagtggcaa ccaaaataac tacttggcct ggtaccaaca gaaaccagga aaagctccga      240
aaatgctgat tatttgggca tccactaggg tatctggagt cccttctcgc ttctctggat      300
ccgggtctgg gacggatttc actctgacca tcagcagtct gcagccggaa gacttcgcaa      360
cttattactg tcagcagtcc tacagccgcc cgtacacgtt cggacagggt accaaggtgg      420
agatcaaacg tacggtggct gcaccatctg tcttcatctt cccgccatct gatgagcagt      480
tgaaatctgg aactgcctct gttgtgtgcc tgctgaataa cttctatccc agagaggcca      540
aagtacagtg gaaggtggat aacgccctcc aatcgggtaa ctcccaggag agtgtcacag      600
agcaggacag caaggacagc acctacagcc tcagcagcac cctgacgctg agcaaagcag      660
actacgagaa acacaaagtc tacgcctgcg aagtcaccca tcagggcctg agctcgcccg      720
tcacaaagag cttcaacagg ggagagtgtt gactcgag                              758
```

<210> SEQ ID NO 70
<211> LENGTH: 240
<212> TYPE: PRT
<213> ORGANISM: Artificial Sequence
<220> FEATURE:
<223> OTHER INFORMATION: Synthetic (polypeptide consisting of light
      chain of huAbF46-H4-A1 and human kappa constant region)

<400> SEQUENCE: 70

```
Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Leu Ala Ser Gly Asn Gln Asn Asn Tyr Leu Ala Trp His Gln Gln
    50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
```

<210> SEQ ID NO 71
<211> LENGTH: 19
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 71

Phe Ser Pro Gln Ile Glu Glu Pro Ser Gln Cys Pro Asp Cys Val Val
1               5                   10                  15

Ser Ala Leu

<210> SEQ ID NO 72
<211> LENGTH: 10
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 72

Pro Gln Ile Glu Glu Pro Ser Gln Cys Pro
1               5                   10

<210> SEQ ID NO 73
<211> LENGTH: 5
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 73

Glu Glu Pro Ser Gln
1               5

<210> SEQ ID NO 74
<211> LENGTH: 117
<212> TYPE: PRT
<213> ORGANISM: Artificial Sequence
<220> FEATURE:
<223> OTHER INFORMATION: Synthetic (heavy chain variable region of
      anti-c-Met antibody (AbF46 or huAbF46-H1))

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

```
<210> SEQ ID NO 75
<211> LENGTH: 114
<212> TYPE: PRT
<213> ORGANISM: Artificial Sequence
<220> FEATURE:
<223> OTHER INFORMATION: Synthetic (light chain variable region of
      anti-c-Met antibody (AbF46 or huAbF46-H1))

<400> SEQUENCE: 75

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg

<210> SEQ ID NO 76
<211> LENGTH: 1416
<212> TYPE: DNA
<213> ORGANISM: Artificial Sequence
<220> FEATURE:
<223> OTHER INFORMATION: Synthetic (nucleotide sequence of heavy chain
      of anti-c-Met antibody (AbF46 or huAbF46-H1))
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 76
gaattcgccg ccaccatgga atggagctgg gttttctcg taacactttt aaatggtatc      60
cagtgtgagg tgaagctggt ggagtctgga ggaggcttgg tacagcctgg gggttctctg    120
agactctcct gtgcaacttc tgggttcacc ttcactgatt actacatgag ctgggtccgc    180
cagcctccag gaaaggcact tgagtggttg ggttttatta gaaacaaagc taatggttac    240
```

```
acaacagagt acagtgcatc tgtgaagggt cggttcacca tctccagaga taattcccaa    300
agcatcctct atcttcaaat ggacaccctg agagctgagg acagtgccac ttattactgt    360
gcaagagata actggtttgc ttactggggc caagggactc tggtcactgt ctctgcagct    420
agcaccaagg gcccatcggt cttccccctg gcacctcct ccaagagcac ctctgggggc     480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttcccccc aaaacccaag gacaccctca tgatctcccg gacccctgag    840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag   1020
tacaagtgca aggtctccaa caaagccctc ccagccccca tcgagaaaac catctccaaa   1080
gccaaagggc agccccgaga accacaggtg tacaccctgc ccccatcccg ggaggagatg   1140
accaagaacc aggtcagcct gacctgcctg gtcaaaggct tctatcccag cgacatcgcc   1200
gtggagtggg agagcaatgg gcagccggag aacaactaca agaccacgcc tcccgtgctg   1260
gactccgacg gctccttctt cctctacagc aagctcaccg tggacaagag caggtggcag   1320
caggggaacg tcttctcatg ctccgtgatg catgaggctc tgcacaacca ctacacgcag   1380
aagagcctct ccctgtctcc gggtaaatga ctcgag                             1416
```

<210> SEQ ID NO 77
<211> LENGTH: 759
<212> TYPE: DNA
<213> ORGANISM: Artificial Sequence
<220> FEATURE:
<223> OTHER INFORMATION: Synthetic (nucleotide sequence of light chain
      of anti-c-Met antibody (AbF46 or huAbF46-H1))
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 77

```
gaattcacta gtgattaatt cgccgccacc atggattcac aggcccaggt cctcatgttg      60
ctgctgctat cggtatctgg tacctgtgga gacattttga tgacccagtc tccatcctcc     120
ctgactgtgt cagcaggaga aaggtcact atgagctgca agtccagtca gagtctttta      180
gctagtggca accaaaataa ctacttggcc tggcaccagc agaaaccagg acgatctcct     240
aaaatgctga taatttgggc atccactagg gtatctggag tccctgatcg cttcataggc     300
agtggatctg ggacggattt cactctgacc atcaacagtg tgcaggctga agatctggct     360
gtttattact gtcagcagtc ctacagcgct ccgctcacgt tcggtgctgg gaccaagctg     420
gagctgaaac gtacggtggc tgcaccatct gtcttcatct cccgccatc tgatgagcag      480 ttgaaatctg gaactgcctc tgttgtgtgc ctgctgaata acttctatcc cagagaggcc     540
aaagtacagt ggaaggtgga taacgccctc caatcgggta actcccagga gagtgtcaca     600
gagcaggaca gcaaggacag cacctacagc ctcagcagca ccctgacgct gagcaaagca     660
gactacgaga aacacaaagt ctacgcctgc gaagtcaccc atcagggcct gagctcgccc     720
gtcacaaaga gcttcaacag gggagagtgt tgactcgag                            759

<210> SEQ ID NO 78
<211> LENGTH: 4170
<212> TYPE: DNA
<213> ORGANISM: Artificial Sequence
<220> FEATURE:
<223> OTHER INFORMATION: Synthetic (polynucleotide encoding c-Met
      protein)

<400> SEQUENCE: 78
atgaaggccc ccgctgtgct tgcacctggc atcctcgtgc tcctgtttac cttggtgcag      60
aggagcaatg ggagtgtaa agaggcacta gcaaagtccg agatgaatgt gaatatgaag     120
tatcagcttc ccaacttcac cgcggaaaca cccatccaga atgtcattct acatgagcat     180
cacattttcc ttggtgccac taactacatt tatgttttaa atgaggaaga ccttcagaag     240
gttgctgagt acaagactgg gcctgtgctg gaacacccag attgtttccc atgtcaggac     300
tgcagcagca agccaatttt atcaggaggt gtttggaaag ataacatcaa catggctcta     360
gttgtcgaca cctactatga tgatcaactc attagctgtg gcagcgtcaa cagagggacc     420
tgccagcgac atgtctttcc ccacaatcat actgctgaca tacagtcgga ggttcactgc     480
atattctccc cacagataga agagcccagc cagtgtcctg actgtgtggt gagcgccctg     540
ggagccaaag tcctttcatc tgtaaaggac cggttcatca acttctttgt aggcaatacc     600
ataaattctt cttatttccc agatcatcca ttgcattcga tatcagtgag aaggctaaag     660
gaaacgaaag atggttttat gttttttgacg gaccagtcct acattgatgt tttacctgag     720
ttcagagatt cttaccccat taagtatgtc catgcctttg aaagcaacaa ttttatttac     780
ttcttgacgg tccaaaggga aactctagat gctcagactt tcacacaaga ataatcagg     840 ttctgttcca taaactctgg attgcattcc tacatggaaa tgcctctgga gtgtattctc     900
acagaaaaga gaaaaagag atccacaaag aaggaagtgt taatatact tcaggctgcg     960 tatgtcagca agcctgggc ccagcttgct agacaaatag agccagcct gaatgatgac    1020 attcttttcg gggtgttcgc acaaagcaag ccagattctg ccgaaccaat ggatcgatct    1080
gccatgtgtg cattccctat caaatatgtc aacgacttct caacaagat cgtcaacaaa    1140 aacaatgtga gatgtctcca gcatttttac ggacccaatc atgagcactg ctttaatagg    1200
acacttctga gaaattcatc aggctgtgaa gcgcgccgtg atgaatatcg aacagagttt    1260
```

```
accacagctt tgcagcgcgt tgacttattc atgggtcaat tcagcgaagt cctcttaaca   1320
tctatatcca ccttcattaa aggagacctc accatagcta atcttgggac atcagagggt   1380
cgcttcatgc aggttgtggt ttctcgatca ggaccatcaa cccctcatgt gaatttctc    1440
ctggactccc atccagtgtc tccagaagtg attgtggagc atacattaaa ccaaaatggc   1500
tacacactgg ttatcactgg gaagaagatc acgaagatcc cattgaatgg cttgggctgc   1560
agacatttcc agtcctgcag tcaatgcctc tctgccccac cctttgttca gtgtggctgg   1620
tgccacgaca aatgtgtgcg atcggaggaa tgcctgagcg ggacatggac tcaacagatc   1680
tgtctgcctg caatctacaa ggttttccca aatagtgcac cccttgaagg agggacaagg   1740
ctgaccatat gtggctggga ctttggattt cggaggaata taaatttga tttaaagaaa    1800
actagagttc ccttggaaa tgagagctgc accttgactt taagtgagag cacgatgaat    1860
acattgaaat gcacagttgg tcctgccatg aataagcatt tcaatatgtc cataattatt   1920
tcaaatggcc acgggacaac acaatacagt acattctcct atgtggatcc tgtaataaca   1980
agtatttcgc cgaaatacgg tcctatggct ggtggcactt tacttacttt aactggaaat   2040
tacctaaaca gtgggaattc tagacacatt tcaattggtg gaaaaacatg tactttaaaa   2100
agtgtgtcaa acagtattct tgaatgttat accccagccc aaaccatttc aactgagttt   2160
gctgttaaat tgaaaattga cttagccaac cgagagacaa gcatcttcag ttaccgtgaa   2220
gatcccattg tctatgaaat tcatccaacc aaatctttta ttagtggtgg gagcacaata   2280
acaggtgttg ggaaaaacct gaattcagtt agtgtcccga gaatggtcat aaatgtgcat   2340
gaagcaggaa ggaactttac agtggcatgt caacatcgct ctaattcaga gataatctgt   2400
tgtaccactc cttccctgca acagctgaat ctgcaactcc ccctgaaaac caaagccttt   2460
ttcatgttag atgggatcct ttccaaatac tttgatctca tttatgtaca taatcctgtg   2520
tttaagcctt ttgaaaagcc agtgatgatc tcaatgggca atgaaaatgt actggaaatt   2580
aagggaaatg atattgaccc tgaagcagtt aaaggtgaag tgttaaaagt tggaaataag   2640
agctgtgaga atatacactt acattctgaa gccgttttat gcacggtccc caatgacctg   2700
ctgaaattga acagcgagct aaatatagag tggaagcaag caatttcttc aaccgtcctt   2760
ggaaaagtaa tagttcaacc agatcagaat ttcacaggat tgattgctgg tgttgtctca   2820
atatcaacag cactgttatt actacttggg ttttcctgt ggctgaaaaa gagaaagcaa    2880
attaaagatc tgggcagtga attagttcgc tacgatgcaa gagtacacac tcctcatttg   2940
gataggcttg taagtgcccg aagtgtaagc ccaactacag aaatggtttc aaatgaatct   3000
gtagactacc gagctacttt tccagaagat cagtttccta attcatctca gaacggttca   3060
tgccgacaag tgcagtatcc tctgacagac atgtccccca tcctaactag tggggactct   3120
gatatatcca gtccattact gcaaaatact gtccacattg acctcagtgc tctaaatcca   3180
gagctggtcc aggcagtgca gcatgtagtg attgggccca gtagcctgat tgtgcatttc   3240
aatgaagtca taggaagagg gcattttggt tgtgtatatc atgggacttt gttggacaat   3300
gatggcaaga aaattcactg tgctgtgaaa tccttgaaca gaatcactga cataggagaa   3360
gtttcccaat ttctgaccga gggaatcatc atgaaagatt ttagtcatcc caatgtcctc   3420
tcgctcctgg gaatctgcct gcgaagtgaa gggtctccgc tggtggtcct accatacatg   3480
aaacatggag atcttcgaaa tttcattcga aatgagactc ataatccaac tgtaaaagat   3540
cttattggct ttggtcttca agtagccaaa ggcatgaaat atcttgcaag caaaagtttt   3600
```

-continued

```
gtccacagag acttggctgc aagaaactgt atgctggatg aaaaattcac agtcaaggtt    3660
gctgattttg gtcttgccag agacatgtat gataaagaat actatagtgt acacaacaaa    3720
acaggtgcaa agctgccagt gaagtggatg gctttggaaa gtctgcaaac tcaaaagttt    3780
accaccaagt cagatgtgtg gtcctttggc gtgctcctct gggagctgat gacaagagga    3840
gccccacctt atcctgacgt aaacaccttt gatataactg tttacttgtt gcaagggaga    3900
agactcctac aacccgaata ctgcccagac cccttatatg aagtaatgct aaaatgctgg    3960
caccctaaag ccgaaatgcg cccatccttt tctgaactgg tgtcccggat atcagcgatc    4020
ttctctactt tcattgggga gcactatgtc catgtgaacg ctacttatgt gaacgtaaaa    4080
tgtgtcgctc cgtatccttc tctgttgtca tcagaagata acgctgatga tgaggtggac    4140
acacgaccag cctccttctg ggagacatca                                     4170
```

<210> SEQ ID NO 79
<211> LENGTH: 444
<212> TYPE: PRT
<213> ORGANISM: Artificial Sequence
<220> FEATURE:
<223> OTHER INFORMATION: Synthetic (SEMA domain of c-Met)

<400> SEQUENCE: 79

```
Leu His Glu His His Ile Phe Leu Gly Ala Thr Asn Tyr Ile Tyr Val
1               5                   10                  15

Leu Asn Glu Glu Asp Leu Gln Lys Val Ala Glu Tyr Lys Thr Gly Pro
            20                  25                  30

Val Leu Glu His Pro Asp Cys Phe Pro Cys Gln Asp Cys Ser Ser Lys
        35                  40                  45

Ala Asn Leu Ser Gly Gly Val Trp Lys Asp Asn Ile Asn Met Ala Leu
    50                  55                  60

Val Val Asp Thr Tyr Tyr Asp Asp Gln Leu Ile Ser Cys Gly Ser Val
65                  70                  75                  80

Asn Arg Gly Thr Cys Gln Arg His Val Phe Pro His Asn His Thr Ala
                85                  90                  95

Asp Ile Gln Ser Glu Val His Cys Ile Phe Ser Pro Gln Ile Glu Glu
            100                 105                 110

Pro Ser Gln Cys Pro Asp Cys Val Val Ser Ala Leu Gly Ala Lys Val
        115                 120                 125

Leu Ser Ser Val Lys Asp Arg Phe Ile Asn Phe Phe Val Gly Asn Thr
    130                 135                 140

Ile Asn Ser Ser Tyr Phe Pro Asp His Pro Leu His Ser Ile Ser Val
145                 150                 155                 160

Arg Arg Leu Lys Glu Thr Lys Asp Gly Phe Met Phe Leu Thr Asp Gln
                165                 170                 175

Ser Tyr Ile Asp Val Leu Pro Glu Phe Arg Asp Ser Tyr Pro Ile Lys
            180                 185                 190

Tyr Val His Ala Phe Glu Ser Asn Asn Phe Ile Tyr Phe Leu Thr Val
        195                 200                 205

Gln Arg Glu Thr Leu Asp Ala Gln Thr Phe His Thr Arg Ile Ile Arg
    210                 215                 220

Phe Cys Ser Ile Asn Ser Gly Leu His Ser Tyr Met Glu Met Pro Leu
225                 230                 235                 240

Glu Cys Ile Leu Thr Glu Lys Arg Lys Lys Arg Ser Thr Lys Lys Glu
                245                 250                 255

Val Phe Asn Ile Leu Gln Ala Ala Tyr Val Ser Lys Pro Gly Ala Gln
```

```
            260                 265                 270
Leu Ala Arg Gln Ile Gly Ala Ser Leu Asn Asp Asp Ile Leu Phe Gly
            275                 280                 285

Val Phe Ala Gln Ser Lys Pro Asp Ser Ala Glu Pro Met Asp Arg Ser
        290                 295                 300

Ala Met Cys Ala Phe Pro Ile Lys Tyr Val Asn Asp Phe Phe Asn Lys
305                 310                 315                 320

Ile Val Asn Lys Asn Asn Val Arg Cys Leu Gln His Phe Tyr Gly Pro
                325                 330                 335

Asn His Glu His Cys Phe Asn Arg Thr Leu Leu Arg Asn Ser Ser Gly
            340                 345                 350

Cys Glu Ala Arg Arg Asp Glu Tyr Arg Thr Glu Phe Thr Thr Ala Leu
        355                 360                 365

Gln Arg Val Asp Leu Phe Met Gly Gln Phe Ser Glu Val Leu Leu Thr
    370                 375                 380

Ser Ile Ser Thr Phe Ile Lys Gly Asp Leu Thr Ile Ala Asn Leu Gly
385                 390                 395                 400

Thr Ser Glu Gly Arg Phe Met Gln Val Val Val Ser Arg Ser Gly Pro
                405                 410                 415

Ser Thr Pro His Val Asn Phe Leu Leu Asp Ser His Pro Val Ser Pro
            420                 425                 430

Glu Val Ile Val Glu His Thr Leu Asn Gln Asn Gly
        435                 440

<210> SEQ ID NO 80
<211> LENGTH: 451
<212> TYPE: PRT
<213> ORGANISM: Artificial Sequence
<220> FEATURE:
<223> OTHER INFORMATION: Synthetic (PSI-IPT domain of c-Met)

<400> SEQUENCE: 80

Tyr Thr Leu Val Ile Thr Gly Lys Lys Ile Thr Lys Ile Pro Leu Asn
1               5                   10                  15

Gly Leu Gly Cys Arg His Phe Gln Ser Cys Ser Gln Cys Leu Ser Ala
            20                  25                  30

Pro Pro Phe Val Gln Cys Gly Trp Cys His Asp Lys Cys Val Arg Ser
        35                  40                  45

Glu Glu Cys Leu Ser Gly Thr Trp Thr Gln Gln Ile Cys Leu Pro Ala
    50                  55                  60

Ile Tyr Lys Val Phe Pro Asn Ser Ala Pro Leu Glu Gly Gly Thr Arg
65                  70                  75                  80

Leu Thr Ile Cys Gly Trp Asp Phe Gly Phe Arg Arg Asn Asn Lys Phe
                85                  90                  95

Asp Leu Lys Lys Thr Arg Val Leu Leu Gly Asn Glu Ser Cys Thr Leu
            100                 105                 110

Thr Leu Ser Glu Ser Thr Met Asn Thr Leu Lys Cys Thr Val Gly Pro
        115                 120                 125

Ala Met Asn Lys His Phe Asn Met Ser Ile Ile Ile Ser Asn Gly His
    130                 135                 140

Gly Thr Thr Gln Tyr Ser Thr Phe Ser Tyr Val Asp Pro Val Ile Thr
145                 150                 155                 160

Ser Ile Ser Pro Lys Tyr Gly Pro Met Ala Gly Gly Thr Leu Leu Thr
                165                 170                 175

Leu Thr Gly Asn Tyr Leu Asn Ser Gly Asn Ser Arg His Ile Ser Ile
```

```
                    180                 185                 190
Gly Gly Lys Thr Cys Thr Leu Lys Ser Val Ser Asn Ser Ile Leu Glu
            195                 200                 205

Cys Tyr Thr Pro Ala Gln Thr Ile Ser Thr Glu Phe Ala Val Lys Leu
        210                 215                 220

Lys Ile Asp Leu Ala Asn Arg Glu Thr Ser Ile Phe Ser Tyr Arg Glu
225                 230                 235                 240

Asp Pro Ile Val Tyr Glu Ile His Pro Thr Lys Ser Phe Ile Ser Thr
                245                 250                 255

Trp Trp Lys Glu Pro Leu Asn Ile Val Ser Phe Leu Phe Cys Phe Ala
            260                 265                 270

Ser Gly Gly Ser Thr Ile Thr Gly Val Gly Lys Asn Leu Asn Ser Val
        275                 280                 285

Ser Val Pro Arg Met Val Ile Asn Val His Glu Ala Gly Arg Asn Phe
        290                 295                 300

Thr Val Ala Cys Gln His Arg Ser Asn Ser Glu Ile Ile Cys Cys Thr
305                 310                 315                 320

Thr Pro Ser Leu Gln Gln Leu Asn Leu Gln Leu Pro Leu Lys Thr Lys
                325                 330                 335

Ala Phe Phe Met Leu Asp Gly Ile Leu Ser Lys Tyr Phe Asp Leu Ile
            340                 345                 350

Tyr Val His Asn Pro Val Phe Lys Pro Phe Glu Lys Pro Val Met Ile
        355                 360                 365

Ser Met Gly Asn Glu Asn Val Leu Glu Ile Lys Gly Asn Asp Ile Asp
        370                 375                 380

Pro Glu Ala Val Lys Gly Glu Val Leu Lys Val Gly Asn Lys Ser Cys
385                 390                 395                 400

Glu Asn Ile His Leu His Ser Glu Ala Val Leu Cys Thr Val Pro Asn
                405                 410                 415

Asp Leu Leu Lys Leu Asn Ser Glu Leu Asn Ile Glu Trp Lys Gln Ala
            420                 425                 430

Ile Ser Ser Thr Val Leu Gly Lys Val Ile Val Gln Pro Asp Gln Asn
        435                 440                 445

Phe Thr Gly
    450

<210> SEQ ID NO 81
<211> LENGTH: 313
<212> TYPE: PRT
<213> ORGANISM: Artificial Sequence
<220> FEATURE:
<223> OTHER INFORMATION: Synthetic (TyrKc domain of c-Met)

<400> SEQUENCE: 81

Val His Phe Asn Glu Val Ile Gly Arg Gly His Phe Gly Cys Val Tyr
1               5                   10                  15

His Gly Thr Leu Leu Asp Asn Asp Gly Lys Lys Ile His Cys Ala Val
            20                  25                  30

Lys Ser Leu Asn Arg Ile Thr Asp Ile Gly Glu Val Ser Gln Phe Leu
        35                  40                  45

Thr Glu Gly Ile Ile Met Lys Asp Phe Ser His Pro Asn Val Leu Ser
    50                  55                  60

Leu Leu Gly Ile Cys Leu Arg Ser Glu Gly Ser Pro Leu Val Val Leu
65                  70                  75                  80

Pro Tyr Met Lys His Gly Asp Leu Arg Asn Phe Ile Arg Asn Glu Thr
```

```
              85                  90                  95
His Asn Pro Thr Val Lys Asp Leu Ile Gly Phe Gly Leu Gln Val Ala
            100                 105                 110
Lys Gly Met Lys Tyr Leu Ala Ser Lys Lys Phe Val His Arg Asp Leu
            115                 120                 125
Ala Ala Arg Asn Cys Met Leu Asp Glu Lys Phe Thr Val Lys Val Ala
            130                 135                 140
Asp Phe Gly Leu Ala Arg Asp Met Tyr Asp Lys Glu Tyr Tyr Ser Val
145                 150                 155                 160
His Asn Lys Thr Gly Ala Lys Leu Pro Val Lys Trp Met Ala Leu Glu
            165                 170                 175
Ser Leu Gln Thr Gln Lys Phe Thr Thr Lys Ser Asp Val Trp Ser Phe
            180                 185                 190
Gly Val Leu Leu Trp Glu Leu Met Thr Arg Gly Ala Pro Pro Tyr Pro
            195                 200                 205
Asp Val Asn Thr Phe Asp Ile Thr Val Tyr Leu Leu Gln Gly Arg Arg
            210                 215                 220
Leu Leu Gln Pro Glu Tyr Cys Pro Asp Pro Leu Tyr Glu Val Met Leu
225                 230                 235                 240
Lys Cys Trp His Pro Lys Ala Glu Met Arg Pro Ser Phe Ser Glu Leu
            245                 250                 255
Val Ser Arg Ile Ser Ala Ile Phe Ser Thr Phe Ile Gly Glu His Tyr
            260                 265                 270
Val His Val Asn Ala Thr Tyr Val Asn Val Lys Cys Val Ala Pro Tyr
            275                 280                 285
Pro Ser Leu Leu Ser Ser Glu Asp Asn Ala Asp Asp Glu Val Asp Thr
            290                 295                 300
Arg Pro Ala Ser Phe Trp Glu Thr Ser
305                 310

<210> SEQ ID NO 82
<211> LENGTH: 1332
<212> TYPE: DNA
<213> ORGANISM: Artificial Sequence
<220> FEATURE:
<223> OTHER INFORMATION: Synthetic (polynucleotide encoding SEMA domain
      of c-Met)

<400> SEQUENCE: 82
ctacatgagc atcacatttt ccttggtgcc actaactaca tttatgtttt aaatgaggaa      60
gaccttcaga aggttgctga gtacaagact gggcctgtgc tggaacaccc agattgtttc    120
ccatgtcagg actgcagcag caaagccaat ttatcaggag gtgtttggaa agataacatc    180
aacatggctc tagttgtcga cacctactat gatgatcaac tcattagctg tggcagcgtc    240
aacagaggga cctgccagcg acatgtcttt ccccacaatc atactgctga catacagtcg    300
gaggttcact gcatattctc cccacagata gaagagccca gccagtgtcc tgactgtgtg    360
gtgagcgccc tgggagccaa gtcctttca tctgtaaagg accggttcat caacttcttt    420
gtaggcaata ccataaattc ttcttatttc ccagatcatc cattgcattc gatatcagtg    480
agaaggctaa aggaaacgaa agatggtttt atgttttga cggaccagtc ctacattgat    540
gttttacctg agttcagaga ttcttacccc attaagtatg tccatgcctt tgaaagcaac    600
aattttattt acttccttgac ggtccaaagg gaaactctag atgctcagac ttttcacaca    660
agaataatca ggttctgttc cataaactct ggattgcatt cctacatgga aatgcctctg    720
```

```
gagtgtattc tcacagaaaa gagaaaaaag agatccacaa agaaggaagt gtttaatata    780
cttcaggctg cgtatgtcag caagcctggg gcccagcttg ctagacaaat aggagccagc    840
ctgaatgatg acattctttt cggggtgttc gcacaaagca agccagattc tgccgaacca    900
atggatcgat ctgccatgtg tgcattccct atcaaatatg tcaacgactt cttcaacaag    960
atcgtcaaca aaaacaatgt gagatgtctc cagcattttt acggacccaa tcatgagcac   1020
tgctttaata ggacacttct gagaaattca tcaggctgtg aagcgcgccg tgatgaatat   1080
cgaacagagt ttaccacagc tttgcagcgc gttgacttat tcatgggtca attcagcgaa   1140
gtcctcttaa catctatatc caccttcatt aaaggagacc tcaccatagc taatcttggg   1200
acatcagagg gtcgcttcat gcaggttgtg gtttctcgat caggaccatc aaccccctcat  1260 gtgaattttc tcctggactc ccatccagtg tctccagaag tgattgtgga gcatacatta   1320
aaccaaaatg gc                                                        1332

<210> SEQ ID NO 83
<211> LENGTH: 1299
<212> TYPE: DNA
<213> ORGANISM: Artificial Sequence
<220> FEATURE:
<223> OTHER INFORMATION: Synthetic (polynucleotide encoding PSI-IPT
      domain of c-Met)

<400> SEQUENCE: 83
tacacactgg ttatcactgg gaagaagatc acgaagatcc cattgaatgg cttgggctgc     60
agacatttcc agtcctgcag tcaatgcctc tctgccccac cctttgttca gtgtggctgg    120
tgccacgaca aatgtgtgcg atcggaggaa tgcctgagcg ggacatggac tcaacagatc    180
tgtctgcctg caatctacaa ggttttccca aatagtgcac cccttgaagg agggacaagg    240
ctgaccatat gtggctggga cttttggattt cggaggaata taaatttga tttaaagaaa    300 actagagttc tccttggaaa tgagagctgc acccttgactt taagtgagag cacgatgaat    360
acattgaaat gcacagttgg tcctgccatg aataagcatt tcaatatgtc cataattatt    420
tcaaatggcc acgggacaac acaatacagt acattctcct atgtggatcc tgtaataaca    480
agtatttcgc cgaaatacgg tcctatggct ggtggcactt tacttacttt aactggaaat    540
tacctaaaca gtgggaattc tagacacatt tcaattggtg aaaaacatg tactttaaaa    600 agtgtgtcaa acagtattct tgaatgttat acccccagcc aaaccatttc aactgagttt    660
gctgttaaat tgaaaattga cttagccaac cgagagacaa gcatcttcag ttaccgtgaa    720
gatcccattg tctatgaaat tcatccaacc aaatctttta ttagtggtgg gagcacaata    780
acaggtgttg ggaaaaacct gaattcagtt agtgtcccga gaatggtcat aaatgtgcat    840
gaagcaggaa ggaactttac agtggcatgt caacatcgct ctaattcaga gataatctgt    900
tgtaccactc cttccctgca cagctgaat ctgcaactcc cctgaaaac caaagccttt    960 ttcatgttag atgggatcct ttccaaatac tttgatctca tttatgtaca taatcctgtg   1020
tttaagcctt tgaaaagcc agtgatgatc tcaatgggca atgaaaatgt actggaaatt   1080
aagggaaatg atattgaccc tgaagcagtt aaaggtgaag tgttaaaagt tggaaataag   1140
agctgtgaga atatacactt acattctgaa gccgtttat gcacggtccc caatgacctg   1200
ctgaaattga acagcgagct aaatatagag tggaagcaag caatttcttc aaccgtcctt   1260
ggaaaagtaa tagttcaacc agatcagaat ttcacagga                          1299

<210> SEQ ID NO 84
```

```
<211> LENGTH: 939
<212> TYPE: DNA
<213> ORGANISM: Artificial Sequence
<220> FEATURE:
<223> OTHER INFORMATION: Synthetic (polynucleotide encoding TyrKc domain
      of c-Met)

<400> SEQUENCE: 84
gtgcatttca atgaagtcat aggaagaggg cattttggtt gtgtatatca tgggactttg      60
ttggacaatg atggcaagaa aattcactgt gctgtgaaat ccttgaacag aatcactgac     120
ataggagaag tttcccaatt tctgaccgag ggaatcatca tgaaagattt tagtcatccc     180
aatgtcctct cgctcctggg aatctgcctg cgaagtgaag gtctccgct ggtggtccta      240
ccatacatga acatggaga tcttcgaaat tcattcgaa atgagactca taatccaact       300
gtaaaagatc ttattggctt tggtcttcaa gtagccaaag gcatgaaata tcttgcaagc     360
aaaaagtttg tccacagaga cttggctgca agaaactgta tgctggatga aaaattcaca     420
gtcaaggttg ctgattttgg tcttgccaga gacatgtatg ataaagaata ctatagtgta     480
cacaacaaaa caggtgcaaa gctgccagtg aagtggatgg ctttggaaag tctgcaaact     540
caaaagttta ccaccaagtc agatgtgtgg tcctttggcg tgctcctctg ggagctgatg     600
acaagaggag ccccaccta tcctgacgta aacacctttg atataactgt ttacttgttg     660
caagggagaa gactcctaca acccgaatac tgcccagacc ccttatatga agtaatgcta     720
aaatgctggc accctaaagc cgaaatgcgc ccatcctttt ctgaactggt gtcccggata     780
tcagcgatct tctctacttt cattggggag cactatgtcc atgtgaacgc tacttatgtg     840
aacgtaaaat gtgtcgctcc gtatccttct ctgttgtcat cagaagataa cgctgatgat     900
gaggtggaca cacgaccagc ctccttctgg gagacatca                            939

<210> SEQ ID NO 85
<211> LENGTH: 13
<212> TYPE: PRT
<213> ORGANISM: Artificial Sequence
<220> FEATURE:
<223> OTHER INFORMATION: Synthetic (heavy chain CDR3 of anti-c-Met
      antibody)

<400> SEQUENCE: 85

Asp Asn Trp Phe Ala Tyr Trp Gly Gln Gly Thr Leu Val
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthetic (light chain CDR3 of anti-c-Met
      antibody)

<400> SEQUENCE: 86

Leu Thr Phe Gly Ala Gly Thr Lys Leu Glu
1               5                   10

<210> SEQ ID NO 87
<211> LENGTH: 117
<212> TYPE: PRT
<213> ORGANISM: Artificial Sequence
<220> FEATURE:
<223> OTHER INFORMATION: Synthetic (heavy chain variable region of
      monoclonal antibody AbF46)

<400> SEQUENCE: 87
```

```
Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
                20                  25                  30

Tyr Met Ser Trp Val Arg Gln Pro Pro Gly Lys Ala Leu Glu Trp Leu
            35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Gln Ser Ile
65                  70                  75                  80

Leu Tyr Leu Gln Met Asp Thr Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ala
        115
```

```
<210> SEQ ID NO 88
<211> LENGTH: 114
<212> TYPE: PRT
<213> ORGANISM: Artificial Sequence
<220> FEATURE:
<223> OTHER INFORMATION: Synthetic (light chain variable region of
      anti-c-Met antibody)

<400> SEQUENCE: 88
```

```
Asp Ile Leu Met Thr Gln Ser Pro Ser Ser Leu Thr Val Ser Ala Gly
1               5                   10                  15

Glu Lys Val Thr Met Ser Cys Lys Ser Ser Gln Ser Leu Leu Ala Ser
                20                  25                  30

Gly Asn Gln Asn Asn Tyr Leu Ala Trp His Gln Gln Lys Pro Gly Arg
            35                  40                  45

Ser Pro Lys Met Leu Ile Ile Trp Ala Ser Thr Arg Val Ser Gly Val
        50                  55                  60

Pro Asp Arg Phe Ile Gly Ser Gly Ser Gly Thr Asp Phe Thr Leu Thr
65                  70                  75                  80

Ile Asn Ser Val Gln Ala Glu Asp Leu Ala Val Tyr Tyr Cys Gln Gln
                85                  90                  95

Ser Tyr Ser Ala Pro Leu Thr Phe Gly Ala Gly Thr Lys Leu Glu Leu
            100                 105                 110

Lys Arg
```

```
<210> SEQ ID NO 89
<211> LENGTH: 17
<212> TYPE: PRT
<213> ORGANISM: Artificial Sequence
<220> FEATURE:
<223> OTHER INFORMATION: Synthetic (light chain CDR3 of anti-c-Met
      antibody)

<400> SEQUENCE: 89
```

```
Gln Gln Ser Tyr Ser Ala Pro Leu Thr Phe Gly Ala Gly Thr Lys Leu
1               5                   10                  15

Glu
```

```
<210> SEQ ID NO 90
<211> LENGTH: 117
<212> TYPE: PRT
```

<213> ORGANISM: Artificial Sequence
<220> FEATURE:
<223> OTHER INFORMATION: Synthetic (heavy chain variable region of AT-VH1)

<400> SEQUENCE: 90

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 91
<211> LENGTH: 117
<212> TYPE: PRT
<213> ORGANISM: Artificial Sequence
<220> FEATURE:
<223> OTHER INFORMATION: Synthetic (heavy chain variable region of AT-VH2)

<400> SEQUENCE: 91

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 92
<211> LENGTH: 117
<212> TYPE: PRT
<213> ORGANISM: Artificial Sequence
<220> FEATURE:
<223> OTHER INFORMATION: Synthetic (heavy chain variable region of AT-VH3)

<400> SEQUENCE: 92

Glu Val Gln Leu Val Glu Ser Gly Gly Gly Leu Val Gln Pro Gly Gly
1               5                   10                  15

```
Ser Leu Arg Leu Ser Cys Ala Thr Ser Gly Phe Thr Phe Thr Asp Tyr
            20                  25                  30

Tyr Met Ser Trp Val Arg Gln Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gly Thr Leu
            100                 105                 110

Val Thr Val Ser Ser
        115

<210> SEQ ID NO 93
<211> LENGTH: 117
<212> TYPE: PRT
<213> ORGANISM: Artificial Sequence
<220> FEATURE:
<223> OTHER INFORMATION: Synthetic (heavy chain variable region of
      AT-VH4)

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 94
<211> LENGTH: 117
<212> TYPE: PRT
<213> ORGANISM: Artificial Sequence
<220> FEATURE:
<223> OTHER INFORMATION: Synthetic (heavy chain variable region of
      AT-VH5)

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60
```

```
Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 95
<211> LENGTH: 114
<212> TYPE: PRT
<213> ORGANISM: Artificial Sequence
<220> FEATURE:
<223> OTHER INFORMATION: Synthetic (light chain variable region of
      anti c-Met humanized antibody(huAbF46-H4))

<400> SEQUENCE: 95

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Ala Pro Leu Thr Phe Gly Gln Gly Thr Lys Val Glu Ile
            100                 105                 110

Lys Arg

<210> SEQ ID NO 96
<211> LENGTH: 113
<212> TYPE: PRT
<213> ORGANISM: Artificial Sequence
<220> FEATURE:
<223> OTHER INFORMATION: Synthetic (light chain variable region of
      AT-Vk1)

<400> SEQUENCE: 96

Asp Ile Leu Met Thr Gln Ser Pro Ser Ser Leu Thr Ala Ser Val Gly
 1               5                  10                  15

Asp Arg Val Thr Met Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gln Gly Thr Lys Leu Glu Ile
            100                 105                 110
```

Lys

<210> SEQ ID NO 97
<211> LENGTH: 113
<212> TYPE: PRT
<213> ORGANISM: Artificial Sequence
<220> FEATURE:
<223> OTHER INFORMATION: Synthetic (light chain variable region of AT-Vk2)

<400> SEQUENCE: 97

Asp Ile Leu Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 98
<211> LENGTH: 113
<212> TYPE: PRT
<213> ORGANISM: Artificial Sequence
<220> FEATURE:
<223> OTHER INFORMATION: Synthetic (light chain variable region of AT-Vk3)

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 99
<211> LENGTH: 113
<212> TYPE: PRT
<213> ORGANISM: Artificial Sequence
<220> FEATURE:
<223> OTHER INFORMATION: Synthetic (light chain variable region of AT-Vk4)

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 100
<211> LENGTH: 13
<212> TYPE: PRT
<213> ORGANISM: Artificial Sequence
<220> FEATURE:
<223> OTHER INFORMATION: Synthetic (modified hinge region(U7-HC6))

<400> SEQUENCE: 100

Glu Pro Ser Cys Asp Lys His Cys Cys Pro Pro Cys Pro
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Synthetic (modified hinge region(U6-HC7))

<400> SEQUENCE: 101

Glu Pro Lys Ser Cys Asp Cys His Cys Pro Pro Cys Pro
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Synthetic (modified hinge region(U3-HC9))

<400> SEQUENCE: 102

Glu Arg Lys Cys Cys Val Glu Cys Pro Pro Cys Pro
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Synthetic (modified hinge region(U6-HC8))

<400> SEQUENCE: 103

Glu Pro Arg Asp Cys Gly Cys Lys Pro Cys Pro Pro Cys Pro
1               5                   10

<210> SEQ ID NO 104

```
<211> LENGTH: 13
<212> TYPE: PRT
<213> ORGANISM: Artificial Sequence
<220> FEATURE:
<223> OTHER INFORMATION: Synthetic (modified hinge region(U8-HC5))

<400> SEQUENCE: 104

Glu Lys Cys Asp Lys Thr His Thr Cys Pro Pro Cys Pro
1               5                   10

<210> SEQ ID NO 105
<211> LENGTH: 15
<212> TYPE: PRT
<213> ORGANISM: Artificial Sequence
<220> FEATURE:
<223> OTHER INFORMATION: Synthetic (human hinge region)

<400> SEQUENCE: 105

Glu Pro Lys Ser Cys Asp Lys Thr His Thr Cys Pro Pro Cys Pro
1               5                   10                  15

<210> SEQ ID NO 106
<211> LENGTH: 17
<212> TYPE: PRT
<213> ORGANISM: Artificial Sequence
<220> FEATURE:
<223> OTHER INFORMATION: Synthetic (CDR-L1 of antibody L3-11Y)

<400> SEQUENCE: 106

Lys Ser Ser Gln Ser Leu Leu Ala Trp Gly Asn Gln Asn Asn Tyr Leu
1               5                   10                  15

Ala

<210> SEQ ID NO 107
<211> LENGTH: 114
<212> TYPE: PRT
<213> ORGANISM: Artificial Sequence
<220> FEATURE:
<223> OTHER INFORMATION: Synthetic (amino acid sequence of light chain
      variable region of antibody L3-11Y)

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Trp
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg

<210> SEQ ID NO 108
<211> LENGTH: 220
<212> TYPE: PRT
<213> ORGANISM: Artificial Sequence
<220> FEATURE:
```

<223> OTHER INFORMATION: Synthetic (amino acid sequence of light chain
      of antibody L3-11Y)

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Trp
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 109
<211> LENGTH: 153
<212> TYPE: PRT
<213> ORGANISM: Artificial Sequence
<220> FEATURE:
<223> OTHER INFORMATION: Synthetic (anti-EGFR DARPin-01)

<400> SEQUENCE: 109

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Asp Asp
            20                  25                  30

Thr Trp Gly Trp Thr Pro Leu His Leu Ala Ala Tyr Gln Gly His Leu
        35                  40                  45

Glu Ile Val Glu Val Leu Leu Lys Asn Gly Ala Asp Val Asn Ala Tyr
    50                  55                  60

Asp Tyr Ile Gly Trp Thr Pro Leu His Leu Ala Ala Asp Gly His Leu
65                  70                  75                  80

Glu Ile Val Glu Val Leu Leu Lys Asn Gly Ala Asp Val Asn Ala Ser
                85                  90                  95

Asp Tyr Ile Gly Asp Thr Pro Leu His Leu Ala Ala His Asn Gly His
            100                 105                 110

Leu Glu Ile Val Glu Val Leu Leu Lys His Gly Ala Asp Val Asn Ala

```
                 115                 120                 125

Gln Asp Lys Phe Gly Lys Thr Ala Phe Asp Ile Ser Ile Asp Asn Gly
    130                 135                 140

Asn Glu Asp Leu Ala Glu Ile Leu Gln
145                 150

<210> SEQ ID NO 110
<211> LENGTH: 154
<212> TYPE: PRT
<213> ORGANISM: Artificial Sequence
<220> FEATURE:
<223> OTHER INFORMATION: Synthetic (Anti-EGFR DARPin-67)

<400> SEQUENCE: 110

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Thr Asp
                20                  25                  30

Asn Asp Gly Asn Thr Pro Leu His Leu Ser Ala Trp Ile Gly His Leu
            35                  40                  45

Glu Ile Val Glu Val Leu Leu Lys His Gly Ala Asp Val Asn Ala Asp
    50                  55                  60

Asp Leu Leu Gly Met Thr Pro Leu His Leu Ala Ala Asp Thr Gly His
65                  70                  75                  80

Leu Glu Ile Val Glu Val Leu Leu Lys Tyr Gly Ala Asp Val Asn Ala
                85                  90                  95

Arg Asp Thr Arg Gly Lys Thr Pro Leu His Leu Ala Ala Arg Asp Gly
            100                 105                 110

His Leu Glu Ile Val Glu Val Leu Leu Lys His Asp Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 111
<211> LENGTH: 154
<212> TYPE: PRT
<213> ORGANISM: Artificial Sequence
<220> FEATURE:
<223> OTHER INFORMATION: Synthetic (Anti-EGFR DARPin-68)

<400> SEQUENCE: 111

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Phe Asp
                20                  25                  30

Tyr Trp Gly Met Thr Pro Leu His Leu Ala Ala Asp Asn Gly His Leu
            35                  40                  45

Glu Ile Val Glu Val Leu Leu Lys His Gly Ala Asp Val Asn Ala Ser
    50                  55                  60

Asp Asn Phe Gly Phe Thr Pro Leu His Leu Ala Ala Phe Tyr Gly His
65                  70                  75                  80

Leu Glu Ile Val Glu Val Leu Leu Lys His Gly Ala Asp Val Asn Ala
                85                  90                  95

Phe Asp Met Trp Gly Asn Thr Pro Leu His Leu Ala Ala Gln Asn Gly
            100                 105                 110
```

His Leu Glu Ile Val Glu Val Leu Lys Asn Gly Ala Asp Val Asn
            115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 112
<211> LENGTH: 187
<212> TYPE: PRT
<213> ORGANISM: Artificial Sequence
<220> FEATURE:
<223> OTHER INFORMATION: Synthetic (Anti-EGFR DARPin-69)

<400> SEQUENCE: 112

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Asp Asp
            20                  25                  30

Asn Ala Gly Arg Thr Pro Leu His Leu Ala Ala Asn Phe Gly His Leu
        35                  40                  45

Glu Ile Val Glu Val Leu Leu Lys Asn Gly Ala Asp Val Asn Ala Lys
    50                  55                  60

Gly His His Cys Asn Thr Pro Leu His Leu Ala Ala Trp Ala Gly His
65                  70                  75                  80

Leu Glu Ile Val Glu Val Leu Leu Lys Tyr Gly Ala Asp Val Asn Ala
                85                  90                  95

Asp Asp Asp Glu Gly Tyr Thr Pro Leu His Leu Ala Ala Asp Ile Gly
            100                 105                 110

Asp Leu Glu Ile Val Glu Val Leu Leu Lys Tyr Gly Ala Asp Val Asn
        115                 120                 125

Ala Trp Asp Met Tyr Gly Arg Thr Pro Leu His Leu Ala Ala Ser Ala
    130                 135                 140

Gly His Leu Glu Ile Val Glu Val Leu Leu Lys Tyr Gly Ala Asp Val
145                 150                 155                 160

Asn Ala Gln Asp Lys Phe Gly Lys Thr Ala Phe Asp Ile Ser Ile Asp
                165                 170                 175

Asn Gly Asn Glu Asp Leu Ala Glu Ile Leu Gln
            180                 185

<210> SEQ ID NO 113
<211> LENGTH: 120
<212> TYPE: PRT
<213> ORGANISM: Artificial Sequence
<220> FEATURE:
<223> OTHER INFORMATION: Synthetic (heavy chain variable region of
      anti-HER2 antibody)

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr

```
                65                  70                  75                  80
Leu Gln Met Asn Ser Leu Arg Ala Glu Asp Thr Ala Val Tyr Tyr Cys
                    85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 114
<211> LENGTH: 108
<212> TYPE: PRT
<213> ORGANISM: Artificial Sequence
<220> FEATURE:
<223> OTHER INFORMATION: Synthetic (light chain variable region of
      anti-HER2 antibody)

<400> SEQUENCE: 114

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg
            100                 105

<210> SEQ ID NO 115
<211> LENGTH: 121
<212> TYPE: PRT
<213> ORGANISM: Artificial Sequence
<220> FEATURE:
<223> OTHER INFORMATION: Synthetic (heavy chain variable region of
      anti-HER3 antibody)

<400> SEQUENCE: 115

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Ala Ser Thr
        115                 120
```

<210> SEQ ID NO 116
<211> LENGTH: 112
<212> TYPE: PRT
<213> ORGANISM: Artificial Sequence
<220> FEATURE:
<223> OTHER INFORMATION: Synthetic (light chain variable region of
      anti-HER3 antibody)

<400> SEQUENCE: 116

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Phe Val Ser Trp Tyr Gln Gln His Pro Gly Lys Ala Pro Lys Leu
            35                  40                  45

Met Ile Tyr Asp Val Ser Asp Arg Pro Ser Gly Val Ser Asp Arg Phe
        50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Val Thr Val Leu Gly
            100                 105                 110

<210> SEQ ID NO 117
<211> LENGTH: 121
<212> TYPE: PRT
<213> ORGANISM: Artificial Sequence
<220> FEATURE:
<223> OTHER INFORMATION: Synthetic (heavy chain variable region of
      anti-EGFR/HER3 antibody)

<400> SEQUENCE: 117

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Gly Asp
                20                  25                  30

Trp Ile His Trp Val Arg Gln Ala Pro Gly Lys Gly Leu Glu Trp Val
            35                  40                  45

Gly Glu Ile Ser Ala Ala Gly Gly Tyr Thr Asp Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ser Arg Val Ser Phe Glu Ala Ala Met Asp Tyr Trp Gly
            100                 105                 110

Gln Gly Thr Leu Val Thr Val Ser Ser
        115                 120

<210> SEQ ID NO 118
<211> LENGTH: 107
<212> TYPE: PRT
<213> ORGANISM: Artificial Sequence
<220> FEATURE:
<223> OTHER INFORMATION: Synthetic (light chain variable region of
      anti-HER3 antibody)

<400> SEQUENCE: 118

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Asn Ile Ala Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Glu Pro Pro Pro Tyr
                85                  90                  95

Thr Phe Gly Gln Gly Thr Lys Val Glu Ile Lys
            100                 105

<210> SEQ ID NO 119
<211> LENGTH: 114
<212> TYPE: PRT
<213> ORGANISM: Artificial Sequence
<220> FEATURE:
<223> OTHER INFORMATION: Synthetic (light chain variable region of
      anti c-Met antibody)

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg

<210> SEQ ID NO 120
<211> LENGTH: 153
<212> TYPE: PRT
<213> ORGANISM: Artificial Sequence
<220> FEATURE:
<223> OTHER INFORMATION: Synthetic (DARPin E_01)

<400> SEQUENCE: 120

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Asp Asp
            20                  25                  30

Thr Trp Gly Trp Thr Pro Leu His Leu Ala Ala Tyr Gln Gly His Leu
        35                  40                  45

Glu Ile Val Glu Val Leu Leu Lys Asn Gly Ala Asp Val Asn Ala Tyr
    50                  55                  60

Asp Tyr Ile Gly Trp Thr Pro Leu His Leu Ala Ala Asp Gly His Leu
65                  70                  75                  80

Glu Ile Val Glu Val Leu Leu Lys Asn Gly Ala Asp Val Asn Ala Ser
```

-continued

```
                85                  90                  95
Asp Tyr Ile Gly Asp Thr Pro Leu His Leu Ala Ala His Asn Gly His
                100                 105                 110

Leu Glu Ile Val Glu Val Leu Leu Lys His Gly Ala Asp Val Asn Ala
            115                 120                 125

Gln Asp Lys Phe Gly Lys Thr Ala Phe Asp Ile Ser Ile Asp Asn Gly
        130                 135                 140

Asn Glu Asp Leu Ala Glu Ile Leu Gln
145                 150

<210> SEQ ID NO 121
<211> LENGTH: 154
<212> TYPE: PRT
<213> ORGANISM: Artificial Sequence
<220> FEATURE:
<223> OTHER INFORMATION: Synthetic (DARPin E_67)

<400> SEQUENCE: 121

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Thr Asp
            20                  25                  30

Asn Asp Gly Asn Thr Pro Leu His Leu Ser Ala Trp Ile Gly His Leu
        35                  40                  45

Glu Ile Val Glu Val Leu Leu Lys His Gly Ala Asp Val Asn Ala Asp
    50                  55                  60

Asp Leu Leu Gly Met Thr Pro Leu His Leu Ala Ala Asp Thr Gly His
65                  70                  75                  80

Leu Glu Ile Val Glu Val Leu Leu Lys Tyr Gly Ala Asp Val Asn Ala
                85                  90                  95

Arg Asp Thr Arg Gly Lys Thr Pro Leu His Leu Ala Ala Arg Asp Gly
                100                 105                 110

His Leu Glu Ile Val Glu Val Leu Leu Lys His Asp Ala Asp Val Asn
            115                 120                 125

Ala Gln Asp Lys Phe Gly Lys Thr Ala Phe Asp Ile Ser Ile Asp Asn
        130                 135                 140

Gly Asn Glu Asp Leu Ala Glu Ile Leu Gln
145                 150

<210> SEQ ID NO 122
<211> LENGTH: 154
<212> TYPE: PRT
<213> ORGANISM: Artificial Sequence
<220> FEATURE:
<223> OTHER INFORMATION: Synthetic (DARPin E_68)

<400> SEQUENCE: 122

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Phe Asp
            20                  25                  30

Tyr Trp Gly Met Thr Pro Leu His Leu Ala Ala Asp Asn Gly His Leu
        35                  40                  45

Glu Ile Val Glu Val Leu Leu Lys His Gly Ala Asp Val Asn Ala Ser
    50                  55                  60

Asp Asn Phe Gly Phe Thr Pro Leu His Leu Ala Ala Phe Tyr Gly His
65                  70                  75                  80
```

```
Leu Glu Ile Val Glu Val Leu Leu Lys His Gly Ala Asp Val Asn Ala
                85                  90                  95

Phe Asp Met Trp Gly Asn Thr Pro Leu His Leu Ala Ala Gln Asn Gly
            100                 105                 110

His Leu Glu Ile Val Glu Val Leu Leu Lys Asn Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 123
<211> LENGTH: 187
<212> TYPE: PRT
<213> ORGANISM: Artificial Sequence
<220> FEATURE:
<223> OTHER INFORMATION: Synthetic (DARPin E_69)

<400> SEQUENCE: 123

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Asp Asp
            20                  25                  30

Asn Ala Gly Arg Thr Pro Leu His Leu Ala Ala Asn Phe Gly His Leu
        35                  40                  45

Glu Ile Val Glu Val Leu Leu Lys Asn Gly Ala Asp Val Asn Ala Lys
    50                  55                  60

Gly His His Cys Asn Thr Pro Leu His Leu Ala Ala Trp Ala Gly His
65                  70                  75                  80

Leu Glu Ile Val Glu Val Leu Leu Lys Tyr Gly Ala Asp Val Asn Ala
                85                  90                  95

Asp Asp Asp Glu Gly Tyr Thr Pro Leu His Leu Ala Ala Asp Ile Gly
            100                 105                 110

Asp Leu Glu Ile Val Glu Val Leu Leu Lys Tyr Gly Ala Asp Val Asn
        115                 120                 125

Ala Trp Asp Met Tyr Gly Arg Thr Pro Leu His Leu Ala Ala Ser Ala
    130                 135                 140

Gly His Leu Glu Ile Val Glu Val Leu Leu Lys Tyr Gly Ala Asp Val
145                 150                 155                 160

Asn Ala Gln Asp Lys Phe Gly Lys Thr Ala Phe Asp Ile Ser Ile Asp
                165                 170                 175

Asn Gly Asn Glu Asp Leu Ala Glu Ile Leu Gln
            180                 185

<210> SEQ ID NO 124
<211> LENGTH: 154
<212> TYPE: PRT
<213> ORGANISM: Artificial Sequence
<220> FEATURE:
<223> OTHER INFORMATION: Synthetic (DARPin 9_16)

<400> SEQUENCE: 124

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala His Asp
            20                  25                  30

Phe His Gly Leu Thr Pro Leu His Leu Ala Ala Gly Met Gly His Leu
        35                  40                  45
```

```
Glu Ile Val Glu Val Leu Leu Lys Asn Gly Ala Asp Val Asn Ala Val
        50                  55                  60

Asp Thr Asp Gly Ile Thr Leu Leu His Leu Ala Ala Tyr Tyr Gly His
 65                  70                  75                  80

Leu Glu Ile Val Glu Val Leu Leu Lys His Gly Ala Asp Val Asn Ala
                85                  90                  95

His Asp Tyr Ala Gly Ser Thr Pro Leu His Leu Ala Ala Asn Thr Gly
            100                 105                 110

His Leu Glu Ile Val Glu Val Leu Leu Lys Asn Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 125
<211> LENGTH: 154
<212> TYPE: PRT
<213> ORGANISM: Artificial Sequence
<220> FEATURE:
<223> OTHER INFORMATION: Synthetic (DARPin 9_26)

<400> SEQUENCE: 125

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Lys Asp
            20                  25                  30

Phe Tyr Gly Ile Thr Pro Leu His Leu Ala Ala Tyr Gly His Leu
        35                  40                  45

Glu Ile Val Glu Val Leu Leu Lys His Gly Ala Asp Val Asn Ala His
        50                  55                  60

Asp Trp Asn Gly Trp Thr Pro Leu His Leu Ala Ala Lys Tyr Gly His
 65                  70                  75                  80

Leu Glu Ile Val Glu Val Leu Leu Lys His Gly Ala Asp Val Asn Ala
                85                  90                  95

Ile Asp Asn Ala Gly Lys Thr Pro Leu His Leu Ala Ala Ala His Gly
            100                 105                 110

His Leu Glu Ile Val Glu Val Leu Leu Lys Tyr Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 126
<211> LENGTH: 154
<212> TYPE: PRT
<213> ORGANISM: Artificial Sequence
<220> FEATURE:
<223> OTHER INFORMATION: Synthetic (DARPin 9_29)
<220> FEATURE:
<221> NAME/KEY: MOD_RES
<222> LOCATION: (67)
<223> OTHER INFORMATION: Xaa is Ala, Ile, Leu, Met, Phe, Pro, Trp,
      Val, Asn, Cys, Gln, Gly, Ser, Thr, Tyr, Asp, Glu, Arg, His or Lys

<400> SEQUENCE: 126

Asp Leu Gly Lys Lys Leu Leu Glu Ala Ala Arg Ala Gly Gln Asp Asp
1               5                   10                  15
```

Glu Val Arg Ile Leu Met Ala Asn Gly Ala Asp Val Asn Ala His Asp
            20                  25                  30

Phe Tyr Gly Ile Thr Pro Leu His Leu Ala Ala Asn Phe Gly His Leu
        35                  40                  45

Glu Ile Val Glu Val Leu Leu Lys His Gly Ala Asp Val Asn Ala Phe
 50                  55                  60

Asp Tyr Xaa Asp Asn Thr Pro Leu His Leu Ala Ala Asp Ala Gly His
 65                  70                  75                  80

Leu Glu Ile Val Glu Val Leu Leu Lys Tyr Gly Ala Asp Val Asn Ala
                85                  90                  95

Ser Asp Arg Asp Gly His Thr Pro Leu His Leu Ala Ala Arg Glu Gly
            100                 105                 110

His Leu Glu Ile Val Glu Val Leu Leu Lys Asn Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 127
<211> LENGTH: 154
<212> TYPE: PRT
<213> ORGANISM: Artificial Sequence
<220> FEATURE:
<223> OTHER INFORMATION: Synthetic (DARPin H_14)

<400> SEQUENCE: 127

Asp Leu Gly Lys Lys Leu Leu Glu Ala Ala Arg Ala Gly Gln Asp Asp
1               5                   10                  15

Glu Val Cys Ile Leu Met Ala Asn Gly Ala Asp Val Asn Ala Thr Asp
            20                  25                  30

Ile His Gly His Thr Pro Leu His Leu Ala Ala Ala Met Gly His Leu
        35                  40                  45

Glu Ile Val Glu Val Leu Leu Lys Asn Gly Ala Asp Val Asn Ala Asn
 50                  55                  60

Asp Trp Arg Gly Phe Thr Pro Leu His Leu Ala Ala Leu Asn Gly His
 65                  70                  75                  80

Leu Glu Ile Val Glu Val Leu Leu Lys Asn Gly Ala Asp Val Asn Ala
                85                  90                  95

Thr Asp Thr Ala Gly Asn Thr Pro Leu His Leu Ala Ala Trp Phe Gly
            100                 105                 110

His Leu Glu Ile Val Glu Val Leu Leu Lys Asn Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 128
<211> LENGTH: 187
<212> TYPE: PRT
<213> ORGANISM: Artificial Sequence
<220> FEATURE:
<223> OTHER INFORMATION: Synthetic (DARPin B4_01)

<400> SEQUENCE: 128

Asp Leu Gly Lys Lys Leu Leu Glu Ala Ala Arg Ala Gly Gln Asp Asp

```
  1               5                  10                 15
Glu Val His Ile Leu Met Ala Asn Gly Ala Asp Val Asn Ala Val Asp
                20                 25                 30

Trp Met Gly Asp Thr Pro Leu His Leu Ala Ala Phe Tyr Gly His Leu
                35                 40                 45

Glu Ile Val Glu Val Leu Leu Lys Asn Gly Ala Asp Val Asn Ala Lys
                50                 55                 60

Asp Thr Trp Gly Asp Thr Pro Leu His Leu Ala Ala Leu Leu Gly Arg
65                  70                 75                 80

Leu Glu Ile Val Glu Val Leu Leu Lys His Gly Ala Asp Val Asn Ala
                    85                 90                 95

Ile Asp Met Arg Gly Thr Thr Pro Leu His Leu Ala Ala Pro Ala Gly
                100                105                110

His Leu Glu Ile Val Glu Val Leu Leu Lys Tyr Gly Ala Asp Val Asn
                115                120                125

Ala Asp Asp Val His Gly Asn Thr Pro Leu His Leu Ala Ala Met Ser
130                 135                140

Gly His Leu Glu Ile Val Glu Val Leu Leu Lys Tyr Gly Ala Asp Val
145                 150                155                160

Asn Ala Gln Asp Lys Phe Gly Lys Thr Ala Phe Asp Ile Ser Ile Asp
                165                170                175

Asn Gly Asn Glu Asp Leu Ala Glu Ile Leu Gln
                180                185

<210> SEQ ID NO 129
<211> LENGTH: 154
<212> TYPE: PRT
<213> ORGANISM: Artificial Sequence
<220> FEATURE:
<223> OTHER INFORMATION: Synthetic (DARPin B4_02)

<400> SEQUENCE: 129

Asp Leu Gly Lys Lys Leu Leu Glu Ala Ala Arg Ala Gly Gln Asp Asp
1               5                  10                 15

Glu Val Arg Ile Leu Met Ala Asn Gly Ala Asp Val Asn Ala Lys Asp
                20                 25                 30

Asn Ala Gly Lys Thr Ala Leu His Leu Ala Ala Val Trp Gly His Leu
                35                 40                 45

Glu Ile Val Glu Val Leu Leu Lys Asn Gly Ala Asp Val Asn Ala Tyr
                50                 55                 60

Asp Ala Ser Gly Tyr Thr Leu Leu His Leu Ala Ala Arg Met Gly His
65                  70                 75                 80

Leu Glu Ile Val Glu Val Leu Leu Lys Tyr Gly Ala Asp Val Asn Ala
                    85                 90                 95

Arg Asp Arg Phe Gly Ser Thr Pro Leu His Leu Ala Ala Trp His Gly
                100                105                110

His Leu Glu Ile Val Glu Val Leu Leu Lys His Gly Ala Asp Val Asn
                115                120                125

Ala Gln Asp Lys Phe Gly Lys Thr Ala Phe Asp Ile Ser Ile Asp Asn
130                 135                140

Gly Asn Glu Asp Leu Ala Glu Ile Leu Gln
145                 150

<210> SEQ ID NO 130
<211> LENGTH: 154
<212> TYPE: PRT
```

<213> ORGANISM: Artificial Sequence
<220> FEATURE:
<223> OTHER INFORMATION: Synthetic (DARPin B4_07)

<400> SEQUENCE: 130

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Arg Asp
                20                  25                  30

Val Phe Gly Trp Thr Pro Leu His Leu Ala Ala Val Asp Gly His Leu
            35                  40                  45

Glu Ile Val Glu Val Leu Leu Lys Tyr Gly Ala Asp Val Asn Ala Arg
50                  55                  60

Asp Val Ala Gly Arg Thr Pro Leu His Leu Ala Ala Ser Phe Gly His
65                  70                  75                  80

Leu Glu Ile Val Glu Val Leu Leu Lys Tyr Gly Ala Asp Val Asn Ala
                85                  90                  95

Val Asp Tyr Thr Gly Thr Thr Pro Leu His Leu Ala Ala Trp His Gly
            100                 105                 110

His Leu Glu Ile Val Glu Val Leu Leu Lys His Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 131
<211> LENGTH: 154
<212> TYPE: PRT
<213> ORGANISM: Artificial Sequence
<220> FEATURE:
<223> OTHER INFORMATION: Synthetic (DARPin B4_33)

<400> SEQUENCE: 131

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Glu Asp
                20                  25                  30

Ala Thr Gly Phe Thr Pro Leu His Leu Ala Ala Val Trp Gly His Leu
            35                  40                  45

Glu Ile Val Glu Val Leu Leu Lys Asn Gly Ala Asp Val Asn Ala Asn
50                  55                  60

Asp Gln Tyr Gly Tyr Thr Pro Leu His Leu Ala Ala Arg Met Gly His
65                  70                  75                  80

Leu Glu Ile Val Glu Val Leu Leu Lys His Gly Ala Asp Val Asn Ala
                85                  90                  95

Ile Asp Val Leu Gly Thr Thr Pro Leu His Leu Ala Ala Trp His Gly
            100                 105                 110

His Leu Glu Ile Val Glu Val Leu Leu Lys Asn Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 132
<211> LENGTH: 154

```
<212> TYPE: PRT
<213> ORGANISM: Artificial Sequence
<220> FEATURE:
<223> OTHER INFORMATION: Synthetic (DARPin B4_45)

<400> SEQUENCE: 132

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Arg Asp
                20                  25                  30

Asp Gly Gly Thr Thr Pro Leu His Leu Ala Ala Asn His Gly His Leu
            35                  40                  45

Glu Ile Val Glu Val Leu Leu Lys Tyr Gly Ala Asp Val Asn Ala Asn
50                  55                  60

Asp Arg Tyr Gly Tyr Thr Thr Leu His Leu Ala Arg His Gly His
65                  70                  75                  80

Leu Glu Ile Val Glu Val Leu Leu Lys His Gly Ala Asp Val Asn Ala
                85                  90                  95

Phe Asp Asn Thr Gly Gln Thr Pro Leu His Leu Ala Ala Trp His Gly
                100                 105                 110

His Leu Glu Ile Val Glu Val Leu Leu Lys Tyr Gly Ala Asp Val Asn
            115                 120                 125

Ala Gln Asp Lys Phe Gly Lys Thr Ala Phe Asp Ile Ser Ile Asp Asn
130                 135                 140

Gly Asn Glu Asp Leu Ala Glu Ile Leu Gln
145                 150

<210> SEQ ID NO 133
<211> LENGTH: 187
<212> TYPE: PRT
<213> ORGANISM: Artificial Sequence
<220> FEATURE:
<223> OTHER INFORMATION: Synthetic (DARPin B4_50)

<400> SEQUENCE: 133

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala His Asp
                20                  25                  30

Arg Tyr Gly Val Thr Pro Leu His Leu Ala Ala Tyr Phe Gly His Leu
            35                  40                  45

Glu Ile Val Glu Val Leu Leu Lys Asn Gly Ala Asp Val Asn Ala Asp
50                  55                  60

Asp His Asp Gly Tyr Thr Pro Leu His Leu Ala Ala Asp Lys Gly His
65                  70                  75                  80

Leu Glu Ile Val Glu Val Leu Leu Lys His Gly Ala Asp Val Asn Ala
                85                  90                  95

Asp Asp Ser Met Gly Asn Thr Pro Leu His Leu Ala Ala Arg His Gly
                100                 105                 110

His Leu Glu Ile Val Glu Val Leu Leu Lys His Gly Ala Asp Val Asn
            115                 120                 125

Ala Asn Asp Phe Met Gly Ser Thr Pro Leu His Leu Ala Ala Trp Ser
130                 135                 140

Gly His Leu Glu Ile Val Glu Val Leu Leu Lys His Gly Ala Asp Val
145                 150                 155                 160

Asn Ala Gln Asp Lys Phe Gly Lys Thr Ala Phe Asp Ile Ser Ile Asp
                165                 170                 175
```

-continued

Asn Gly Asn Glu Asp Leu Ala Glu Ile Leu Gln
            180                 185

<210> SEQ ID NO 134
<211> LENGTH: 220
<212> TYPE: PRT
<213> ORGANISM: Artificial Sequence
<220> FEATURE:
<223> OTHER INFORMATION: Synthetic (DARPin B4_58)

<400> SEQUENCE: 134

Asp Leu Gly Lys Lys Leu Leu Glu Ala Thr Arg Ala Gly Gln Asp Asp
1               5                   10                  15

Glu Val Arg Ile Leu Met Ala Asn Gly Ala Asp Val Asn Ala Phe Asp
            20                  25                  30

Ser Asn Gly Ile Thr Pro Leu His Leu Ala Ala Phe Phe Gly His Leu
        35                  40                  45

Glu Ile Val Glu Val Leu Leu Lys Asn Gly Ala Asp Val Asn Ala His
    50                  55                  60

Asp Ser Tyr Gly Ser Thr Pro Leu His Leu Ala Asn Arg Gly His
65                  70                  75                  80

Leu Glu Ile Val Glu Val Leu Leu Lys Tyr Gly Ala Asp Val Asn Ala
                85                  90                  95

Phe Asp Ser Thr Gly Gln Thr Pro Leu His Leu Ala Ala Ser Gln Gly
            100                 105                 110

His Leu Glu Ile Val Glu Val Leu Leu Lys Tyr Gly Ala Asp Val Asn
        115                 120                 125

Ala Ser Asp Arg Met Gly Phe Thr Pro Leu His Leu Ala Ala Tyr Thr
    130                 135                 140

Gly His Leu Glu Ile Val Glu Val Leu Leu Lys Asn Gly Ala Asp Val
145                 150                 155                 160

Asn Ala Lys Asp Phe Val Gly Trp Thr Pro Leu His Leu Ala Ala Tyr
                165                 170                 175

Arg Gly His Leu Glu Ile Val Glu Val Leu Leu Lys His Gly Ala Asp
            180                 185                 190

Val Asn Ala Gln Asp Lys Phe Gly Lys Thr Ala Phe Asp Ile Ser Ile
        195                 200                 205

Asp Asn Gly Asn Glu Asp Leu Ala Glu Ile Leu Gln
    210                 215                 220

<210> SEQ ID NO 135
<211> LENGTH: 154
<212> TYPE: PRT
<213> ORGANISM: Artificial Sequence
<220> FEATURE:
<223> OTHER INFORMATION: Synthetic (DARPin I_01)

<400> SEQUENCE: 135

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Asn Asp
            20                  25                  30

Ile Ser Gly Tyr Thr Pro Leu His Leu Ala Ala Tyr Val Gly His Gln
        35                  40                  45

Glu Ile Val Glu Val Leu Leu Lys Asn Gly Ala Asp Val Asn Ala Asp
    50                  55                  60

Asp Thr Trp Gly Asp Thr Pro Leu His Leu Ala Ala Leu Phe Gly His

```
                65                  70                  75                  80
Leu Glu Ile Val Glu Val Leu Lys Tyr Gly Ala Asp Val Asn Ala
                    85                  90                  95

His Asp Arg Phe Gly Phe Thr Pro Leu His Leu Ala Ala Ser Ser Gly
                100                 105                 110

His Leu Glu Ile Val Glu Val Leu Lys His Gly Ala Asp Val Asn
                115                 120                 125

Ala Gln Asp Lys Phe Gly Lys Thr Ala Phe Asp Ile Ser Ile Asp Asn
130                 135                 140

Gly Asn Glu Asp Leu Ala Glu Ile Leu Gln
145                 150

<210> SEQ ID NO 136
<211> LENGTH: 121
<212> TYPE: PRT
<213> ORGANISM: Artificial Sequence
<220> FEATURE:
<223> OTHER INFORMATION: Synthetic (DARPin I_02)

<400> SEQUENCE: 136

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Arg Asp
                20                  25                  30

Met Ser Gly Tyr Thr Pro Leu His Leu Ala Ala His Met Gly His Leu
                35                  40                  45

Glu Ile Val Glu Val Leu Leu Lys Asn Gly Ala Asp Val Asn Ala Lys
50                  55                  60

Asp Asn Trp Gly Asp Thr Pro Leu His Leu Ala Ala Ile Phe Gly His
65                  70                  75                  80

Leu Glu Ile Val Glu Val Leu Leu Lys Asn Gly Ala Asp Val Asn Ala
                85                  90                  95

Gln Asp Lys Phe Gly Lys Thr Ala Phe Asp Ile Ser Ile Asp Asn Gly
                100                 105                 110

Asn Glu Asp Leu Ala Glu Ile Leu Gln
            115                 120

<210> SEQ ID NO 137
<211> LENGTH: 121
<212> TYPE: PRT
<213> ORGANISM: Artificial Sequence
<220> FEATURE:
<223> OTHER INFORMATION: Synthetic (DARPin I_07)

<400> SEQUENCE: 137

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Ser Asp
                20                  25                  30

Lys Ser Gly Tyr Thr Pro Leu His Leu Ala Ala His Ile Gly His Leu
                35                  40                  45

Glu Ile Val Glu Val Leu Leu Lys His Gly Ala Asp Val Asn Ala His
50                  55                  60

Asp Ser Trp Gly Asp Thr Pro Leu His Leu Ala Ala Thr Phe Gly His
65                  70                  75                  80

Leu Glu Ile Val Glu Val Leu Leu Lys His Gly Ala Asp Val Asn Ala
                85                  90                  95
```

```
Gln Asp Lys Phe Gly Lys Thr Ala Phe Asp Ile Ser Ile Asp Asn Gly
            100                 105                 110

Asn Glu Asp Leu Ala Glu Ile Leu Gln
        115                 120

<210> SEQ ID NO 138
<211> LENGTH: 154
<212> TYPE: PRT
<213> ORGANISM: Artificial Sequence
<220> FEATURE:
<223> OTHER INFORMATION: Synthetic (DARPin I_11)

<400> SEQUENCE: 138

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Ile Asp
            20                  25                  30

Thr Ile Gly Leu Thr Pro Leu His Leu Ala Ala His Asp Gly His Leu
        35                  40                  45

Glu Ile Val Glu Val Leu Leu Lys Asn Gly Ala Asp Val Asn Ala Ala
    50                  55                  60

Asp Asn Trp Gly Ile Thr Pro Leu His Leu Ala Arg Arg Gly His
65                  70                  75                  80

Leu Glu Ile Val Glu Val Leu Leu Lys His Gly Ala Asp Val Asn Ala
                85                  90                  95

Asp Asp Val Gln Gly Asn Thr Pro Leu His Leu Thr Ala His His Gly
            100                 105                 110

His Leu Glu Ile Val Glu Val Leu Leu Lys His Gly Ala Asp Val Asn
                115                 120                 125

Ala Gln Asp Lys Phe Gly Lys Thr Ala Phe Asp Ile Ser Ile Asp Asn
        130                 135                 140

Gly Asn Glu Asp Leu Ala Glu Ile Leu Gln
145                 150

<210> SEQ ID NO 139
<211> LENGTH: 121
<212> TYPE: PRT
<213> ORGANISM: Artificial Sequence
<220> FEATURE:
<223> OTHER INFORMATION: Synthetic (DARPin I_13)

<400> SEQUENCE: 139

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Phe Asp
            20                  25                  30

Met Ser Gly Tyr Thr Pro Leu His Leu Ala Ala Tyr Asp Gly His Leu
        35                  40                  45

Glu Ile Val Glu Val Leu Leu Lys Asn Gly Ala Asp Val Asn Ala Asn
    50                  55                  60

Asp Leu Trp Gly Asp Thr Pro Leu His Leu Ala Ala Thr Arg Gly His
65                  70                  75                  80

Leu Glu Ile Val Glu Val Leu Leu Lys Tyr Gly Ala Asp Val Asn Ala
                85                  90                  95

Gln Asp Lys Phe Gly Lys Thr Ala Phe Asp Ile Ser Ile Asp Asn Gly
            100                 105                 110

Asn Glu Asp Leu Ala Glu Ile Leu Gln
        115                 120
```

<210> SEQ ID NO 140
<211> LENGTH: 154
<212> TYPE: PRT
<213> ORGANISM: Artificial Sequence
<220> FEATURE:
<223> OTHER INFORMATION: Synthetic (DARPin I_19)

<400> SEQUENCE: 140

```
Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Asp Asp
            20                  25                  30

Asn Lys Gly Asp Thr Pro Leu His Leu Ala Ala Ser Phe Gly His Leu
        35                  40                  45

Glu Ile Val Glu Val Leu Leu Lys Asn Gly Ala Asp Val Asn Ala Asp
    50                  55                  60

Asp Tyr Phe Gly Asp Thr Pro Leu His Leu Ala Ala Trp Ser Gly His
65                  70                  75                  80

Leu Glu Ile Val Glu Val Leu Leu Lys Tyr Gly Ala Asp Val Asn Ala
                85                  90                  95

Gln Asp Gln Arg Gly Phe Thr Pro Leu His Leu Ala Ala Ile Ala Gly
            100                 105                 110

His Leu Glu Ile Val Glu Val Leu Leu Lys Tyr Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150
```

<210> SEQ ID NO 141
<211> LENGTH: 154
<212> TYPE: PRT
<213> ORGANISM: Artificial Sequence
<220> FEATURE:
<223> OTHER INFORMATION: Synthetic (DARPin T_01)

<400> SEQUENCE: 141

```
Asp Leu Gly Lys Lys Leu Leu Glu Ala Ala Arg Ala Asp Gln Asp Asp
1               5                   10                  15

Glu Val Arg Ile Leu Met Ala Asn Gly Ala Asp Val Asn Ala Asn Asp
            20                  25                  30

Ile Trp Gly Ile Thr Pro Leu His Leu Ala Ala Ile Phe Gly His Leu
        35                  40                  45

Glu Ile Val Glu Phe Leu Leu Lys Asn Gly Ala Asp Val Asn Ala Ser
    50                  55                  60

Asp Phe Ser Gly Phe Thr Pro Leu His Leu Ala Ala Tyr Lys Gly His
65                  70                  75                  80

Leu Glu Ile Val Glu Val Leu Leu Lys His Gly Ala Asp Val Asn Ala
                85                  90                  95

Asn Asp Ala Thr Gly Thr Thr Pro Leu His Leu Ala Ala Lys Lys Gly
            100                 105                 110

His Leu Glu Ile Val Glu Val Leu Leu Lys Asn Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
```

<210> SEQ ID NO 142
<211> LENGTH: 154
<212> TYPE: PRT
<213> ORGANISM: Artificial Sequence
<220> FEATURE:
<223> OTHER INFORMATION: Synthetic (DARPin T_02)

<400> SEQUENCE: 142

```
Asp Leu Gly Lys Lys Leu Leu Glu Val Ala Arg Ala Gly Gln Asp Asp
1               5                   10                  15

Glu Val Arg Ile Leu Met Ala Asn Gly Ala Asp Val Asn Ala Ala Asp
            20                  25                  30

His Gln Ser Phe Thr Pro Leu His Leu Tyr Ala Ile Phe Gly His Leu
        35                  40                  45

Glu Ile Val Glu Val Leu Leu Lys Asn Gly Ala Asp Val Asn Ala Ser
    50                  55                  60

Asp Trp His Gly Asn Thr Pro Leu His Leu Ala Ala Trp Ile Gly His
65                  70                  75                  80

Leu Glu Ile Val Glu Val Leu Leu Lys Tyr Gly Ala Asp Val Asn Ala
                85                  90                  95

Thr Asp His Ser Gly Ser Thr Pro Leu His Leu Ala Ala Thr Leu Gly
                100                 105                 110

His Leu Glu Ile Val Glu Val Leu Leu Lys Tyr Gly Ala Asp Val Asn
            115                 120                 125

Ala Gln Asp Lys Phe Gly Lys Thr Ala Phe Asp Ile Ser Ile Asp Asn
        130                 135                 140

Gly Asn Glu Asp Leu Ala Glu Ile Leu Gln
145                 150
```

<210> SEQ ID NO 143
<211> LENGTH: 154
<212> TYPE: PRT
<213> ORGANISM: Artificial Sequence
<220> FEATURE:
<223> OTHER INFORMATION: Synthetic (DARPin T_07)

<400> SEQUENCE: 143

```
Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Tyr Asp
            20                  25                  30

Trp Lys Gly Leu Thr Pro Leu His Leu Ala Ala Ile Phe Gly His Leu
        35                  40                  45

Glu Ile Val Glu Ser Ala Met Lys Asn Gly Ala Asp Val Asn Ala Ile
    50                  55                  60

Asp Phe Ser Gly Arg Thr Pro Leu His Leu Ala Ala Leu Ile Gly His
65                  70                  75                  80

Leu Glu Ile Val Glu Val Leu Leu Lys Tyr Gly Ala Asp Val Asn Ala
                85                  90                  95

His Asp Ser Ala Gly Ser Thr Pro Leu His Leu Ala Ala Thr Lys Gly
                100                 105                 110

His Leu Glu Ile Val Glu Val Leu Leu Lys Tyr Gly Ala Asp Val Asn
            115                 120                 125

Ala Gln Asp Lys Phe Gly Lys Thr Ala Phe Asp Ile Ser Ile Asp Asn
        130                 135                 140
```

```
Gly Asn Glu Asp Leu Ala Glu Ile Leu Gln
145                 150
```

<210> SEQ ID NO 144
<211> LENGTH: 154
<212> TYPE: PRT
<213> ORGANISM: Artificial Sequence
<220> FEATURE:
<223> OTHER INFORMATION: Synthetic (DARPin T_08)

<400> SEQUENCE: 144

```
Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Trp Asp
            20                  25                  30

Phe Leu Gly Leu Ile Pro Leu Arg Leu Ala Ala Ala Phe Gly His Leu
        35                  40                  45

Glu Ile Val Glu Val Leu Leu Lys Asn Gly Ala Asp Val Asn Ala Lys
    50                  55                  60

Asp Thr Tyr Gly Ile Thr Pro Leu His Leu Ala Ala Met Asn Gly His
65                  70                  75                  80

Leu Glu Ile Val Glu Val Leu Leu Lys Asn Gly Ala Asp Val Asn Ala
                85                  90                  95

Leu Asp Asn Thr Gly Ser Thr Pro Leu His Leu Ala Ala Asn Tyr Gly
            100                 105                 110

His Leu Glu Ile Val Glu Val Leu Leu Lys His Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150
```

<210> SEQ ID NO 145
<211> LENGTH: 154
<212> TYPE: PRT
<213> ORGANISM: Artificial Sequence
<220> FEATURE:
<223> OTHER INFORMATION: Synthetic (DARPin T_09)

<400> SEQUENCE: 145

```
Asp Leu Gly Lys Lys Leu Leu Glu Ala Ala Arg Ala Ser Gln Asp Asp
1               5                   10                  15

Glu Val Arg Ile Leu Met Ala Asn Gly Ala Asp Val Asn Ala Asn Asp
            20                  25                  30

Phe Gln Gly Ile Thr Pro Leu His Leu Ala Ala Ile Phe Gly His Leu
        35                  40                  45

Glu Ile Val Glu Val Leu Leu Lys Asn Gly Ala Asp Val Asn Ala Tyr
    50                  55                  60

Asp Gln Met Gly Met Thr Pro Leu His Leu Ala Ala Trp Thr Gly His
65                  70                  75                  80

Leu Glu Ile Val Glu Val Leu Leu Lys His Gly Ala Asp Val Asn Ala
                85                  90                  95

Asp Asp Thr His Gly Ala Thr Pro Leu His Leu Ala Ala His Thr Gly
            100                 105                 110

His Leu Glu Ile Val Glu Val Leu Leu Lys Tyr Gly Ala Asp Val Asn
        115                 120                 125

Ala Gln Asp Lys Phe Gly Lys Thr Ala Phe Asp Ile Ser Ile Asp Asn
    130                 135                 140
```

Gly Asn Glu Asp Leu Ala Glu Ile Leu Gln
145                 150

<210> SEQ ID NO 146
<211> LENGTH: 154
<212> TYPE: PRT
<213> ORGANISM: Artificial Sequence
<220> FEATURE:
<223> OTHER INFORMATION: Synthetic (DARPin T_16)

<400> SEQUENCE: 146

Asp Leu Gly Lys Lys Pro Leu Glu Ala Ala Arg Ala Gly Gln Asp Asp
1               5                   10                  15

Glu Val Arg Ile Leu Met Ala Asn Gly Ala Asp Val Asn Ala Tyr Asp
            20                  25                  30

Ile Val Gly Ile Thr Pro Leu His Leu Ala Ala Ile Phe Gly His Leu
        35                  40                  45

Glu Ile Val Glu Val Leu Leu Lys Asn Gly Ala Asp Val Asn Ala Tyr
    50                  55                  60

Asp Met Gln Val Asn Thr Pro Leu His Leu Ala Ala Trp Leu Gly His
65                  70                  75                  80

Leu Glu Ile Val Glu Val Leu Leu Lys Asn Gly Ala Asp Val Asn Ala
                85                  90                  95

Glu Asp Ser Tyr Gly Asn Thr Pro Leu His Leu Ala Ala Asp Lys Gly
            100                 105                 110

His Leu Glu Ile Val Glu Val Leu Leu Lys Asn Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 147
<211> LENGTH: 154
<212> TYPE: PRT
<213> ORGANISM: Artificial Sequence
<220> FEATURE:
<223> OTHER INFORMATION: Synthetic (DARPin T_25)

<400> SEQUENCE: 147

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Asp Asp
            20                  25                  30

Arg Arg Gly Ile Pro Pro Leu His Leu Ala Ala Ile Phe Gly His Leu
        35                  40                  45

Glu Ile Val Glu Val Leu Leu Lys His Gly Ala Asp Val Asn Ala His
    50                  55                  60

Asp Met Gln Gly Arg Thr Pro Leu His Leu Ala Ala Tyr Thr Gly His
65                  70                  75                  80

Leu Glu Ile Val Glu Val Leu Leu Lys Tyr Gly Ala Asp Val Asn Ala
                85                  90                  95

Ile Asp Phe Thr Gly His Thr Pro Leu His Leu Ala Ala Phe Arg Gly
            100                 105                 110

His Leu Glu Ile Val Glu Val Leu Leu Lys His Gly Ala Asp Val Asn
        115                 120                 125

Ala Gln Asp Lys Phe Gly Lys Thr Ala Phe Asp Ile Ser Ile Asp Asn

Gly Asn Glu Asp Leu Ala Glu Ile Leu Gln
145                 150

<210> SEQ ID NO 148
<211> LENGTH: 154
<212> TYPE: PRT
<213> ORGANISM: Artificial Sequence
<220> FEATURE:
<223> OTHER INFORMATION: Synthetic (DARPin T_27)

<400> SEQUENCE: 148

Asp Leu Gly Lys Lys Pro Leu Glu Ala Ala Arg Ala Gly Gln Asp Asp
1               5                   10                  15

Glu Val Arg Ile Leu Met Ala Asn Gly Ala Asp Val Asn Ala Tyr Asp
            20                  25                  30

Arg His Gly Leu Thr Pro Leu His Leu Val Ala Ile Phe Gly His Leu
        35                  40                  45

Glu Ile Val Glu Val Leu Leu Lys His Gly Ala Asp Val Asn Ala Ile
    50                  55                  60

Asp Ile Ile Gly Tyr Thr Pro Leu His Leu Ala Ala Trp Ser Gly His
65                  70                  75                  80

Leu Glu Ile Val Glu Val Leu Leu Lys Asn Gly Ala Asp Val Asn Ala
                85                  90                  95

Ser Asp Val Thr Gly Ser Thr Pro Leu His Leu Ala Ala Asp Lys Gly
            100                 105                 110

His Leu Glu Ile Val Glu Val Leu Leu Lys Tyr Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 149
<211> LENGTH: 154
<212> TYPE: PRT
<213> ORGANISM: Artificial Sequence
<220> FEATURE:
<223> OTHER INFORMATION: Synthetic (DARPin T_37)

<400> SEQUENCE: 149

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala His Asp
            20                  25                  30

Lys Arg Gly Ile Thr Pro Leu His Leu Ala Ala Ile Thr Gly His Leu
        35                  40                  45

Glu Met Val Glu Val Leu Leu Lys His Gly Ala Asp Val Asn Ala Val
    50                  55                  60

Asp Ile Gln Gly Arg Thr Pro Leu His Leu Ala Ala Trp Ile Gly His
65                  70                  75                  80

Leu Glu Ile Val Glu Val Leu Leu Lys Tyr Gly Ala Asp Val Asn Ala
                85                  90                  95

Met Asp Asp Phe Gly Glu Thr Pro Leu His Leu Ala Ala Arg Thr Gly
            100                 105                 110

His Leu Glu Ile Val Glu Val Leu Leu Lys His Gly Ala Asp Val Asn
        115                 120                 125

```
Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 150
<211> LENGTH: 154
<212> TYPE: PRT
<213> ORGANISM: Artificial Sequence
<220> FEATURE:
<223> OTHER INFORMATION: Synthetic (DARPin T_40)

<400> SEQUENCE: 150

Asp Leu Gly Lys Lys Leu Leu Glu Ala Ala Arg Ala Ser Gln Asp Asp
1               5                   10                  15

Glu Val Arg Ile Leu Met Ala Asn Gly Ala Asp Val Asn Ala Asn Asp
            20                  25                  30

Arg Val Gly Phe Thr Pro Leu His Leu Ala Ala Met Phe Gly His Leu
        35                  40                  45

Glu Leu Val Glu Val Leu Leu Lys Asn Gly Ala Asp Val Asn Ala Ile
    50                  55                  60

Asp Phe Gln Gly Lys Thr Pro Leu His Leu Ala Ala Gln Leu Gly His
65                  70                  75                  80

Leu Glu Ile Val Glu Val Leu Leu Lys Tyr Gly Ala Asp Val Asn Ala
                85                  90                  95

Leu Asp Ala Arg Gly Ile Thr Pro Leu His Leu Ala Ala Ile His Gly
            100                 105                 110

His Pro Glu Ile Val Glu Val Leu Leu Lys Tyr Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 151
<211> LENGTH: 220
<212> TYPE: PRT
<213> ORGANISM: Artificial Sequence
<220> FEATURE:
<223> OTHER INFORMATION: Synthetic (DARPin)
<220> FEATURE:
<221> NAME/KEY: MOD_RES
<222> LOCATION: (1)..(220)
<223> OTHER INFORMATION: each Xaa is independently Ala, Ile, Leu,
      Met, Phe, Pro, Trp, Val, Asn, Cys, Gln, Gly, Ser, Thr, Tyr, Asp,
      Glu, Arg, His or Lys

<400> SEQUENCE: 151

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Xaa Asp
            20                  25                  30

Xaa Xaa Gly Xaa Thr Pro Leu His Leu Ala Ala Xaa Xaa Gly His Leu
        35                  40                  45

Glu Ile Val Glu Val Leu Leu Lys Xaa Gly Ala Asp Val Asn Ala Xaa
    50                  55                  60

Asp Xaa Xaa Gly Xaa Thr Pro Leu His Leu Ala Ala Xaa Xaa Gly His
65                  70                  75                  80

Leu Glu Ile Val Glu Val Leu Leu Lys Xaa Gly Ala Asp Val Asn Ala
                85                  90                  95
```

```
Xaa Asp Xaa Xaa Gly Xaa Thr Pro Leu His Leu Ala Ala Xaa Xaa Gly
            100                 105                 110

His Leu Glu Ile Val Glu Val Leu Leu Lys Xaa Gly Ala Asp Val Asn
        115                 120                 125

Ala Xaa Asp Xaa Xaa Gly Xaa Thr Pro Leu His Leu Ala Ala Xaa Xaa
    130                 135                 140

Gly His Leu Glu Ile Val Glu Val Leu Leu Lys Xaa Gly Ala Asp Val
145                 150                 155                 160

Asn Ala Xaa Asp Xaa Xaa Gly Xaa Thr Pro Leu His Leu Ala Ala Xaa
            165                 170                 175

Xaa Gly His Leu Glu Ile Val Glu Val Leu Leu Lys Xaa Gly Ala Asp
                180                 185                 190

Val Asn Ala Gln Asp Lys Phe Gly Lys Thr Ala Phe Asp Ile Ser Ile
        195                 200                 205

Asp Asn Gly Asn Glu Asp Leu Ala Glu Ile Leu Gln
    210                 215                 220

<210> SEQ ID NO 152
<211> LENGTH: 10
<212> TYPE: PRT
<213> ORGANISM: Artificial Sequence
<220> FEATURE:
<223> OTHER INFORMATION: Synthetic peptide linker

<400> SEQUENCE: 152

Gly Gly Gly Gly Ser Gly Gly Gly Gly Ser
1               5                   10
```